(12) United States Patent
Purkayastha et al.

(10) Patent No.: US 7,906,341 B2
(45) Date of Patent: Mar. 15, 2011

(54) METHODS, MIXTURES, KITS AND COMPOSITIONS PERTAINING TO ANALYTE DETERMINATION

(75) Inventors: Subhasish Purkayastha, Acton, MA (US); Subhakar Dey, Billerica, MA (US); Scott B. Daniels, Northampton, MA (US)

(73) Assignee: DH Technologies Development Pte, Ltd., Singapore (SG)

( * ) Notice: Subject to any disclaimer, the term of this patent is extended or adjusted under 35 U.S.C. 154(b) by 0 days.

(21) Appl. No.: 11/770,212

(22) Filed: Jun. 28, 2007

(65) Prior Publication Data

US 2008/0241955 A1    Oct. 2, 2008

Related U.S. Application Data

(60) Provisional application No. 60/817,513, filed on Jun. 30, 2006.

(51) Int. Cl.
*G01N 24/00* (2006.01)

(52) U.S. Cl. ............. 436/173; 435/6; 435/18; 435/23; 435/25; 436/86; 436/111; 544/358; 544/392; 544/398; 544/399

(58) Field of Classification Search .................. None
See application file for complete search history.

(56) References Cited

U.S. PATENT DOCUMENTS

| 5,705,610 A | 1/1998 | Zuckermann et al. |
| 5,800,992 A | 9/1998 | Fodor et al. |
| 6,027,890 A | 2/2000 | Ness et al. |
| 6,270,976 B1 | 8/2001 | Schmidt et al. |
| 6,287,780 B1 | 9/2001 | Schmidt et al. |
| 6,475,807 B1 | 11/2002 | Geysen et al. |
| 7,364,911 B2* | 4/2008 | Aebersold et al. .......... 436/86 |
| 2006/0172319 A1* | 8/2006 | Yan et al. ................... 435/6 |

FOREIGN PATENT DOCUMENTS

| WO | WO 98/31830 A | 7/1998 |
| WO | WO 2004/019000 A | 3/2004 |
| WO | WO 2004/070352 A | 8/2004 |
| WO | WO 2004/086050 A | 10/2004 |
| WO | WO 2005/068446 A | 7/2005 |
| WO | WO 2006/017208 A | 2/2006 |
| WO | WO 2007/087534 A | 8/2007 |
| WO | WO 2007/100506 A | 9/2007 |

OTHER PUBLICATIONS

Ross, Philip L., et al, Multiplexed Proein Quantitation in *Saccharomyces cerevisiae* Using Amine-reactive Isobaric Tagging Reagents, 2004, Molecular & Cellular Proteomics, vol. 3, p. 1154-1169.*

(Continued)

*Primary Examiner* — Yelena G Gakh
*Assistant Examiner* — Robert Xu
(74) *Attorney, Agent, or Firm* — Grasso PLLC

(57) ABSTRACT

This invention pertains to methods, mixtures, kits and compositions pertaining to analyte determination by mass spectrometry using labeling reagents that comprise a nucleophilic reactive group that reacts with a functional group of an analyte to produce a labeled analyte. The labeling reagents can be used as isobaric sets, mass differential labeling sets or in a combination of isobaric and mass differential labeling sets.

48 Claims, 6 Drawing Sheets

Some Fragmentation Characteristics Of Various Isobaric/Isomeric Compounds

OTHER PUBLICATIONS

Lyakhova, E. A., et al. Synthesis and DNA-binding properties of N,N-dialkylglycine acridinylhydrazides, 2003, Pharmaceutical Chemistry Journal, vol. 37(4), pp. 16-21.*

Bottari P et al: "Design and Synthesis of Visible Isotope-Coded Affinity Tags for the Absolute Quantification of Specific proteins in Complex Mixtures" Bioconjugate Chemistry, ACS, Washington, D.C., U.S. vol. 15, No. 2, Feb. 21, 2004, pp. 380-388.

Dunayevskiy, Yuriy M.: "Application of Capillary Electrophoresis-Electrospray ionization Mass Spectrometry in the Determination of Molecular Diversity"; PNAS 1996, Proc. Natl. Acad. Sci. USA 93—Boston, MA, Jan. 30, 1996, pp. 6152-6157.

Gygi S P et al: "Quantitative Analysis of Complex Protein Mixtures using Isotope-Coded Affinity Tags" Nature Biotechnology, nature Publishing Group, New York, NY, U.S. vol. 17, No. 10, Oct. 1, 1999, pp. 994-999.

* cited by examiner

Some Fragmentation Characteristics Of Various Isobaric/Isomeric Compounds

⌐ ⌐ = Fragmentation Of Bond in a Mass Spectrometer

Possible Sets of Isobaric Labeling Reagents Based Upon Structures A & B wherein each * indicates substitution of $^{13}$C for $^{12}$C; $^{15}$N for $^{14}$N or $^{18}$O for $^{16}$O, as appropriate Possible Structures for Various Reporter Ions Note: Reporter Ion 113 is for a reporter without any Isotopically Enriched Sites Possible Sets of Mass Differential Tags Based Upon Structures A & B Set A Set B wherein each * indicates substitution of $^{13}C$ for $^{12}C$ or $^{15}N$ for $^{14}N$, as appropriate

METHODS, MIXTURES, KITS AND COMPOSITIONS PERTAINING TO ANALYTE DETERMINATION

PRIORITY AND RELATED APPLICATIONS

This application claims to the benefit of U.S. Provisional Patent Application Ser. No. 60/817,513 filed Jun. 30, 2006, incorporated herein by reference.

The section headings used herein are for organizational purposes only and should not be construed as limiting the subject matter described in any way.

FIELD

This invention pertains to methods, mixtures, kits and compositions pertaining to analyte determination by mass spectrometry.

INTRODUCTION

This invention pertains to the determination of an analyte or analytes by mass analysis. An analyte can be any molecule of interest that can be reacted with an amine or hydrazine group to thereby form a stable adduct. For example, the reactive group of the analyte can be a carboxylic acid, aldehyde or ketone group wherein the adduct formed from the aldehyde or ketone group can be reduced to form the stable labeled analyte. Non-limiting examples of analytes include, but are not limited to, biologically important carboxylic acid compounds (e.g., prostaglandins, fatty acids, carnitines, etc.), proteins, peptides, carbohydrates, lipids, amino acids, steroids and other small molecules having a mass of less than 1500 daltons that comprise an appropriate reactive functional group. Analytes can be determined using unique labeling reagents that permit the relative and/or absolute quantification of the analytes in complex mixtures. The labeling reagents can be used in sets for the analysis of complex sample mixtures wherein the labeling reagents can be isobaric (including isomeric isobars) and/or comprise labeling reagents of unique gross mass (i.e. be mass differential labeling reagents also known as 'mass differential tags', herein).

For example, multiplexed qualitative and quantitative analysis of biologically important compounds (for example, carboxy acid compounds such as prostaglandins, fatty acids, carnitines, etc.), can be performed utilizing isobaric and/or mass differential tags, and, in some embodiments, multiple reaction monitoring (MRM) on triple quadrupole, linear ion trap instruments.

With reference to FIG. 1a, labeling reagents of an isobaric set can comprise a reporter moiety, a balance (or linker) moiety and a reactive group wherein the reactive group is substituted by the analyte in the analyte reacted form of the composition. Examples of labeling reagents and labeled analytes of this general formula have been disclosed in, for example, published copending and commonly owned U.S. patent application Ser. Nos. US 2004-0219685 A1, US 2005-0114042 A1, US 2005-0147982 A1, US 2005-0147985 A1, US 2005-0147987 A1, US 2005-0148771 A1, US 2005-0148773 A1 and US 2005-0148774 A1.

In some embodiments, isobaric (including isomeric isobars) labeling reagents can be used to label, for example, the analytes of two or more different samples wherein the different labeling reagents of a set all have the same gross mass but wherein each reporter moiety can be uniquely isotopically encoded such that each reporter moiety of the set has a unique gross mass. Because all the reagents of the set can have the same gross mass but can comprise a reporter moiety of unique gross mass, the balance (or linker) can generally (but not necessarily) also comprise one or more heavy atom isotopes to thereby "balance" the mass of each unique reporter such that the reporter/linker combination of each labeling reagent of the set has the same gross mass.

In some embodiments, mass differential labeling reagents (i.e. mass differential tags) can be used to label, for example, the analytes of two or more different samples wherein the different labeling reagents of a set all have a distinct mass (i.e. can all possess a known mass difference as compared with other reagents of the set). Because all the reagents of the set can have a known mass difference, the labeling reagents need not be fragmented in order to quantify the relative amounts of like analytes in two different samples. However, in some embodiments, the labeling reagents can be fragmentable.

As discussed in more detail below, compounds of various general formulas (including sets comprising compounds of the same general structural formula but for their isotopic coding) can be prepared in both isobaric and/or mass differential sets. Generally, sets can be used either as an isobaric set of labels or as a mass differential set of labels although the simultaneous use of a set of isobaric labeling reagents in combination with a set of mass differential labeling reagents in the same experiment is envisioned as an embodiment of this invention.

An example of a new labeling reagent (or labeled analyte), as discussed more thoroughly herein, is illustrated in FIG. 1b. Although illustrated in unsubstituted form (except for $R_1$ and $R_2$), it is to be understood that the labeling reagent can be substituted or unsubstituted. In the illustration, certain bonds are shown as being fragmented to thereby release at least the unique reporter moiety, and optionally the balance moiety, from the labeling reagent or labeled analyte. For the labeled analytes that have been labeled with isobaric labeling reagents, each unique reporter ion (sometimes referred to as the signature ion) observed in the mass spectrometer (typically in $MS^n$ analysis wherein n is an integer greater than 1) can be used to quantify the amount of analyte in a sample or sample mixture. For labeled analytes that have been labeled with mass differential labeling reagents, quantification can be determined by the relative intensity of the labeled analytes in $MS^1$ analysis.

FIG. 4a illustrates two sets of 4 different encoded versions of labeling reagents with the set of AI to AIV having the basic structure illustrated in FIG. 1b (for example $R_1$ and $R_2$ can be, independently of the other, hydrogen or methyl), wherein the asterisk (*) is used to indicate where a $^{13}C$ atom is substituted for a $^{12}C$ atom, where a $^{15}N$ atom is substituted for a $^{14}N$ atom or where an $^{18}O$ is substituted for a $^{16}O$ atom, as appropriate. These sets can be used to facilitate at least a 4-plex experiment. However, with further substitution of the compounds with heavy atom isotopes, it is expected that more than 4 different compounds can be prepared such that greater than a 4-plex experiment could be performed.

Generally, labeling reagents, labeled analytes and some intermediates to the labeling reagents and/or labeled analytes can be represented by compounds of formula I;

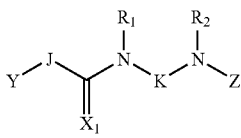

including a salt form thereof and/or a hydrate form thereof, wherein Z can be hydrogen or a covalently linked analyte and wherein the atoms or groups $X_1$, $R_1$, $R_2$, Y, J, and K are described in more detail below.

Accordingly, in some embodiments analytes can be labeled by reaction of the analyte with a labeling reagent represented by compounds of formula I';

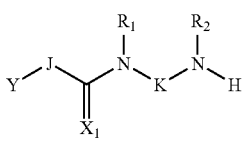

including a salt form thereof and/or a hydrate form thereof, wherein the atoms or groups $R_1$, $R_2$, Y, J, and K are described in more detail below. In some embodiments, the labeling reagents can be used in sets, wherein the sets comprise isomeric and/or isobaric compounds, whereby the labeled analytes can likewise be isomeric and/or isobaric. In some embodiments, the labeling reagents can be used in set, wherein the sets comprise mass differential labeling reagents (i.e. labeling reagents of different gross mass). In some embodiments, isobaric (including isobaric isomers) and mass differential labeling reagents are used together.

Further, in some embodiments a labeled analyte therefore can be represented by formula I";

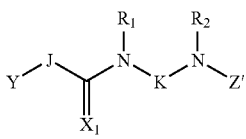

including a salt form thereof and/or a hydrate form thereof, wherein Z" represents the analyte covalently linked to the labeling reagent and wherein the atoms or groups $R_1$, $R_2$, Y, J, and K are described in more detail below.

As described herein, sets of two, three, four, or more, isobaric and/or mass differential labeling reagents can be made thereby permitting experiments of 4-plex or greater. For example, it is possible to simultaneously identify and/or quantify an analyte in 4 (or more) different samples that have each been differentially labeled and then mixed. For an isobaric set of labels, quantification can be achieved by determination of the relative abundance of each unique reporter ion associated with each different labeling reagent of the isobaric set. For a mass differential set, quantification can be achieved by determination of the relative abundance of each labeled analyte associated with each different labeling reagent of the mass differential set.

Thus, embodiments of this invention are particularly well suited for the multiplex analysis of complex sample mixtures. For example, some embodiments of this invention can be used in proteomic analysis and/or genomic analysis as well as for correlation studies related to genomic and/or proteomic analysis. Some embodiments of this invention can also be used for small molecule analysis, such as for carnitine, carbohydrate, lipid, steroid, vitamin, prostaglandin, fatty acid, and/or amino acid analysis. Experimental analysis for which the isobaric and/or mass differential reagents can be used includes, but is not limited to, time course studies, biomarker analysis, multiplex proteomic analysis, mudpit experiments, affinity pull-downs, determination of post-translational modifications (PTMs) (see for example published United States Patent Application No. US 2005-0208550 A1) and multiple control experiments.

DRAWINGS

The skilled artisan will understand that the drawings, described below, are for illustration purposes only. The drawings are not intended to limit the scope of the present teachings in any way.

Figure 1A:
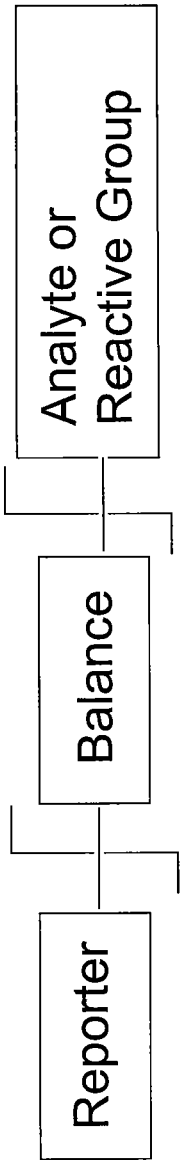
FIG. 1a is an illustration of the elements of a labeling reagent or labeled analyte and some fragmentation characteristics.

All literature and similar materials cited in this application, including but not limited to, patents, patent applications, articles, books, treatises, and internet web pages, regardless of the format of such literature and similar materials, are expressly incorporated by reference herein in their entirety for any and all purposes.

DEFINITIONS

For the purposes of interpreting this specification, the following definitions will apply and whenever appropriate, terms used in the singular will also include the plural and vice versa. In the event that any definition set forth below conflicts with the usage of that word in any other document, including any document incorporated herein by reference, the definition set forth below shall always control for purposes of interpreting this specification and its associated claims unless a contrary meaning is clearly intended (for example in interpreting the document where the term is originally used). The use of "or" herein means "and/or" unless stated otherwise or where the use of "and/or" is clearly inappropriate. The use of "a" herein means "one or more" unless stated otherwise or where the use of "one or more" is clearly inappropriate. The use of "comprise," "comprises," "comprising" "include," "includes," and "including" are interchangeable and not intended to be limiting. Furthermore, where the description of one or more embodiments uses the term "comprising," those skilled in the art would understand that in some specific instances, the embodiment or embodiments can be alternatively described using language "consisting essentially of" and/or "consisting of." It should also be understood that in some embodiments the order of steps or order for performing certain actions is immaterial so long as the present teachings remain operable. Moreover, in some embodiments two or more steps or actions can be conducted simultaneously.

a.) As used herein, "analyte" refers to a molecule of interest that may be determined. Non-limiting examples of analytes include, but are not limited to, proteins, peptides, (either DNA or RNA), carbohydrates, lipids, amino acids, steroids, vitamins, prostaglandins, fatty acids, carnitines and other small molecules with a molecular weight of less than 1500 daltons (Da). The source of the analyte, or the sample comprising the analyte, is not a limitation as it can come from any source. The analyte or analytes can be natural or synthetic. Non-limiting examples of sources for the analyte, or the sample comprising the analyte, include cells or tissues, or cultures (or subcultures) thereof. Non-limiting examples of analyte sources include, but are not limited to, crude or processed cell lysates, body fluids, tissue extracts, cell extracts or fractions (or portions) from a separations process such as a chromatographic separation, a 1D electrophoretic separation, a 2D electrophoretic separation or a capillary electrophoretic separation. Body fluids include, but are not limited to, blood, urine, feces, spinal fluid, cerebral fluid, amniotic fluid, lymph fluid or a fluid from a glandular secretion. By processed cell lysate we mean that the cell lysate is treated, in addition to the treatments needed to lyse the cell, to thereby perform additional processing of the collected material. For example, the sample can be a cell lysate comprising one or more analytes that are peptides formed by treatment of the cell lysate with one or more proteolytic enzymes to thereby digest precursor peptides and/or proteins.

b.) Except as when clearly not intended based upon the context in which it is being used (e.g. when made in reference to a specific structure that dictates otherwise), "ester" refers to both an ester and/or a thioester.

c.) As used herein, "fragmentation" refers to the breaking of a covalent bond.

d.) As used herein, "fragment" refers to a product of fragmentation (noun) or the operation of causing fragmentation (verb).

e.) As used herein, "hydrate form" refers to any hydration state of a compound or a mixture or more than one hydration state of a compound. For example, a labeling reagent discussed herein can be a hemihydrate, a monohydrate, a dihydrate, etc. Moreover, a sample of a labeling reagent described herein can comprise monohydrate, dihydrate and hemihydrate forms.

f.) As used herein, a halogen group refers to —F, —Cl, —Br, or —I.

g.) As used herein with respect to a compound, "isotopically enriched" refers to a compound (e.g. labeling reagent) that has been enriched with one or more heavy atom isotopes (e.g. stable isotopes such as deuterium ('D'), $^{13}$C, $^{15}$N, $^{18}$O, $^{37}$Cl or $^{81}$Br). In some embodiments, unstable isotopes can also be used (e.g. $^{14}$C or $^{3}$H). By "enriched" we mean that the amount of heavy atom isotope exceeds natural isotopic abundance. In various embodiments, the isotopically enriched compound can comprise 1, 2, 3, 4, 5, 6, 7, 8, 9, 10, 11, 12, 13, 14, 15, 16, 17, 18, 19, 20, 21, 22, 23, 24, 25, 26, 27, 28, 29, 30 or more isotopically enriched sites.

Because isotopic enrichment is not 100% effective, there can be impurities in a sample of the compound that are of lesser states of enrichment and these will have a lower mass. Likewise, because of over-enrichment (e.g. undesired enrichment) and because of natural isotopic abundance, there can be impurities in a sample of the compound that are of greater mass. In some embodiments, each incorporated heavy atom isotope can be present at an isotopically enriched site in at least 80 percent isotopic purity. In some embodiments, each incorporated heavy atom isotope can be present at an isotopically enriched sited in at least 93 percent isotopic purity. In some embodiments, each incorporated heavy atom isotope can be present at an isotopically enriched site in at least 96 percent isotopic purity. In some embodiments, each incorporated heavy atom isotope can be present at an isotopically enriched site in at least 98 percent purity.

h.) As used herein, "isotopically enriched site" refers to the position in a compound where a heavy atom isotope is substituted for a light version of the atom (e.g. substitution of $^{13}$C for $^{12}$C, $^{18}$O for $^{16}$O, $^{15}$N for $^{14}$N or deuterium for hydrogen).

i.) As used herein with respect to a compound, "light" refers to the compound as not being enriched with a heavy atom isotope. As used herein with respect to an atom, "light" refers to the lowest mass isotope of the atom. As used herein with respect to a compound, "heavy" refers to the compound as being enriched with at least one heavy atom isotope. As used herein with respect to an atom, "heavy" refers to a heavy mass isotope of the atom.

j.) As used herein, "labeling reagent" refers to a moiety suitable to mark an analyte for determination. The term label is synonymous with the terms tag and mark and other equivalent terms and phrases. For example, a labeled analyte can also be referred to as a tagged analyte or a marked analyte. Accordingly the terms "label", "tag", "mass tag", "mark" and derivatives of these terms, are equivalent and interchangeable and refer to a moiety suitable to mark, or that has marked, an analyte for determination. Sometimes a labeling reagent can be referred to a tagging reagent, a mass tagging reagent or simply as a mass tag (e.g. mass differential tag).

k.) As used herein, "natural isotopic abundance" refers to the level (or distribution) of one or more heavy isotopes found in a compound based upon the natural prevalence of an isotope or isotopes in nature. For example, a natural compound obtained from living plant matter can typically contain about 1.08% $^{13}$C relative to $^{12}$C.

l.) As used herein, isobars are structurally and chemically indistinguishable compounds (except for isotopic content and/or distribution of heavy atom isotopes) of the same nominal gross mass. By "chemically indistinguishable" we mean that the isobars comprise the same general chemical structure (but for the distribution of heavy atom isotopes) and possess substantially the same chemical reactivity and separations properties.

m.) As used herein, "support", "solid support", "solid carer" or "resin" means any solid phase material. Solid support encompasses terms such as "support", "synthesis support", "solid phase", "surface" "membrane" and/or "support". A solid support can be composed of organic polymers such as polystyrene, polyethylene, polypropylene, polyfluoroethylene, polyethyleneoxy, and polyacrylamide, as well as co-polymers and grafts thereof. A solid support can also be inorganic, such as glass, silica, controlled-pore-glass (CPG), or reverse-phase silica. The configuration of a solid support can be in the form of beads, spheres, particles, granules, a gel, a membrane or a surface. Surfaces can be planar, substantially planar, or non-planar. Solid supports can be porous or non-porous, and can have swelling or non-swelling characteristics. A solid support can be configured in the form of a well, depression or other container, vessel, feature or location. A plurality of solid supports can be configured in an array at various locations, addressable for robotic delivery of reagents, or by detection methods and/or instruments.

n.) As used herein, "sample, or a fraction thereof" or "sample fraction" can be used to refer to a fraction of a sample. The fraction of the sample can be generated either by simply withdrawing a fraction of a sample else it can be generated by performing a separations process that results in the sample being fractionated into two or more fractions. Unless the content of the description indicates otherwise, these phrases are equivalent and interchangeable and refer to any type of creation of a fraction (or portion) of a sample.

o.) As used herein, "signature ion" and "reporter ion" are interchangeable and both refer to the reporter ion of unique mass produced from the reporter moiety by fragmentation of a labeling reagent or labeled analyte. The signature ion or reporter ion can be used to identify the unique labeling reagent used to label an analyte and its peak intensity in MS/MS analysis (or MS$^n$ analysis) can be correlated with the amount of labeled analyte present in the sample that is analyzed. As used herein, the signature ion or reporter ion is sometimes merely referred to as a reporter. As used herein, the reporter moiety is also sometimes merely referred to as a reporter. It is to be understood that the reporter moiety refers to the group attached to a labeling reagent, labeled analyte or fragment thereof and the reporter ion refers to the fragment ion generated upon fragmentation of the bond that links the reporter moiety to the labeling reagent, labeled analyte or a fragment thereof. Accordingly, the context in which the word "reporter" is used can indicate its intended meaning. It also is to be understood that the phrase "unique reporter moiety" is equivalent to, and interchangeable with, "reporter moiety of unique mass" and that "unique reporter ion" is equivalent to, and interchangeable with, "reporter ion of unique mass".

p.) As used herein, the term "salt form" includes a salt of a compound or a mixture of salts of a compound. In addition, zwitterionic forms of a compound are also included in the term "salt form." Salts of compounds having an amine, or other basic group can be obtained, for example, by reaction with a suitable organic or inorganic acid, such as hydrogen chloride, hydrogen bromide, acetic acid, perchloric acid and the like. Compounds with a quaternary ammonium group may also contain a counteranion such as chloride, bromide, iodide, acetate, perchlorate and the like. Salts of compounds having a carboxylic acid, or other acidic functional group, can be prepared by reacting the compound with a suitable base, for example, a hydroxide base. Accordingly, salts of acidic functional groups may have a countercation, such as sodium, potassium, magnesium, calcium, etc.

q.) As used herein, "synthetic compound" refers to a compound that is created by manipulation of processes including the manipulation of naturally occurring pathways. Thus, a synthetic compound can be produced using synthetic chemistry techniques. However, as used herein, "synthetic compound" is also intended to include compounds that are produced, for example, by enzymatic methods, including for example, feeding isotopically enriched compounds to organisms, such as bacteria or yeast, that alter them to thereby produce the isotopically enriched labeling reagents, or intermediates of the labeling reagents, described herein.

r.) As used herein, "synthetically enriched" or "enriched synthetically" refers to the manipulation of a synthetic or natural process to thereby produce a synthetic compound such as the isotopically enriched labeling reagents, or intermediates to the labeling reagents, described herein.

s.) It is well accepted that the mass of an atom or molecule can be approximated, often to the nearest whole number atomic mass unit or the nearest tenth or hundredth of an atomic mass unit. As used herein, "gross mass" refers to the absolute mass as well as to the approximate mass within a range where the use of isotopes of different atom types are so close in mass that they are the functional equivalent for the purpose of balancing the mass of the reporter and/or linker moieties (so that the gross mass of the reporter/linker combination is the same within a set or kit of isomeric and/or isobaric labeling reagents) whether or not the very small difference in mass of the different isotopes types used can be detected.

For example, the common isotopes of oxygen have a gross mass of 16.0 (actual mass 15.9949) and 18.0 (actual mass 17.9992), the common isotopes of carbon have a gross mass of 12.0 (actual mass 12.00000) and 13.0 (actual mass 13.00336) and the common isotopes of nitrogen have a gross mass of 14.0 (actual mass 14.0031) and 15.0 (actual mass 15.0001). Whilst these values are approximate, one of skill in the art can appreciate that if one uses the $^{18}$O isotope at an isotopically enriched site within one label of a set, the additional 2 mass units (over the isotope of oxygen having a gross mass of 16.0) can, for example, be compensated for in a different label of the set comprising $^{16}$O by incorporating, elsewhere in the label, two carbon $^{13}$C atoms, instead of two $^{12}$C atoms, two $^{15}$N atoms, instead of two $^{14}$N atoms or even one $^{13}$C atom and one $^{15}$N atom, instead of a $^{12}$C and a $^{14}$N, to compensate for the $^{18}$O. In this way two different labels of an isobaric set can have the same gross mass since the very small actual differences in mass between the use of two $^{13}$C atoms (instead of two $^{12}$C atoms), two $^{15}$N atoms (instead of two $^{14}$N atoms), one $^{13}$C and one $^{15}$N (instead of a $^{12}$C and $^{14}$N) or one $^{18}$O atom (instead of one $^{16}$O atom), to thereby achieve an increase in mass of two Daltons in all of the labels of the set or kit, is not an impediment to the nature of the analysis.

It is clear that the distribution of the same heavy atom isotopes within a structure is not the only consideration for the creation of sets of isobaric and/or mass differential labeling reagents. It is possible to mix heavy atom isotope types to achieve isobars or mass differential labels of a desired gross mass. In this way, both the selection (combination) of heavy atom isotopes as well as their distribution is available for consideration in the production of the isobaric and/or mass differential labeling reagents useful for embodiments of this invention.

t.) As used herein, the term "alkyl" refers to a straight chained or branched $C_2$-$C_8$ hydrocarbon or a cyclic $C_3$-$C_8$ hydrocarbon (i.e. a cycloalkyl group such as a cyclopropyl group, a cyclobutyl group, a cyclopentyl group, a cyclohexyl group or a cyclohexylmethylene group) that can be completely saturated. When used herein, the term "alkyl" refers to a group that may be substituted or unsubstituted. In some embodiments, the term "alkyl" is also intended to refer to those compounds wherein one or more methylene groups in the alkyl chain can be replaced by a heteroatom such as —O—, —Si— or —S—. In some embodiments, alkyl groups can be straight chained or branched $C_2$-$C_6$ hydrocarbons or cyclic $C_3$-$C_6$ hydrocarbons that can be completely saturated.

u.) As used herein, the term "alkylene" refers to a straight or branched alkyl chain or a cyclic alkyl group that comprises at least two points of attachment to at least two moieties (e.g., —{CH$_2$}— (methylene), —{CH$_2$CH$_2$}—, (ethylene),

etc., wherein the brackets indicate the points of attachment. When used herein the term "alkylene" refers to a group that may be substituted or unsubstituted. In some embodiments, the term "alkylene" is also intended to refer to those compounds wherein one or more methylene groups, if any, in an alkyl chain of the alkylene group can be replaced by a heteroatom such as —O—, —Si— or —S—. In some embodiments, an alkylene group can be a C$_1$-C$_{10}$ hydrocarbon. In some embodiments, an alkylene group can be a C$_2$-C$_6$ hydrocarbon.

v.) As used herein, the term "alkenyl" refers to a straight chained or branched C$_2$-C$_8$ hydrocarbon or a cyclic C$_3$-C$_8$ hydrocarbon that comprises one or more double bonds. When used herein, the term "alkenyl" refers to a group that can be substituted or unsubstituted. In some embodiments, the term "alkenyl" is also intended to refer to those compounds wherein one or more methylene groups, if any, in an alkyl chain of the alkenyl group can be replaced by a heteroatom such as —O—, —Si— or —S—. In some embodiments, alkenyl groups can be straight chained or branched C$_2$-C$_6$ hydrocarbons or cyclic C$_3$-C$_6$ hydrocarbons that comprise one or more double bonds.

w.) As used herein, the term "alkenylene" refers to an alkenyl group that comprises two points of attachment to at least two moieties. When used herein the term "alkenylene" refers to a group that may be substituted or unsubstituted. In some embodiments, the term "alkenylene" is also intended to refer to those compounds wherein one or more methylene groups, if any, in an alkyl chain of the alkenylene group can be replaced by a heteroatom such as —O—, —Si— or —S—.

x.) As used herein, the term "alkynyl" refers to a straight chained or branched C$_2$-C$_8$ hydrocarbon or a cyclic C$_3$-C$_8$ hydrocarbon that comprises one or more triple bonds. When used herein, the term "alkynyl" refers to a group that may be substituted or unsubstituted. In some embodiments, the term "alkynyl" is also intended to refer to those compounds wherein one or more methylene groups, if any, in an alkyl chain of the alkynyl group can be replaced by a heteroatom such as —O—, —Si— or —S—. In some embodiments, alkynyl groups can be straight chained or branched C$_2$-C$_6$ hydrocarbons or cyclic C$_3$-C$_6$ hydrocarbons that have one or more triple bonds.

y.) As used herein, the term "alkynylene" refers to an alkynyl group that comprises two points of attachment to at least two moieties. When used herein the term "alkynylene" refers to a group that may be substituted or unsubstituted. In some embodiments, the term "alkynylene" is also intended to refer to those compounds wherein one or more methylene groups, if any, in an alkyl chain of the alkynylene group can be replaced by a heteroatom such as —O—, —Si— or —S—.

z.) As used herein, the term "aliphatic" refers to any of the straight, branched, or cyclic alkyl, alkenyl, and alkynyl moieties as defined above. When used herein the term "aliphatic" refers to a group that may be substituted or unsubstituted.

aa.) As used herein, the term "aryl", either alone or as part of another moiety (e.g., arylalkyl, etc.), refers to carbocyclic aromatic groups such as phenyl. Aryl groups also include fused polycyclic aromatic ring systems in which a carbocyclic aromatic ring is fused to another carbocyclic aromatic ring (e.g., 1-naphthyl, 2-naphthyl, 1-anthracyl, 2-anthracyl, etc.) or in which a carbocylic aromatic ring is fused to one or more carbocyclic non-aromatic rings (e.g., tetrahydronaphthylene, indan, etc.). As used herein, the term "aryl" refers to a group that may be substituted or unsubstituted.

ab.) As used herein, the term "heteroaryl," refers to an aromatic heterocycle that comprises 1, 2, 3 or 4 heteroatoms selected, independently of the others, from nitrogen, sulfur and oxygen. As used herein, the term "heteroaryl" refers to a group that may be substituted or unsubstituted. A heteroaryl may be fused to one or two rings, such as a cycloalkyl, an aryl, or a heteroaryl ring. The point of attachment of a heteroaryl to a molecule may be on the heteroaryl, cycloalkyl, heterocycloalkyl or aryl ring, and the heteroaryl group may be attached through carbon or a heteroatom. Examples of heteroaryl groups include imidazolyl, pyrrolyl, pyridinyl, pyrimidyl, pyrazinyl, pyridazinyl, quinolyl, isoquinolinyl, indazolyl, indolizinyl, imidazopyridinyl, pyrazolyl, triazolyl, tetrazolyl, indolyl, tetrahydroindolyl, azaindolyl, imidazopyridyl, quinazolinyl, purinyl, pyrrolo[2,3]pyrimidyl or pyrazolo[3,4] pyrimidyl, each of which can be optionally substituted.

ac.) As used herein, the term "arylene" refers to an aryl or heteroaryl group that comprises at least two points of attachment to at least two moieties (e.g., phenylene, etc.). The point of attachment of an arylene fused to a carbocyclic, non-aromatic ring may be on either the aromatic, non-aromatic ring. As used herein, the term "arylene" refers to a group that may be substituted or unsubstituted.

ad.) As used herein, the term "arylalkyl" refers to an aryl or heteroaryl group that is attached to another moiety via an alkylene linker. As used herein, the term "arylalkyl" refers to a group that may be substituted or unsubstituted. In some embodiments, the term "arylalkyl" is also intended to refer to those compounds wherein one or more methylene groups, if any, in the alkyl chain of the arylalkyl group can be replaced by a heteroatom such as —O—, —Si— or —S—.

ae.) As used herein, the term "arylalkylene" refers to an arylalkyl group that has at least two points of attachment to at least two moieties. The second point of attachment can be on either the aromatic ring or the alkylene group. As used herein, the term "arylalkylene" refers to a group that may be substituted or unsubstituted. In some embodiments, the term "arylalkylene" is also intended to refer to those compounds wherein one or more methylene groups, if any, in the alkyl chain of the arylalkylene group can be replaced by a heteroatom such as —O—, —Si— or —S—. When an arylalkylene is substituted, the substituents may be on either or both of the aromatic ring or the alkylene portion of the arylalkylene.

af.) As used herein, the terms "optionally substituted" and "substituted or unsubstituted" are equivalent and interchangeable. Suitable substituents for any an alkyl, an alkylene, an alkenyl, an alkenylene, an alkynyl, an alkynylene, an aryl, an aryl alkyl, an arylene, a heteroaryl or an arylalkylene group includes any substituent that is stable under the reaction conditions used in embodiments of this invention. Non limiting examples of suitable substituents can include: an alkyl (e.g., methyl, ethyl, n-propyl, isopropyl, n-butyl, isobutyl, sec butyl, t-butyl, cyclohexyl, etc.) group, a haloalkyl (e.g., trifluoromethyl, 2,2,2-trifluoroethyl-, etc.) group, an alkoxy (e.g., methoxy, ethoxy, etc.) group, an aryl (e.g., phenyl) group, an arylalkyl (e.g., benzyl) group, a nitro group, a cyano group, a quaternized nitrogen atom or a halogen group (e.g., fluorine, chlorine, bromine and/or iodine) group.

In addition, any portion of an alkyl, an alkylene, an alkenyl, an alkenylene, an alkynyl, an alkynylene, an aryl, an aryl alkyl, an arylene, a heteroaryl or an arylalkylene group may also be substituted with =O or =S.

ag.) As used herein, the term "active ester" refers to compounds that can react readily under basic conditions with amines, alcohols and certain thiols to provide amides, esters and thioesters, respectively. Additional reference is made to: Leo A Paquette, *Encyclopedia of Reagents for Organic Synthesis, Vol.* 2, John Wiley and Sons, New York, 1995 as evidence that "active ester" is a term well-established in field of organic chemistry.

ah.) As used herein, the term "heterocyclic ring" refers to any cyclic molecular structure comprising atoms of at least two different elements in the ring or rings. Additional reference is made to: *Oxford Dictionary of Biochemistry and Molecular Biology*, Oxford University Press, Oxford, 1997 as evidence that "heterocyclic ring" is a term well-established in field of organic chemistry.

ai.) As used herein, the term "leaving group" refers to any atom or group, charged or uncharged, that departs during a substitution or displacement reaction from what is regarded as the residual or main part of the substrate of the reaction. Additional reference is made to: *Oxford Dictionary of Biochemistry and Molecular Biology*, Oxford University Press, Oxford, 1997 as evidence that "leaving group" is a term well-established in field of organic chemistry.

aj.) As used herein, the term "protecting group" refers to a chemical group that is reacted with, and bound to, a functional group in a molecule to prevent the functional group from participating in subsequent reactions of the molecule but which group can subsequently be removed to thereby regenerate the unprotected functional group. Additional reference is made to: *Oxford Dictionary of Biochemistry and Molecular Biology*, Oxford University Press, Oxford, 1997 as evidence that "protecting group" is a term well-established in field of organic chemistry.

DESCRIPTION OF VARIOUS EMBODIMENTS

It is to be understood that the discussion set forth below in this "General" section can pertain to some, or to all, of the various embodiments of the invention described herein.

I. General

Labeling Reagent(s):

A labeling reagent can comprises a reporter moiety, a balance moiety (or linker moiety) and a reactive group (FIG. 1a). Labeling reagents can be reacted with analytes to thereby produce labeled analytes. In some embodiments, the labeling reagents are organized into sets. In some embodiments, the sets can be isomeric and/or isobaric. In some embodiments the sets can be mass differential. In some embodiments, the sets can be both isobaric and/or isomeric and mass differential.

Figure 2:
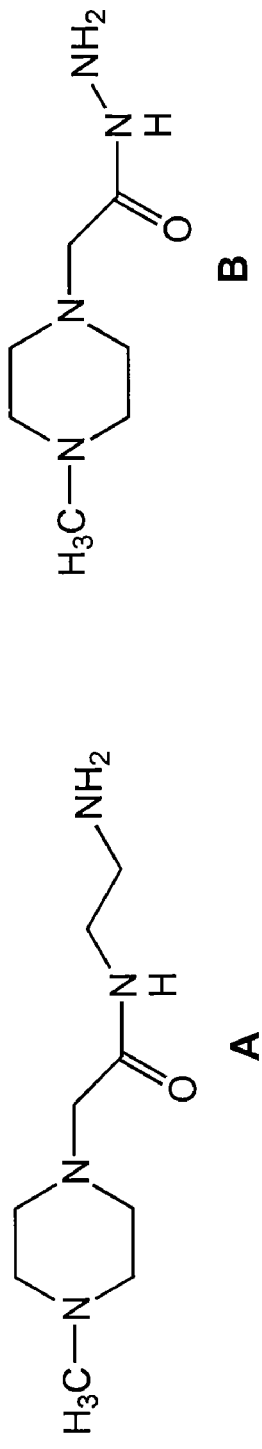
FIG. 2 is an illustration of the general structure of two different labeling reagents (i.e. structure A and structure B).
Figure 3:
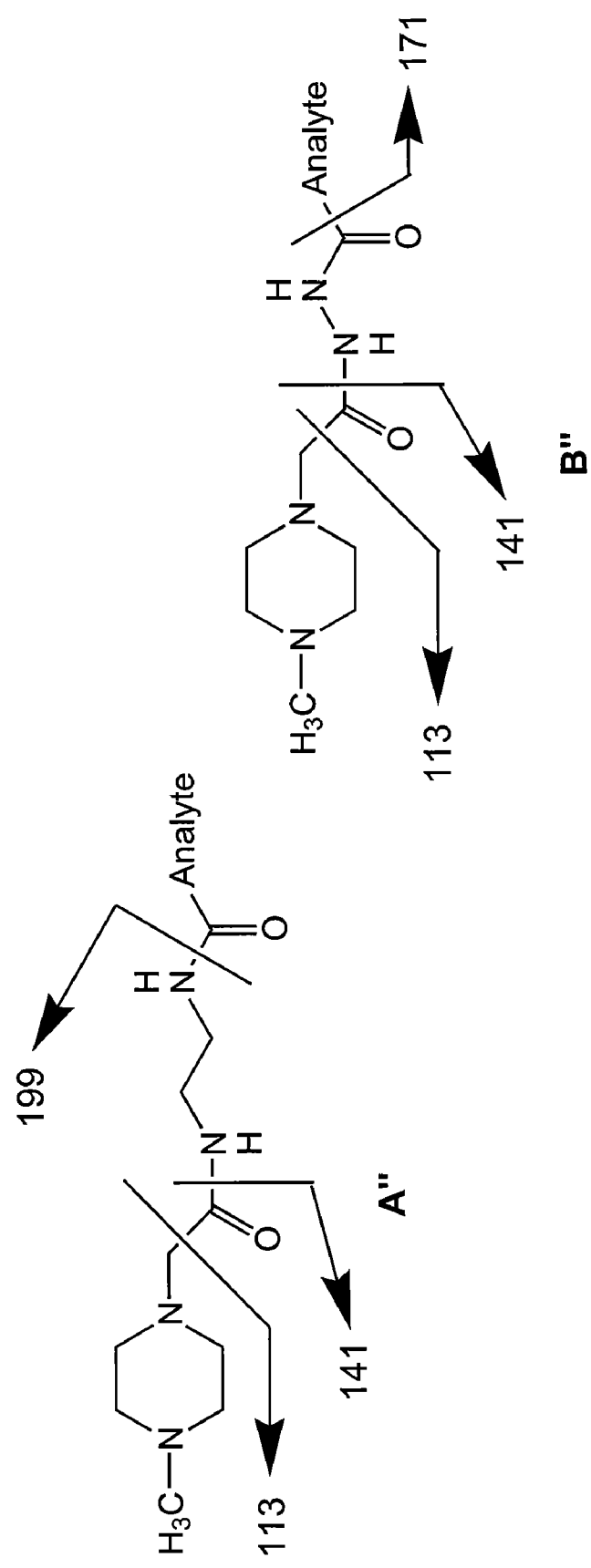
FIG. 3 is an illustration of possible fragmentation properties of analytes labeled with labeling reagents according to structures A and B (represented as labeled analytes A" and B") as well as an illustration of the mass of possible fragments generated therefrom.
Figure 5A:
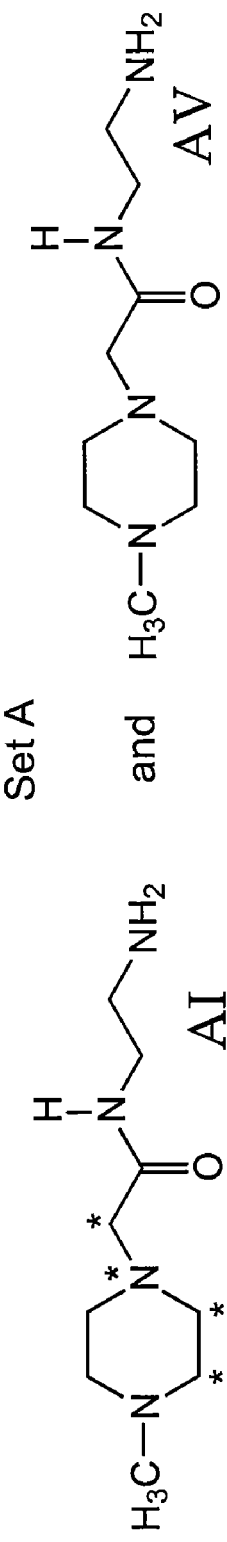
FIGS. 5a and 5b are illustrations of two possible sets of mass differential labeling reagents (based upon structure A and structure B, respectively)
Figure 5B:
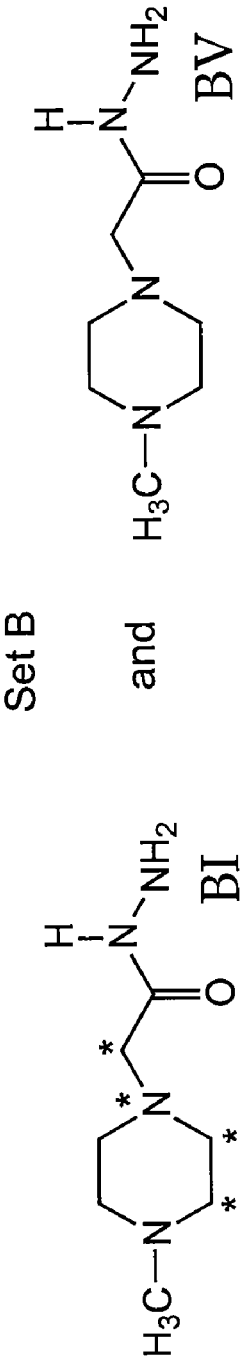
Figure 6A:
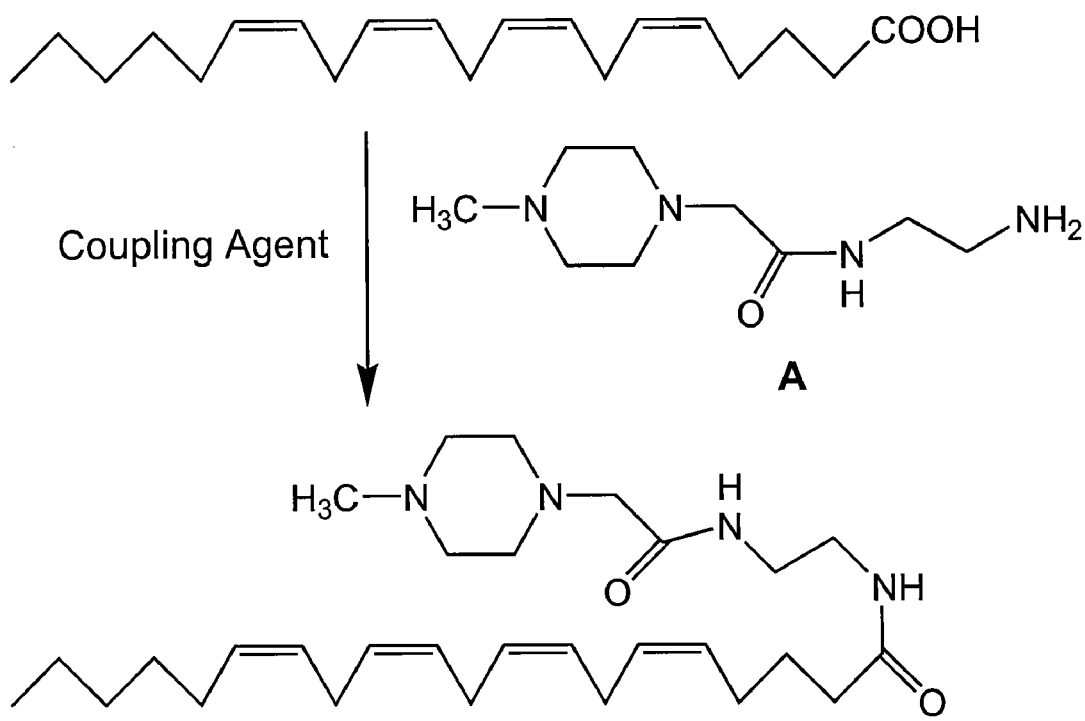
FIGS. 6a and 6b are illustrations of the processes of labeling analytes with the exemplary compounds of structures A and B, respectively.
Figure 6B:
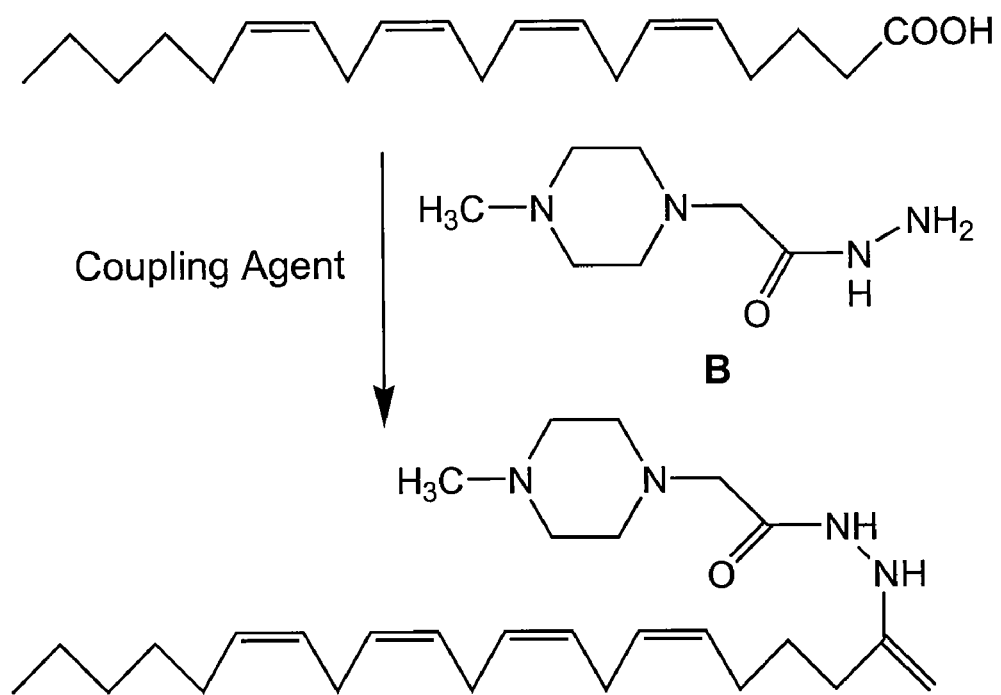

In some embodiments, the labeling reagents can have the general structure A or B as illustrated in FIG. 2. Labeling reagents of general structures A and B can be reacted with analytes to form structures A" and B" as illustrated in FIG. 3. In some embodiments, the labeled analytes can be fragmented in a mass spectrometer. Some possible fragments and their respective masses can be found in FIG. 3. Two possible sets of isobaric labeling reagents of general structure A and B can be found in FIG. 4a, with the possible reporter ions illustrated in FIG. 4b. Two sets of mass differential tags based upon general structures A and B can be found in FIGS. 5a and 5b. FIG. 6a and FIG. 6b illustrate the labeling of an analyte using labeling reagents of general structure A and B.

The Reactive Group:

The reactive group (sometimes represented by use of the shorthand "RG") of the labeling reagent or reagents used in the method, mixture, kit and/or composition embodiments can be a nucleophilic group that is capable of reacting with one or more functional groups of one or more reactive analytes of a sample. It is to be understood that in some embodiments, the reactive group may be considered to include an atom or group associated with the linker (balance).

It is to be understood that when the reactive group is represented by some of the specific moieties discussed below, the analyte may be linked to the linker (balance) through one or more additional atoms or groups that may, or may not, be considered to be part of the linker (balance).

The reactive group can be preexisting or it can be prepared in-situ. In-situ preparation of the reactive group can proceed in the absence of the reactive analyte or it can proceed in the presence of the reactive analyte. In some embodiments, the reactive group can be generated in-situ by the in-situ removal of a protecting group. Consequently, any existing or newly created reagent or reagents that can effect the derivatization of analytes by the reaction of nucleophiles and/or electrophiles are contemplated by the method, mixture, kit and/or composition embodiments of this invention.

Where the reactive group of the labeling reagent is a nucleophile, it can react with a suitable electrophilic group of the analyte or analytes. Numerous pairs of suitable nucleophilic groups and electrophilic groups are known and often used in the chemical and biochemical arts. Non-limiting examples of reagents comprising suitable nucleophilic groups that can be coupled to analytes (e.g. such as biologically important carboxy acid compounds (e.g., prostaglandins, fatty acids, carnitines, etc.), proteins, peptides, carbohydrates, lipids, steroids or other small molecules having a mass of less that 1500 daltons) to effect their derivatization, are described in the Pierce Life Science & Analytical Research Products Catalog & Handbook (a Perstorp Biotec Company), Rockford, Ill. 61105, USA. Other suitable reagents are well known in the art and are commercially available from numerous other vendors such as Sigma-Aldrich.

In some embodiments, the reactive group of the labeling reagent can be a nucleophile such as an amine group or hydrazine group. In some embodiments, the nucleophilic reactive group can be an aminoalkyl group or alkyl hydrazine group.

The Reporter Moiety:

The reporter moiety (sometimes represented by use of the shorthand "RP") of the labeling reagent or reagents used in embodiments of this invention can be a group that has a unique mass (or mass to charge ratio in a mass spectrometer) that can be determined. Accordingly, in some embodiments, each reporter moiety of a set of isomeric and/or isobaric labeling reagents has a unique gross mass, and its corresponding signature ion, is different for each labeling reagent of the set.

Different reporter moieties can comprise one or more heavy atom isotopes to achieve their unique gross mass. For example, isotopes of carbon ($^{12}C$, $^{13}C$ and $^{14}C$), nitrogen ($^{14}N$ and $^{15}N$), oxygen ($^{16}O$ and $^{18}O$), sulfur ($^{32}S$ and $^{34}S$) or hydrogen (hydrogen, deuterium and tritium) exist and can be used in the preparation of a diverse group of reporter moieties. These are not limiting as other light and heavy atom isotopes can also be used in the reporter moieties. Basic starting materials suitable for preparing reporter moieties comprising light and heavy atom isotopes are available from various commercial sources such as Cambridge Isotope Laboratories, Andover, Mass. (See: list of "basic starting materials" at www.isotope.com) and Isotec (a division of Sigma-Aldrich). Cambridge Isotope Laboratories and Isotec will also prepare desired compounds under custom synthesis contracts. Id.

The reporter moiety can either comprise a fixed charge or can become ionized during the analysis process. Because the reporter moiety can either comprises a fixed charge or can become ionized, the labeling reagent might be isolated or be used to label the reactive analyte in a salt (or a mixture of salts) or zwitterionic form. Ionization of the reporter moiety (or reporter ion) facilitates its determination in a mass spectrometer. Accordingly, the presence of the reporter moiety in a labeled analyte can be determined as a fragment ion, sometimes referred to as a signature ion (or reporter ion).

When ionized, the signature ion (i.e. reporter ion) can comprise one or more net positive or negative charges. Thus, the reporter ion can comprise one or more acidic groups and/or basic groups since such groups can be easily ionized in a mass spectrometer. For example, the reporter moiety can comprise one or more basic nitrogen atoms (positive charge) and/or one or more ionizable acidic groups such as a carboxylic acid group, sulfonic acid group or phosphoric acid group (negative charge) provided that on balance there are more of one or the other of the basic or acidic groups such that the reporter moiety produces a reporter ion comprising a net positive or negative charge. Non-limiting examples of reporter moieties comprising at least one basic nitrogen include substituted or unsubstituted morpholine, piperidine or piperazine containing compounds.

A unique reporter moiety can be associated with a sample of interest thereby labeling one or multiple analytes of that sample with said unique reporter moiety. In this way information about the unique reporter moiety (generally detected as a signature ion (i.e. reporter ion) in a mass spectrometer) can be associated with information about one or all of the analytes of said sample.

However, the unique reporter moiety need not be physically linked to an analyte when the signature ion is determined. Rather, the unique gross mass of the signature ion can, for example, be determined in a second mass analysis of a tandem mass analyzer, after ions of the labeled analyte are fragmented to thereby produce daughter fragment ions and signature ions.

The determined signature ion(s) can be used to identify the sample from which a determined analyte originated. Further, the amount (often expressed as a concentration and/or quantity) of the unique signature ion, either relative to the amount of other signature ions or relative to the signature ion associated with a calibration standard (e.g. an analyte expected in the sample and labeled with a specific reporter moiety), can be used to determine the relative and/or absolute amount (often expressed as a concentration and/or quantity) of analyte in the sample or samples (such as those used to form a sample mixture). In some embodiments, rather than using an internal calibration standard, absolute quantification can be determined based on comparison of the peak intensities of the various signature ions with a calibration curve. Therefore information, such as the amount of one or more analytes in a particular sample, can be associated with the reporter moiety that is used to label each particular sample. Where the identity of the analyte or analytes is also determined, that information can be correlated with information pertaining to the different signature ions to thereby facilitate the determination of the identity and amount of each labeled analyte in one sample or in a plurality of samples.

In some embodiments, the reporter moiety can comprise a nitrogen atom covalently linked to the methylene carbon of a substituted or unsubstituted N-alkylated acetic acid moiety wherein the substituted or unsubstituted methylene carbon but not the carbonyl group of the carboxylic acid (or thiocarboxylic acid) group of the acetic acid moiety is part of the reporter. Thus, in some embodiments, the carboxylic acid (or thio carboxylic acid) group can be used to link the reporter to the linker but it is not considered part of the reporter. The nitrogen atom can be alkylated with one, two or three groups. For example, the moiety comprising the nitrogen atom can be a substituted primary amine such as a methyl, ethyl or propyl group or a substituted secondary amine such as dimethylamine, diethylamine, di-n-propylamine or diisopropylamine. Thus, for example the reporter moiety "RP" can be illustrated by formulas $X^1$, $X^2$, $X^3$, $X^4$, $X^5$, $X^6$, $X^7$, $X^8$ or $X^9$ as follows wherein the reporter moiety "RP" is set off by the bracket:

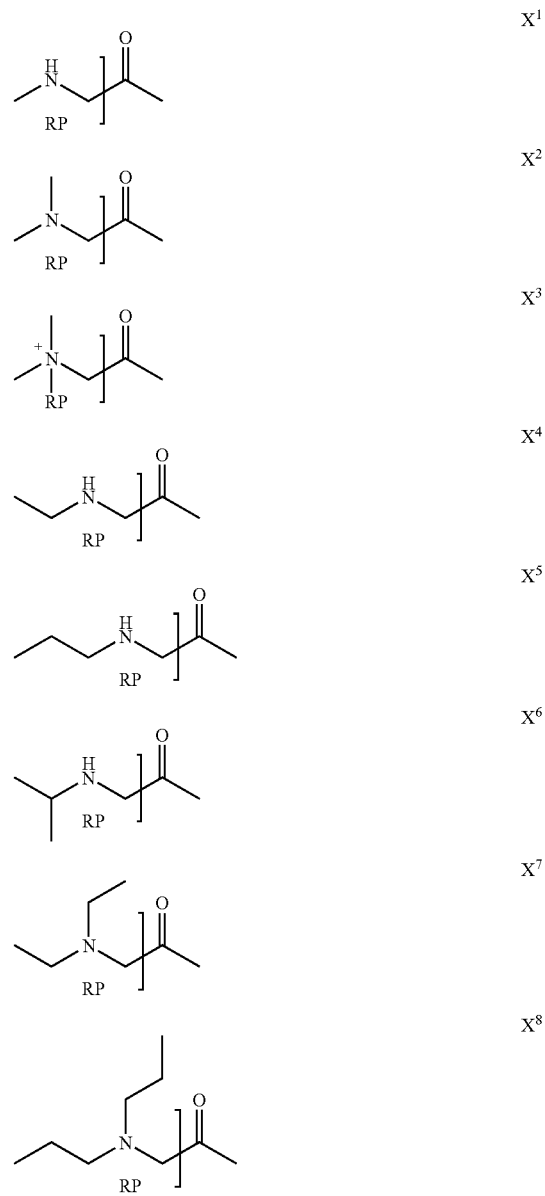

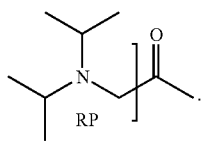

$X^9$

The reporter moiety can be a 5, 6 or 7 membered heterocyclic ring comprising a ring nitrogen atom covalently linked to the methylene carbon of a substituted or unsubstituted N-alkylated acetic acid moiety to which the analyte is (directly or indirectly) linked through the carbonyl carbon of the N-alkyl acetic acid moiety and wherein the substituted or unsubstituted methylene carbon but not the carbonyl group of carboxylic acid group is part of the reporter. The heterocyclic ring can be aromatic or non-aromatic. Thus, the reporter moiety can be represented by formula Y-J- wherein the group Y can represent the 5, 6 or 7 membered heterocyclic ring and the group J can represent the substituted or unsubstituted methylene group of the substituted or unsubstituted acetic acid moiety. The heterocyclic ring can be substituted or unsubstituted. For example, substituents of the heterocyclic moiety can include alkyl, alkoxy and/or aryl groups. The substituents can comprise protected or unprotected groups, such as amine, hydroxyl or thiol groups, suitable for linking the analyte to a support (See FIG. 6). The heterocyclic ring can comprise additional heteroatoms such as one or more silicon, nitrogen, oxygen and/or sulfur atoms. Thus, for example the reporter moiety "RP" can be illustrated by formulas $X^{10}$, $X^{11}$, $X^{12}$, $X^{13}$, $X^{14}$, $X^{15}$, $X^{16}$, $X^{17}$, $X^{18}$, $X^{19}$, $X^{20}$, $X^{21}$, $X^{22}$, $X^{23}$, $X^{24}$, $X^{25}$ or $X^{26}$ as follows wherein the reporter moiety "RP" is set off by the bracket:

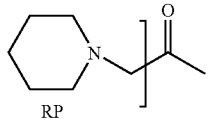

$X^{10}$

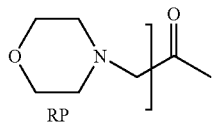

$X^{11}$

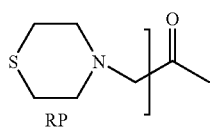

$X^{12}$

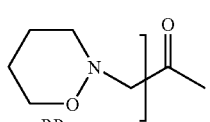

$X^{13}$

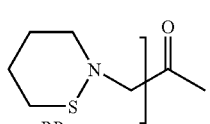

$X^{14}$

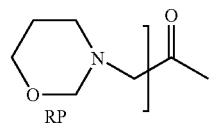

$X^{15}$

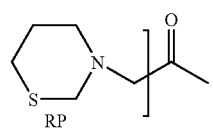

$X^{16}$

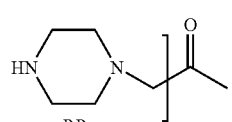

$X^{17}$

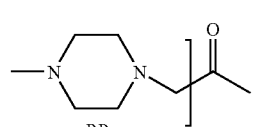

$X^{18}$

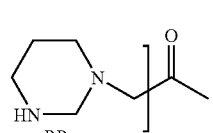

$X^{19}$

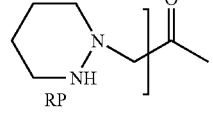

$X^{20}$

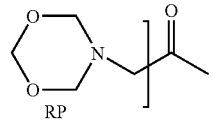

$X^{21}$

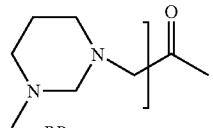

$X^{22}$

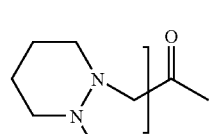

$X^{23}$

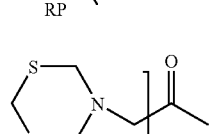

$X^{24}$

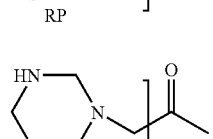

$X^{25}$

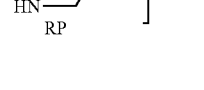

-continued

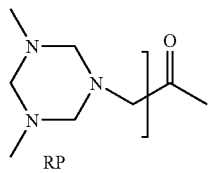

$X^{26}$

The reporter moiety can be selected so that it does not substantially sub-fragment under conditions typical for the analysis of the analyte. For the avoidance of any doubt, this is an optional, not a required, feature. For example, the reporter can be chosen so that it does not substantially sub-fragment under conditions of dissociative energy applied to cause fragmentation of the labeled analyte in a mass spectrometer. By "does not substantially sub-fragment" we mean that fragments of the reporter are difficult or impossible to detect above background noise when applied to the successful determination of the labeled analyte.

In some embodiments, the gross mass of a reporter ion can be intentionally selected to be different as compared with the mass of the analyte sought to be determined or the mass of any of the expected fragments of the analyte (i.e. a "quiet zone"). For example, where proteins or peptides are the analytes, the gross mass of the reporter ion can be chosen to be different as compared with any naturally occurring amino acid or peptide, or expected fragment ion thereof. This can facilitate analyte determination since, depending on the analyte, the lack of any possible components of the sample having the same coincident mass can add confidence to the result of any analysis. Examples of mass ranges where little background can be expected for peptides can be found in Table 1.

TABLE 1

Possible "Quiet Zones" For Selection Of Label Fragment Ion m/z Associated With Peptide Analysis
M/z start-end

| |
|---|
| 10-14 |
| 19-22 |
| 24-26 |
| 31-38 |
| 40-40 |
| 46-50 |
| 52-52 |
| 58-58 |
| 61-69 |
| 71-71 |
| 74-83 |
| 89-97 |
| 103-109 |
| 113-119 |
| 121-125 |
| 128-128 |
| 131-135 |
| 137-147 |
| 149-154 |
| 156-156 |
| 160-174 |
| 177-182 |
| 184-184 |
| 188-189 |
| 191-191 |
| 202-207 |
| 210-210 |
| 216-222 |
| 224-226 |

The reporter moiety can be non-polymeric. The reporter moiety can be selected to produce a signature ion of m/z that indicates its mass is less than 250 atomic mass units (amu). The reporter moiety can be selected to produce a signature ion of m/z less than 200 amu. The reporter moiety can be selected to produce a signature ion of m/z less than 150 amu. Such a small molecule can be easily determined in the second mass analysis, free from other components of the sample having the same coincident mass in the first mass analysis. In this context, the second mass analysis can be performed, typically in a tandem mass spectrometer (or, for example by post source decay in a single stage instrument), on selected ions that are determined in the first mass analysis. Because ions of a particular mass to charge ratio can be specifically selected out of the first mass analysis for possible fragmentation and further mass analysis, the non-selected ions from the first mass analysis are not carried forward to the second mass analysis and therefore do not contaminate the spectrum of the second mass analysis. Furthermore, the sensitivity of a mass spectrometer and the linearity of the detector (for purposes of quantification) can be quite robust in this low mass range. Additionally, the present state of mass spectrometer technology can allow for baseline mass resolution of less than one Dalton in this mass range. For all these reasons, reporters possessing the above described characteristics can provide quite accurate quantification of determined analytes from complex mixtures utilizing methods as described herein.

The Balance (or Linker) Moiety:

The balance (or linker) moiety (sometimes referred to by use of the shorthand "LK") of the labeling reagent or reagents that can be used with embodiments of this invention links the reporter moiety to the analyte or the reporter moiety to the reactive group depending on whether or not a reaction with the analyte has occurred. The linker can be selected to produce a neutral species (i.e. undergo neutral loss in a mass spectrometer) wherein both the bond that links the linker to the reporter moiety (the RL bond) and the bond that links the linker to the analyte (the LA bond) fragment in a mass spectrometer. The linker can be designed to sub-fragment when subjected to dissociative energy, including sub-fragmentation to thereby produce only neutral fragments of the linker. The linker can be designed to produce one or more detectable fragments.

With respect to isobaric sets of reagents, the linker moiety can comprise one or more heavy atom isotopes such that its mass compensates for the difference in gross mass between the reporter moieties for each labeled analyte of a mixture or for the labeling reagents of set and/or kit. Moreover, the aggregate gross mass (i.e. the gross mass taken as a whole) of the reporter/linker combination (i.e. the reporter/linker moiety) can be the same for each labeled analyte of a mixture or for the labeling reagents of set and/or kit. More specifically, the linker moiety can compensate for the difference in gross mass between reporter moieties of labeled analytes from different samples (each sample being labeled with a different reagent of the isobaric set) wherein the unique gross mass of the reporter moiety correlates with the sample from which the labeled analyte originated and the aggregate gross mass of the reporter/linker combination is the same for each labeled analyte of a sample mixture regardless of the sample from which it originated. In this way, the gross mass of identical analytes in two or more different samples can have the same gross mass when labeled and then mixed to produce a sample mixture.

Figure 4A:
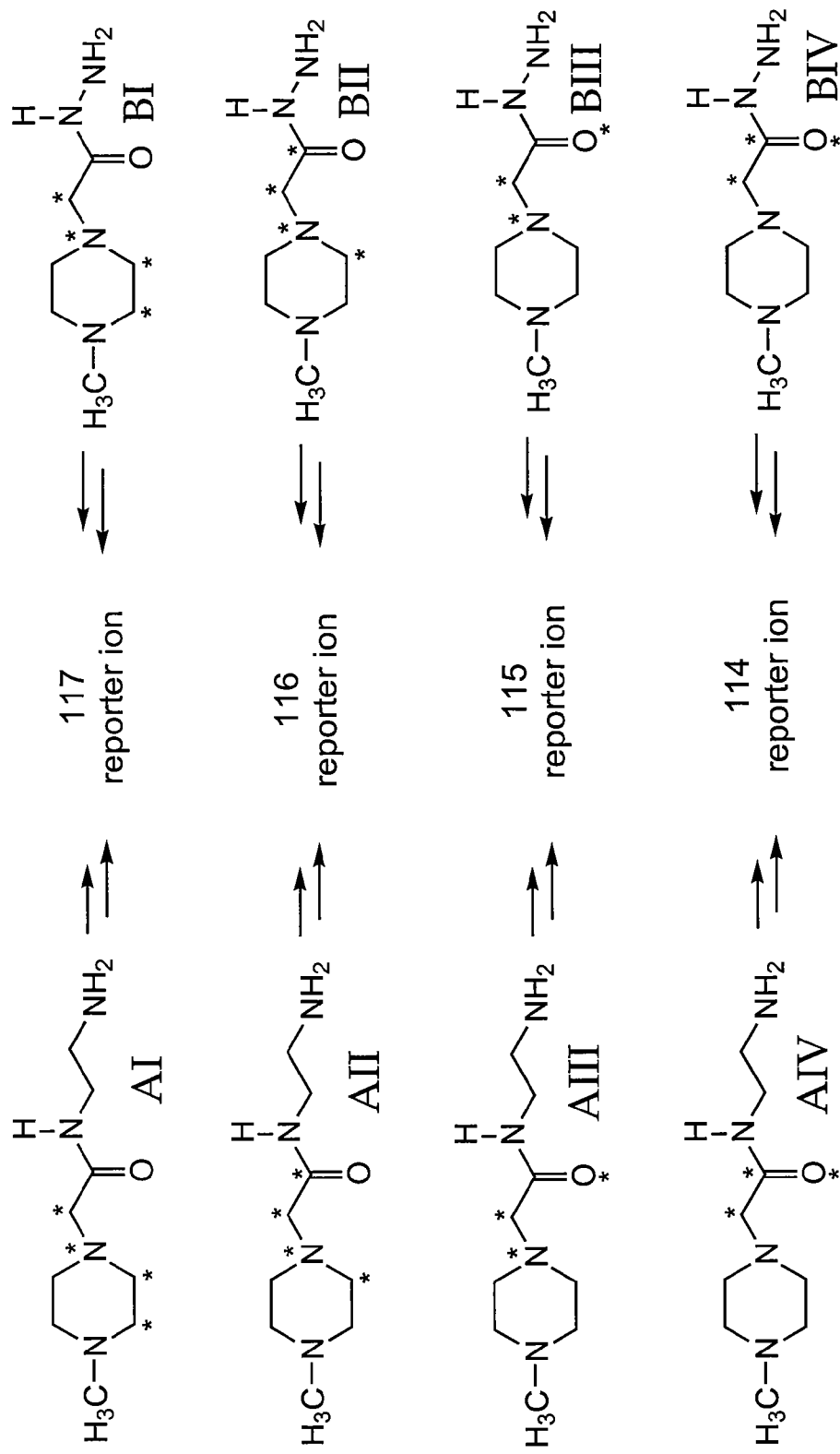
FIG. 4a is an illustration of two possible sets of isobaric labeling reagents (based upon structure A and structure B, respectively) each of which produces the same reporter ion set.
Figure 4B:
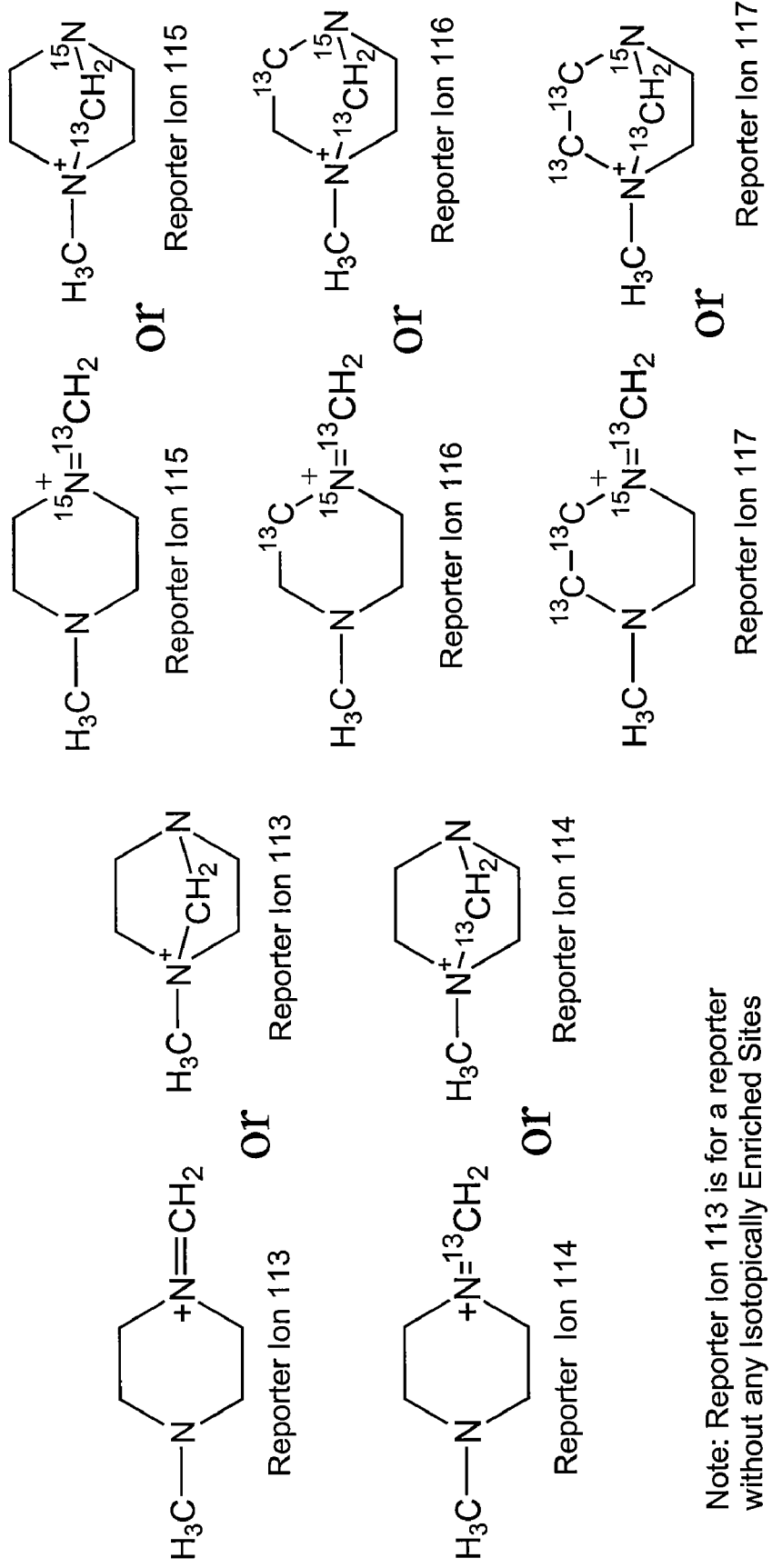
FIG. 4b is an illustration of possible structures for the reporter ions 114-117 mentioned in FIG. 4a as well as the possible structures for the non-encoded (i.e. "cold") reporter ion 113.

For example, the labeled analytes, or the labeling reagents of a set and/or kit for labeling the analytes, can be isobars. Thus, if ions of a particular mass to charge ratio (taken from the sample mixture) are selected (i.e. selected ions) in a mass spectrometer from an initial mass analysis of the sample mixture, identical analytes from the different samples that make up the sample mixture can be represented in the selected ions in proportion to their respective concentration and/or quantity in the sample mixture. Accordingly, the linker not only links the reporter to the analyte, it also can serve to compensate for the differing masses of the unique reporter moieties to thereby harmonize the gross mass of the reporter/linker moiety in the labeled analytes of the various samples (c.f. FIG. 4a and the two sets of isobaric labeling reagents illustrated therein).

Because the linker can act as a mass balance for the reporter moieties in the labeling reagents greater the number of atoms in the linker, the greater the possible number of different isomeric/isobaric labeling reagents of a set and/or kit. Stated differently, generally the greater the number of atoms that a linker comprises, the greater number of potential reporter/linker combinations exist since isotopes can be substituted at most any position in the linker to thereby produce isomers and/or isobars of the linker portion wherein the linker portion is used to offset the differing masses of the reporter portion and thereby create a set of unique isobaric and/or mass differential labeling reagents. Such diverse sets of labeling reagents are particularly well suited for multiplex analysis of analytes in the same and/or different samples.

The total number of labeling reagents of a set and/or kit can be two, three, four, five, six, seven, eight, nine, ten, eleven, twelve, thirteen, fourteen, fifteen, sixteen, fifteen, sixteen, seventeen, eighteen, nineteen, twenty or more. The diversity of the labeling reagents of a set or kit is limited only by the number of atoms of the reporter and linker moieties, the heavy atom isotopes available to substitute for the light isotopes and the various synthetic configurations in which the isotopes can be synthetically placed. As suggested above however, numerous isotopically enriched basic starting materials are readily available from manufacturers such as Cambridge Isotope Laboratories and Isotec. Such isotopically enriched basic starting materials can be used in the synthetic processes used to produce sets of isobaric and mass differential labeling reagents (i.e. labeling reagents of different gross mass) or be used to produce the isotopically enriched starting materials that can be used in the synthetic processes used to produce sets of isobaric and mass differential labeling reagents.

In some embodiments, the labeling reagents comprise a set of mass differential tags. For these sets, the linker moiety optionally won't comprise any heavy atom isotopes since the linker typically is not be used to 'balance' the different reporters. In this way, each different reagent of the set has a unique mass and a unique reporter moiety that can produce a unique signature ion in the mass spectrometer when cleaved from the labeled analyte.

Some examples of the preparation of labeling reagents suitable for use in a set of labeling reagents are discussed in more detail below. For example, a linker moiety can be represented by formula I#;

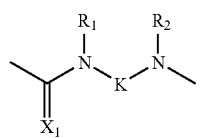

wherein the atoms or groups represented by $X_1$, $K$, $R_1$ and $R_2$ are described in more detail below.

The Reporter/Linker Combination (i.e. the Reporter/Linker Moiety):

The labeling reagents can comprise reporter moieties and linker moieties that are linked directly to each other. As described above, in some embodiments the reporter/linker moiety can be identical in gross mass for each member of a set and/or kit of labeling reagents (i.e. for isobaric sets of reagents). Moreover, the bond that links the reporter moiety to the linker moiety can be designed to fragment, in at least a portion of the selected ions, when subjected to dissociative energy thereby releasing the reporter ion from the linker moiety and/or linker/analyte moiety (true whether or not the set of reagents is isobaric). Accordingly, the gross mass of the reporter ion (observed as a m/z ratio in the mass spectrometer) and its intensity can be observed directly in MS/MS analysis.

The reporter/linker moiety can comprise various combinations of the same or different heavy atom isotopes amongst the various labeling reagents of a set or kit. In the scientific literature this has sometimes been referred to as "coding", "isotope coding" or simply as "encoding". For example, Abersold et al. has disclosed the isotope coded affinity tag (ICAT; see WO00/11208). In one respect, the reagents of Abersold et al. differ from some of the labeling reagents of this invention in that Abersold does not teach two or more same mass labeling reagents such as isomeric and/or isobaric labeling reagents. Rather, Abersold et al. teach about "light" and "heavy" versions of their labeling reagents. With respect to the mass differential labeling reagents disclosed herein, the reagents of Abersold do not fragment in the mass spectrometer to release signature ions that can be observed with the fragment (daughter) ions of the analyte. Thus, unlike the Abersold reagents, the mass differential reagents disclosed herein permit identification and quantification of an analyte by analysis of a single MS/MS spectrum or single data set suitable to prepare said spectrum.

In some embodiments, the reporter and/or linker moieties can comprise an atom or group that can be used to immobilize the labeling reagent or labeled analyte to a support. Immobilization can be direct or indirect. For example, direct immobilization can occur if an atom or group (e.g. an alkyl amine substituent of the reporter and/or linker) associated with the reporter and/or linker can, in some embodiments, interact directly with a reactive group (e.g. a cleavable linker) of the support to effect mobilization. By comparison, indirect immobilization occurs if, for example, a substituent of the reporter and/or linker (e.g. an alkylamine substituent of the reporter and/or linker) is modified (e.g. is biotinylated) and the modifying group interacts with a reactive group of the support (e.g. avidin or streptavidin) to effect immobilization. Consequently, this invention contemplates embodiments wherein the analytes can be reacted with support bound labeling reagents wherein each support comprises a unique labeling reagent such that different samples are reacted with different supports as well as embodiments where each different sample is reacted with a different labeling reagent and the reaction products are thereafter immobilized to the same or to different supports. In either case, a sample mixture is generally obtained by cleaving the labeled analytes from the support(s) for analysis by mass spectrometry.

Mass Spectrometers/Mass Spectrometry (MS):

The methods of this invention can be practiced using tandem mass spectrometers and other mass spectrometers that have the ability to select and fragment molecular ions. Tandem mass spectrometers (and to a lesser degree single-stage mass spectrometers) have the ability to select and fragment molecular ions according to their mass-to-charge (m/z) ratio, and then record the resulting fragment (daughter) ion spectra.

More specifically, daughter fragment ion spectra can be generated by subjecting selected ions to dissociative energy (e.g. collision-induced dissociation (CID)). For example, ions corresponding to labeled peptides of a particular m/z ratio can be selected from a first mass analysis, fragmented and reanalyzed in a second mass analysis. Representative instruments that can perform such tandem mass analysis include, but are not limited to, magnetic four-sector, tandem time-of-flight, triple quadrupole, ion-trap, and hybrid quadrupole time-of-flight (Q-TOF) mass spectrometers.

These types of mass spectrometers may be used in conjunction with a variety of ionization sources, including, but not limited to, electrospray ionization (ESI) and matrix-assisted laser desorption ionization (MALDI). Ionization sources can be used to generate charged species for the first mass analysis where the analytes do not already possess a fixed charge. Additional mass spectrometry instruments and fragmentation methods include post-source decay in MALDI-MS instruments and high-energy CID using MALDI-TOF(time of flight)-TOF MS. For a recent review of tandem mass spectrometers please see: R. Aebersold and D. Goodlett, *Mass Spectrometry in Proteomics. Chem. Rev.* 101: 269-295 (2001).

Fragmentation by Dissociative Energy:

It is well accepted that bonds can fragment as a result of the processes occurring in a mass spectrometer. Moreover, bond fragmentation can be induced in a mass spectrometer by subjecting ions to dissociative energy. For example, the dissociative energy can be produced in a mass spectrometer by collision-induced dissociation (CID). Other non-limiting examples of dissociative energy that can be used to fragment ions in a mass spectrometer include, but are not limited to, collision activated dissociation (CAD), photoinduced dissociation (PID)), surface induced dissociation (SID)), electron induced dissociation (EID), electron capture dissociation (ECD)), thermal/black body infrared radiative dissociation (BIRD), post source decay, or combinations thereof. Those of ordinary skill in the art of mass spectrometry can appreciate that other exemplary techniques for imposing dissociative energy that cause fragmentation include, but are not limited to, photo dissociation, electron capture and surface induced dissociation.

The process of fragmenting bonds by collision-induced dissociation involves increasing the kinetic energy state of selected ions, through collision with an inert gas, to a point where bond fragmentation occurs. For example, kinetic energy can be transferred by collision with an inert gas (such as nitrogen, helium or argon) in a collision cell. The amount of kinetic energy that can be transferred to the ions is proportional to the number of gas molecules that are allowed to enter the collision cell. When more gas molecules are present, a greater amount of kinetic energy can be transferred to the selected ions, and less kinetic energy is transferred when there are fewer gas molecules present.

It is therefore clear that the application of dissociative energy in a mass spectrometer can be controlled. It is also well accepted that certain bonds are more labile than other bonds. The lability of the bonds in an analyte or the reporter/linker/non-encoded detectable label moiety depends upon the nature of the analyte and the nature of the reporter/linker/non-encoded detectable label moiety. Accordingly, the dissociative energy can be adjusted so that the analytes and/or the labeling reagents (e.g. the reporter/linker combinations) can be fragmented in a manner that is determinable. One of skill in the art will appreciate how to make such routine adjustments to the components of a mass spectrometer to thereby achieve the appropriate level of dissociative energy to thereby fragment at least a portion of ions of labeled analytes into signature ions (i.e. reporter ions) and daughter fragment ions.

For example, dissociative energy can be applied to ions that are selected/isolated from the first mass analysis. In a tandem mass spectrometer, the extracted ions can be subjected to dissociative energy, to thereby cause fragmentation, and then transferred to a second mass analyzer. The selected ions can have a selected mass to charge ratio. The mass to charge ratio can be within a range of mass to charge ratios depending upon the characteristics of the mass spectrometer. When collision induced dissociation is used, the ions can be transferred from the first to the second mass analyzer by passing them through a collision cell where the dissociative energy can be applied to thereby produce fragment ions. For example the ions sent to the second mass analyzer for analysis can include some, or a portion, of the remaining (unfragmented) selected ions (if any), as well as reporter ions (signature ions) and daughter fragment ions of the labeled analyte.

Analyte Determination By Computer Assisted Database Analysis:

In some embodiments, analytes can be determined based upon daughter-ion fragmentation patterns that are analyzed by computer-assisted comparison with the spectra of known or "theoretical" analytes. For example, the daughter fragment ion spectrum of a peptide ion fragmented under conditions of low energy CID can be considered the sum of many discrete fragmentation events. The common nomenclature differentiates daughter fragment ions according to the amide bond that breaks and the peptide fragment that retains charge following bond fission (Reopstorff et al., *Biomed. Mass Spectrom.*, 11: 601 (1988)). Charge-retention on the N-terminal side of the fissile amide bond results in the formation of a b-type ion. If the charge remains on the C-terminal side of the broken amide bond, then the fragment ion is referred to as a y-type ion. In addition to b- and y-type ions, the CID mass spectrum may contain other diagnostic fragment ions (these include ions generated by neutral loss of ammonia (−17 amu) from glutamine, lysine and arginine or the loss of water (−18 amu) from hydroxyl-containing amino acids such as serine and threonine); the diagnostic fragment ions as well as the b- and y-type ions all being daughter fragment ions. Certain amino acids have been observed to fragment more readily under conditions of low-energy CID than others. This is particularly apparent for peptides containing proline or aspartic acid residues, and even more so at aspartyl-proline bonds (Mak, M. et al., *Rapid Commun. Mass Spectrom.*, 12: 837-842 (1998)). Accordingly, the peptide bond of a Z'''-pro dimer or Z'''-asp dimer, wherein Z''' is any natural amino acid, pro is proline and asp is aspartic acid, will tend to be more labile as compared with the peptide bond between all other amino acid dimer combinations.

For peptide and protein samples therefore, low-energy CID spectra contain redundant sequence-specific information in overlapping b- and y-series ions, internal fragment ions from the same peptide, and immonium and other neutral-loss ions. Interpreting such CID spectra to assemble the amino acid sequence of the parent peptide de novo is challenging and time-consuming but can be done. Recent advances in computer assisted de novo methods for sequencing are were described in Huang, Y., Ross, P, Smirnov, I, Martin, S, and Pappin, D. 2003, Proceedings of 6th International Symposium on MS in Health and Life Sciences, Aug. 24-28, 2003, San Francisco Calif. The most significant advances in identifying peptide sequences have been the development of computer algorithms that correlate peptide CID spectra with peptide sequences that already exist in protein and DNA sequence databases. Such approaches are exemplified by programs such as SEQUEST (Eng, J. et al. *J. Am. Soc. Mass Spectrom.*, 5: 976-989 (1994)) and MASCOT (Perkins, D. et al. *Electrophoresis*, 20: 3551-3567 (1999)).

In brief, experimental peptide CID spectra (MS/MS spectra) are matched or correlated with 'theoretical' daughter fragment ion spectra computationally generated from peptide sequences obtained from protein or genome sequence databases. The match or correlation is based upon the similarities between the expected mass and the observed mass of the daughter fragment ions in MS/MS mode. The potential match or correlation is scored according to how well the experimental and 'theoretical' fragment patterns coincide. The constraints on databases searching for a given peptide amino acid sequence are so discriminating that a single peptide CID spectrum can be adequate for identifying any given protein in a whole-genome or expressed sequence tag (EST) database. For other reviews please see: Yates, J. R. Trends, Genetics, 16: 5-8 (2000) and Yates, J. R., *Electrophoresis* 19: 893-900 (1998).

Accordingly, daughter fragment ion analysis of MS/MS spectra can be used not only to determine the analyte of a labeled analyte, it can also be used to determine analytes from which the determined analyte originated. For example, identification of a peptide in the MS/MS analysis can be can be used to determine the protein from which the peptide was cleaved as a consequence of an enzymatic digestion of the protein. It is envisioned that such analysis can be applied to other analytes, such as nucleic acids, lipids steroids and/or prostaglandins.

The RL Bond and the LA Bond:

The bond between an atom of the reporter moiety and an atom of the linker moiety is the RL bond. The bond between an atom of the linker moiety and an atom of the analyte is the LA bond. In some embodiments, the RL bond and the LA bond can fragment, in at least a portion of selected ions, when subjected to dissociative energy levels. Therefore, the dissociative energy level can, in some embodiments, be adjusted in a mass spectrometer so that both the RL bond and the LA bond fragment in at least a portion of the selected ions of the labeled analytes.

Fragmentation of the RL bond releases the reporter moiety from the analyte so that the reporter ion can be determined independently from the analyte. Fragmentation of LA bond releases the reporter/linker moiety from the analyte, or the linker from the analyte, depending on whether or not the RL bond has already fragmented. In some embodiments, the RL bond can be more labile than the LA bond. In some embodiments, the LA bond can be more labile than the RL bond. In some embodiments, the RL and LA bonds can be of the same relative lability. Stated briefly, the RL bond is designed to fragment to thereby release the reporter ion but the LA bond may, or may not, fragment in the various embodiments of this invention.

In some embodiments, when the analyte of interest is a protein or peptide, the relative lability of the RL and LA bonds can be adjusted with regard to an amide (peptide) bond. The RL bond, the LA bond or both bonds RL and LA can be more, equal or less labile as compared with a typical amide (peptide) bond. For example, under conditions of dissociative energy, the RL bond and/or the LA bond can be less prone to fragmentation as compared with the peptide bond of a Z'''-pro dimer or Z'''-asp dimer, wherein Z''' is any natural amino acid, pro is proline and asp is aspartic acid. In some embodiments, the RL bond and the LA bond can fragment with approximately the same level of dissociative energy as a typical amide bond. In some embodiments, the RL and LA bonds can fragment at a greater level of dissociative energy as compared with a typical amide bond.

In some embodiments, the RL bond and the LA bond can exist such that fragmentation of the RL bond results in the fragmentation of the LA bond, and vice versa. In this way, both bonds RL and LA can fragment essentially simultaneously such that no substantial amount of analyte, or daughter fragment ion thereof, comprises a partial label. By "substantial amount of analyte" it is meant that less than 25%, and preferably less than 10%, of partially labeled analyte can be determined in the mass spectrometer (e.g. in MS/MS analysis).

Because in some embodiments there can be a clear demarcation between labeled and unlabeled fragments of the analyte in the mass spectra (e.g. in MS/MS analysis), this feature can simplify the identification of the analytes from computer assisted analysis of the daughter fragment ion spectra since no compensation for the remnants of the label need be applied to the mass calculations used to analyze the daughter fragment ions of an analyte. Moreover, because the fragment ions of analytes can, in some embodiments, be either fully labeled or unlabeled (but not partially labeled), there can be little or no scatter in the masses of the daughter fragment ions caused by isotopic distribution across fractured bonds such as would be the case where isotopes were present on each side of a single labile bond of a partially labeled analyte resulting from fragmentation of the labeled analyte caused by the application of dissociative energy levels.

The Labeling of Analytes:

As discussed previously, analytes can be labeled by reacting a functional group of the analyte with the reactive group of the labeling reagent. The functional group on the analyte can be an electrophilic group and the functional group of the labeling reagent can be a nucleophilic group. The electrophile and nucleophile can react to form a covalent link between the analyte and the labeling reagent.

The labeling reaction can take place in solution. In some embodiments, one of the analyte or the labeling reagent can be support bound. The labeling reaction can sometimes be performed in aqueous conditions. Aqueous conditions can be selected for the labeling of biomolecules such as proteins, peptides and/or nucleic acids. The labeling reaction can sometimes be performed in organic solvent or a mixture of organic solvents. Organic solvents can be selected for analytes that are small molecules. Mixtures of water and organic solvent or organic solvents can be used across a broad range. For example, a solution of water and from about 5 percent to about 95 percent organic solvent or solvents (v/v) can be prepared and used for labeling the analyte. In some embodiments, a solution of water and from about 50 percent to about 95 percent organic solvent or solvents (v/v) can be prepared and used for labeling the analyte. In some embodiments, a solution of water and from about 65 percent to about 80 percent organic solvent or solvents (v/v) can be prepared and used for labeling the analyte. Non-limiting examples of organic solvents include N,N'-dimethylformamide (DMF), acetonitrile (ACN), N-Methyl pyrrolidine (NMP) and alcohols such as methanol, ethanol, propanol and/or butanol. Those of skill in the art will be able to determine appropriate solvent conditions to facilitate analyte labeling depending upon the nature of the labeling reagent and the nature of the analyte using no more than knowledge available in the art and the disclosure provided herein in combination with routine experimentation.

When performing a labeling reaction, the pH can be modulated. The pH can be in the range of 4-10. The pH can be outside this range. Generally, the basicity of non-aqueous reactions can be modulated by the addition of non-nucleophilic organic bases. Non-limiting examples of suitable bases include N-methylmorpholine, triethylamine and N,N-diisopropylethylamine. Alternatively, the pH of water containing solvents can be modulated using biological buffers such as (N-[2-hydroxyethyl]piperazine-N'-[2-ethanesulfonic acid) (HEPES) or 4-morpholineethane-sulfonic acid (MES) or inorganic buffers such as sodium carbonate and/or sodium bicarbonate. Because at least one of the reactive groups can be electrophilic, it can be desirable to select the buffer to not contain any nucleophilic groups. Those of skill in the art will, with the application of ordinary experimentation, be able to identify other buffers that can be used to modulate the pH of a labeling reaction so as to facilitate the labeling of an analyte with a labeling reagent. Accordingly, those of skill in the art will be able to determine appropriate conditions of solvent and pH to thereby facilitate analyte labeling depending upon the nature of the labeling reagent and the nature of the analyte using no more than the disclosure provided herein in combination with routine experimentation.

Sample Processing:

In certain embodiments of this invention, a sample can be processed prior to, as well as after, labeling of the analyte or analytes. Processing can facilitate the labeling of the analyte or analytes. The processing can facilitate the analysis of the sample components. Processing can simplify the handling of the samples. Processing can facilitate two or more of the foregoing.

For example, a sample can be treated with an enzyme or a chemical. The enzyme can be a protease (to degrade proteins and peptides), a nuclease (to degrade nucleic acids) or some other enzyme. The enzyme can be chosen to have a very predictable degradation pattern. Two or more proteases and/or two or more nuclease enzymes may also be used together, or with other enzymes, to thereby degrade sample components.

For example, the proteolytic enzyme trypsin is a serine protease that cleaves peptide bonds between lysine or arginine and an unspecific amino acid to thereby produce peptides that comprise an amine terminus (N-terminus) and lysine or arginine carboxyl terminal amino acid (C-terminus). In this way the peptides from the cleavage of the protein are predictable and their presence and/or quantity, in a sample from a trypsin digest, can be indicative of the presence and/or quantity of the protein of their origin. Moreover, the free amine termini of a peptide can be a good nucleophile that facilitates its labeling. Other exemplary proteolytic enzymes include papain, pepsin, ArgC, LysC, V8 protease, AspN, pronase, chymotrypsin and carboxypeptidase (e.g. carboxypeptidase A, B, C, etc).

For example, a protein (e.g. protein g) might produce three peptides (e.g. peptides B, C and D) when digested with a protease such as trypsin. Accordingly, a sample that has been digested with a proteolytic enzyme, such as trypsin, and that when analyzed is confirmed to contain peptides B, C and D, can be said to have originally comprised the protein g. The quantity of peptides B, C and D will also correlate with the quantity of protein g in the sample that was digested. In this way, any determination of the identity and/or quantify of one or more of peptides B, C and D in a sample (or a fraction thereof, can be used to identify and/or quantify protein g in the original sample (or a fraction thereof.

Because activity of the enzymes is predictable, the sequence of peptides that are produced from degradation of a protein of known sequence can be predicted. With this information, "theoretical" peptide information can be generated. A determination of the "theoretical" peptide fragments in computer assisted analysis of daughter fragment ions (as described above) from mass spectrometry analysis of an actual sample can therefore be used to determine one or more peptides or proteins in one or more unknown samples (See for example the section above entitled: "*Analyte Determination By Computer Assisted Database Analysis*").

In some embodiments, sample processing can include treatment of precursors to the analyte or analytes to be labeled. For example, if the analyte or analytes to be labeled are peptides derived from a digested protein and the labeling reagent is, for this example, selected to react the peptide or peptide analytes, the protein (the analyte precursor molecule) of the sample may be processed in a manner that facilitates the labeling reaction. In this example, the protein can be reduced with a reducing agent (e.g. tris[2-carboxyethyl] phosphine (TCEP)) and the thiol groups then blocked by reaction with a blocking reagent (e.g. methyl methanethiosulfonate (MMTS)). In this way the thiol groups of the protein are blocked and therefore do not interfere with the labeling reaction between the amines of the analytes and labeling reagent.

Those of skill in the art will appreciate that treatment of certain other precursor molecules can be performed using readily available reagents and protocols that can be adapted with the aid of routing experimentation. The precise choices or reagents and conditions can be selected depending on the nature of the analyte to be labeled and the labeling reagent.

In some embodiments, sample processing can include the immobilization of the analytes or analyte precursors to a solid support, whether labeled with a labeling reagent or not. Immobilization can include covalent immobilization as well as adsorption and other non-covalent means of immobilization (e.g. electrostatic immobilization). In some embodiments, immobilization can facilitate reducing sample complexity. In some embodiments, immobilization can facilitate analyte labeling. In some embodiments, immobilization can facilitate analyte precursor labeling. In some embodiments, immobilization can facilitate selective labeling of a fraction of sample components comprising a certain property (e.g. they comprise or lack cysteine moieties). In some embodiments, immobilization can facilitate purification. The immobilization can facilitate two or more of the foregoing.

Separation Including Separation of the Sample Mixture:

In some embodiments, the processing of a sample or sample mixture of labeled analytes can involve separation. One or more separations can be performed on the labeled or unlabeled analytes, labeled or unlabeled analyte precursors, or fractions thereof. One or more separations can be performed on one or more fractions obtained from a solid phase capture or other product of a separations process. Separations can be preformed on two or more of the foregoing.

For example, a sample mixture comprising differentially labeled analytes from different samples can be prepared. By differentially labeled we mean that each of the labels comprises a unique property that can be identified (e.g. comprises a unique reporter moiety that produces a unique "signature ion" in MS/MS analysis). In order to analyze the sample mixture, components of the sample mixture can be separated and mass analysis performed on only a fraction of the sample mixture. In this way, the complexity of the analysis can be substantially reduced since separated analytes can be individually analyzed for mass thereby increasing the sensitivity of the analysis process. Of course the analysis can be repeated one or more time on one or more additional fractions of the sample mixture to thereby allow for the analysis of all fractions of the sample mixture.

Separation conditions under which identical analytes that are differentially labeled co-elute at a concentration, or in a quantity, that is in proportion to their abundance in the sample mixture can be used to determine the amount of each labeled analyte in each of the samples that comprise the sample mixture provided that the amount of each sample added to the sample mixture is known. Accordingly, in some embodiments, separation of the sample mixture can simplify the analysis whilst maintaining the correlation between signals determined in the mass analysis (e.g. MS/MS analysis) with the amount of the differently labeled analytes in the sample mixture.

The separation can be performed by chromatography. For example, liquid chromatography/mass spectrometry (LC/MS) can be used to effect sample separation and mass analysis. Moreover, any chromatographic separation process suitable to separate the analytes of interest can be used. For example, the chromatographic separation can be normal phase chromatography, reversed-phase chromatography, ion-exchange chromatography (i.e. anion exchange chromatography or cation exchange chromatography), size exclusion chromatography or affinity chromatography.

The separation can be performed electrophoretically. Non-limiting examples of electrophoretic separations techniques that can be used include, but are not limited to, 1D electrophoretic separation, 2D electrophoretic separation and/or capillary electrophoretic separation.

An isobaric labeling reagent or a set of reagents can be used to label the analytes of a sample. Isobaric labeling reagents are particularly useful when a separation step is performed because the isobaric labels of a set of labeling reagents are essentially indistinguishable (and can be indistinguishable by gross mass until fragmentation removes the reporter from the analyte). Thus, all analytes of identical composition that are labeled with different isobaric labels can chromatograph in exactly the same manner (i.e. co-elute). Because they are essentially indistinguishable, the eluent from the separation process can comprise an amount of each isobarically labeled analyte that is in proportion to the amount of that labeled analyte in the sample mixture. Furthermore, from the knowledge of how the sample mixture was prepared (portions of samples and other optional components (e.g. calibration standards) added to prepare the sample mixture), it is possible to relate the amount of labeled analyte in the sample mixture back to the amount of that labeled analyte in the sample from which it originated.

The labeling reagents can also be mass differential labeling reagents (i.e. labeling reagents of different gross mass). Mass differential labeling reagents can be used to label, for example, the analytes of two or more different samples wherein the different labeling reagents of a set all have a distinct mass (i.e. known mass difference as compared with other reagents of the set). Because all the reagents of the set can have a known mass difference, the labeling reagents need not be fragmented in order to quantify the relative amounts of like analytes in two different samples. However, in some embodiments, the labeling reagents can be fragmentable.

Relative and Absolute Quantification of Analytes:

In some embodiments, the relative quantification of differentially labeled identical analytes of a sample mixture is possible. For example, relative quantification of differentially labeled identical analytes is possible by comparison of the relative amounts (e.g. area and/or height of the peak reported) of reporter ion (i.e. signature ion) that are determined in the mass analysis (e.g. in the second mass analysis for a selected, labeled analyte observed in a first mass analysis). Stated differently, where each reporter ion can be correlated with information for a particular sample used to produce a sample mixture, the relative amount of that reporter ion, with respect to other reporter ions observed in the mass analysis, is the relative amount of that analyte in the sample mixture. Where components combined to form the sample mixture are known (e.g. the amount of each sample combined to form a sample mixture), the relative amount of the analyte in each sample used to prepare the sample mixture can be back calculated based upon the relative amounts of reporter ion observed for the labeled analyte of selected mass to charge. This process can be repeated for all of the different labeled analytes observed in the first mass analysis. In this way, the relative amount (often expressed in concentration and/or quantity) of each reactive analyte, in each of the different samples used to produce the sample mixture, can be determined.

In other embodiments, absolute quantification of analytes can be determined. For these embodiments, a known amount of one or more differentially labeled analytes (the calibration standard or calibration standards) can be added to the sample mixture or the intensity of the reporter ion can be correlated with a calibration curve.

A calibration standard can be an expected analyte that is labeled with an isomeric and/or isobaric label of the set of labels used to label the analytes of the sample mixture provided that the reporter moiety for the calibration standard is unique as compared with any of the samples used to form the sample mixture. Once the relative amount of reporter ion for the calibration standard, or standards, is determined with relation to the relative amounts of the reporter ion or ions for the differentially labeled analytes of the sample mixture, it is possible to calculate the absolute amount (often expressed in concentration and/or quantity) of all of the differentially labeled analytes in the sample mixture with reference to the amount of calibration standard or standards that was (were) added to the sample mixture. In this way, the absolute amount of each differentially labeled analyte (for which there is a calibration standard in the sample from which the analyte originated) can also be determined based upon the knowledge of how the sample mixture was prepared.

Alternatively, a calibration curve can be prepared by analysis of representative samples of labeled analytes, each sample comprising a different known amount of the labeled analyte. The intensities of the peaks of the reporter ion of the analyzed labeled analyte (isobaric sets) or peaks of labeled analytes (mass differential sets) can be plotted with respect to the known amount of each labeled analyte to thereby generate the standard curve. Once prepared the intensity of a reporter ion or labeled analyte (as appropriate) in an unknown sample can be compared with the standard curve to thereby determine the amount of the analyte in a test sample.

Notwithstanding the foregoing, corrections to the intensity of the reporters ion (signature ions) can be made, as appropriate, for any naturally occurring, or artificially created, isotopic abundance within the reporter moieties. There are numerous ways to correct for isotopic abundance of impurities in the signature ions of reporter moieties. An example of such a correction can be found in published copending and co-owned United States Provisional Patent Application No. US 2005-0114042 A1, entitled: "Method and Apparatus For De-Convoluting A Convoluted Spectrum", filed on Aug. 12, 2004. Basically, the intensity of up-mass and down mass peaks associated with the isotopic cluster of a single labeling reagent can be determined by deconvolution of the convoluted spectrum of the overlapping isotopic clusters of the labeling reagents using mathematical formulas and calculations. Regardless of how the values are determined, the more care taken to accurately quantify the intensity of each reporter ion (i.e. signature ion), the more accurate will be the relative and absolute quantification of the analytes in the original samples.

Proteomic Analysis:

Embodiments of this invention can be used for complex analysis because samples can be multiplexed, analyzed and reanalyzed in a rapid and repetitive manner using mass analysis techniques. For example, sample mixtures can be analyzed for the amount of one or more analytes in one or more samples. The amount (often expressed in concentration and/or quantity) of the analyte or analytes can be determined for the samples from which the sample mixture was comprised. Because the sample processing and mass analyses can be performed rapidly, these methods can be repeated numerous times so that the amount of many differentially labeled analytes of the sample mixture can be determined with regard to their relative and/or absolute amounts in the sample from which the analyte originated.

One application where such a rapid multiplex analysis is useful is in the area of proteomic analysis. Proteomics can be viewed as an experimental approach to describe the information encoded in genomic sequences in terms of structure, function and regulation of biological processes. This may be achieved by systematic analysis of the total protein component expressed by a cell or tissue. Mass spectrometry, used in combination with the method, mixture, kit and/or composition embodiments of this invention is one possible tool for such global protein analysis.

For example, with a set of nine isobaric labeling reagents, it is possible to obtain nine time points in an experiment to determine up or down regulation of protein expression, for example, based upon response of growing cells to a particular stimulant. It is also possible to perform fewer time points but to incorporate one or more controls. It is also possible to do duplicates or triplicates in the same multiplex experiment. In all cases, up or down regulation of the protein expression, optionally with respect to the one or more optional controls and/or sample repeats, can be determined in a single multiplex experiment. Moreover, because processing of the sample mixture is performed in parallel, the results are directly comparable such that no compensation need be applied to account for slight variations in protocol or experimental conditions. Accordingly, experimental analysis for which these isobaric labeling reagents can be used includes, but is not limited to, time course experiments, biomarker analysis, multiplex proteomic analysis, mudpit experiments, affinity pull-downs, determination of post-translational modifications (PTMs) and multiple control experiments.

II Compositions

In some embodiments, this invention pertains to compositions represented by formula I;

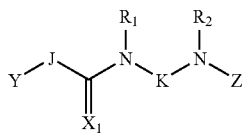

I including a salt form and/or hydrate form thereof; wherein, the group Y-J can be any reporter group. The characteristics of suitable reporter groups have been previously described herein. The characteristics of suitable reporter groups have also been described in US Published Patent Application No. US 2004-0219685-A1 at, inter alia, paragraphs 41-47.

For example, the reporter can comprise a 5, 6 or 7 membered heterocyclic ring, as the group Y, wherein said heterocyclic ring may be substituted or unsubstituted and may optionally be cleavably linked to a support, wherein the heterocyclic ring comprises at least one ring nitrogen atom that is linked through a covalent bond to the group J. The group J can be a substituted or unsubstituted methylene group represented by formula —$CJ'_2$—, wherein each J' is, independently of the other, hydrogen, deuterium, fluorine, chlorine, bromine, iodine, —$R_3$, —$OR_3$, —$SR_3$, —$R_3'OR_3$ or —$R_3'SR_3$. The group K can be a group represented by formula: —$(CK'_2)_n$— or —$((CK'_2)_m$—$X_2$—$(CK'_2)_m)_p$—, wherein n is 0 or an integer from 2 to 10, each m is, independently of the other, an integer from 1 to 5, p is an integer from 1 to 4 and each K' is, independently of the other, hydrogen, deuterium, fluorine, chlorine, bromine, iodine, —$R_4$, —$OR_4$, —$SR_4$, —$R_4$, —$OR_4$ or —$R_4'SR_4$. Regarding the groups $R_1$ and $R_2$, either: (1) $R_1$ is hydrogen, deuterium or $R_6$ and $R_2$ is hydrogen, deuterium or $R_7$; or (2) $R_1$ and $R_2$ taken together is a group represented by formula —$(CR'_2)_q$— or —$((CR'_2)_m$—$X_2$—$(CR'_2)_m)_p$—that forms a ring that bridges the two nitrogen atoms, wherein q is an integer from 1 to 10, each m is, independently of the other, an integer from 1 to 5, p is an integer from 1 to 4 and each R' is, independently of the other, hydrogen, deuterium, fluorine, chlorine, bromine, iodine, —$R_5$, —$OR_5$, —$SR_5$, —$R_5'OR_5$ or —$R_5'SR_5$. The atom or group $X^1$ can be =O, =S, =NH or =$NR_7$. The atom or group $X_2$ can be —O— or —S—. The group Z can be hydrogen or a covalently linked analyte. Each $R_3$, $R_4$, $R_5$, $R_6$ and/or $R_7$, independently of the other, can be alkyl, alkenyl, alkynyl, aryl, heteroaryl or arylalkyl. For example each $R_3$, $R_4$, $R_5$, $R_6$ and/or $R_7$, independently of the other, can be methyl, ethyl, n-propyl, isopropyl, n-butyl, isobutyl, sec-butyl or tert-butyl. Each $R_3'$, $R_4'$ and/or $R_5'$, independently of the other, can be alkylene, alkenylene, alkynylene, arylene or alkylarylene. For example, each $R_3'$, $R_4'$, and/or $R_5'$, independently of the other, can be methylene, ethylene, propylene, cyclopropylene, n-butylene, cyclobutylene, n-pentylene, cyclopentylene, n-hexylene or cyclohexylene.

In some embodiments, Y-J can be a group represented by formulas: $X^1$, $X^2$, $X^3$, $X^4$, $X^5$, $X^6$, $X^7$, $X^8$ or $X^9$ as described above. In some embodiments, Y-J can be a group represented by formulas: $X^{10}$, $X^{11}$, $X^{12}$, $X^{13}$, $X^{14}$, $X^{15}$, $X^{16}$, $X^{17}$, $X^{18}$, $X^{19}$, $X^{20}$, $X^{21}$, $X^{22}$, $X^{23}$, $X^{24}$, $X^{25}$ or $X^{26}$ as described above.

The compositions can be isotopically enriched (i.e. encoded). The compositions can be isotopically enriched to comprise one or more heavy atom isotopes. The compositions can be isotopically enriched to comprise two or more heavy atom isotopes. The compositions can be isotopically enriched to comprise three or more heavy atom isotopes. The compositions can be isotopically enriched to comprise four or more heavy atom isotopes.

The 5, 6 or 7 membered heterocyclic ring can be any 5, 6 or 7 membered heterocyclic ring that comprises at least one nitrogen atom to which the group J can be covalently linked. For example, it can be a substituted or unsubstituted morpholine, piperidine or piperazine. Possible substituents have been described above in the "Definitions" section wherein the heterocyclic ring can comprise one or more of said substituents. For example, a substituent can be hydrogen, deuterium, methyl, —$C(H)_2D$, —$C(H)D_2$, —$CD_3$ or other alkyl (in each case 'D' is deuterium). The substituent can be linked to a heteroatom of the ring. For example, the heterocyclic ring can be N-methylpiperazine. The heterocyclic ring can be aromatic or non-aromatic.

In some embodiments, the reporter moiety can be cleavably linked to a support. Various supports are well known in the art. For example, various supports comprising a trityl moiety are sold commercially or can otherwise be prepared (e.g. Trityl chloride support (Trityl-Cl) or 2-Chlorotrityl chloride support).

For example, the amino, hydroxyl or thiol group of a reporter moiety of a labeling reagent can be reacted with the cleavable linker of a suitable support. The cleavable linker can be a "sterically hindered cleavable linker". Cleavage of the cleavable linker will release the label or a labeled analyte from the support. Non-limiting examples of sterically hindered solid supports include: Trityl chloride resin (trityl-Cl, Novabiochem, P/N 01-64-0074), 2-Chlorotrityl chloride resin (Novabiochem, P/N 01-64-0021), DHPP (Bachem, P/N Q-1755), MBHA (Applied Biosystems P/N 400377), 4-methyltrityl chloride resin (Novabiochem, P/N 01-64-0075), 4-methoxytrityl chloride resin (Novabiochem, P/N 01-64-0076), Hydroxy-(2-chorophnyl)methyl-PS (Novabiochem, P/N 01-64-0345), Rink Acid Resin (Novabiochem P/Ns 01-64-0380, 01-64-0202), NovaSyn TGT alcohol resin (Novabiochem, P/N 01-64-0074). Numerous other cleavable linkers are known in the art and can be used to prepare suitable supports using no more than commercially available materials, routine experimentation and the teachings provided herein.

Accordingly, in some embodiments, the 5, 6 or 7 member heterocyclic ring can comprise an atom or group that facilitates the cleavable linkage of it to a suitable support. For example, the group can be an alkylene, alkenylene, alkynylene, arylene or alkylarylene group comprising an amino, hydroxyl or thiol group. The atom can be the secondary nitrogen of a piperazine ring. A discussion of exemplary piperazine compounds and methods for their manufacture can be found in published U.S. patent application No: US 2004-0219685 A1. For example, said support bound N-alkyl piperazine acetic acid compounds can be reacted with a diamine followed by reaction with a diacid to thereby form support bound compounds that can be used as labeling reagents, where isotopic encoding is possible based upon the nature of the reactants.

Again with reference to formula I, the group Y-J- (whether or not cleavably linked to a support) can form the reporter moiety. The reporter moiety can comprise at least one isotopically enriched site. The reporter moiety can comprise at least two isotopically enriched sites. The reporter moiety can comprise 3, 4, 5, 6, 7, 8, 9, 10, 11, 12, 13, 14, 15, 16 or 17, or more isotopically enriched sites.

The reporter moiety can either contain a fixed charge or be ionizable in a mass spectrometer. For example, compounds comprising basic groups (e.g. amine groups) are easily protonated to introduce charge and acidic compounds (e.g. carboxylic acid groups) are easily deprotonated to thereby introduce charge (See: Roth, Kenneth et al, "Charge Derivatization of Peptides for Analysis by Mass Spectrometry", *Mass Spectrometry Reviews*, 17: 255-274 (1998)).

The balance (linker) moiety can be formed by the group represented by formula I#;

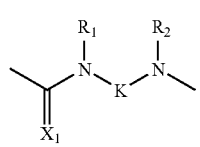

wherein $R_1$, $R_2$, $X_1$, and K are defined previously. The balance moiety can comprise at least one isotopically enriched site. The balance moiety can comprise at least two isotopically enriched sites. The balance moiety can comprise 3, 4, 5, 6, 7, 8, 9, 10, 11, 12, 13, 14, 15, 16 or 17, or more isotopically enriched sites.

In some embodiments, the composition can be represented by formula II;

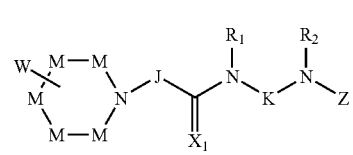

including a salt form and/or hydrate form thereof; wherein W is an atom or group that is substituted for at least one M group of the six membered heterocyclic ring and is located ortho, meta or para to the nitrogen of the six membered ring. The group W can be —N(H)—, —N(R")—, —N(R'")—, —P(R")—, —P(R'")—, —O— or —S—. If selected as —N(R'")— or —P(R'")—, the group can be used to cleavably link the composition to a support. Each remaining group M can be, independently of the other, —CM'$_2$—, wherein each M' can be, independently of the other, hydrogen, deuterium, fluorine, chlorine, bromine, iodine, —$R_8$, —O$R_8$, —S$R_8$, —$R_8$'O$R_8$ or —$R_8$'S$R_8$. The groups J, K, $X_1$, $R_1$, $R_2$ and Z are as previously defined. Each R", independently of the other, can be alkyl, alkenyl, alkynyl, aryl, heteroaryl or arylalkyl and each R'" can be H$_2$N—$R_9$'—, H($R_{10}$)N—$R_9$—, ($R_{10}$)$_2$N—$R_9$'—, HO—$R_9$'—, HS—$R_9$'— or a cleavable linker that cleavably links the compound to a support. Each $R_8$ and/or $R_{10}$ can be, independently of the other, alkyl, alkenyl, alkynyl, aryl, heteroaryl or arylalkyl and each $R_8$' and/or $R_9$' can be, independently of the other, alkylene, alkenylene, alkynylene, arylene or alkylarylene.

In some embodiments, the composition can be represented by formula III;

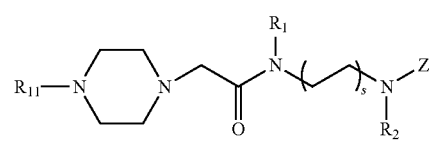

including a salt form and/or hydrate form thereof, wherein s can be an integer from 0 to 5. The groups $R_1$, $R_2$ and Z are as previously defined. The atom or group $R_{11}$ can be hydrogen, deuterium, methyl, —C(H)$_2$D, —C(H)D$_2$, —CD$_3$, other alkyl or —R'", wherein R'" is as previously defined. For example, the composition can be selected from one of compounds V-XII or XXV to XXXII as illustrated below.

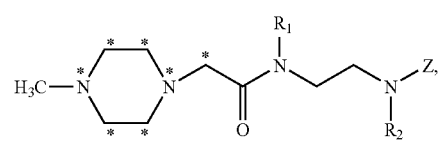

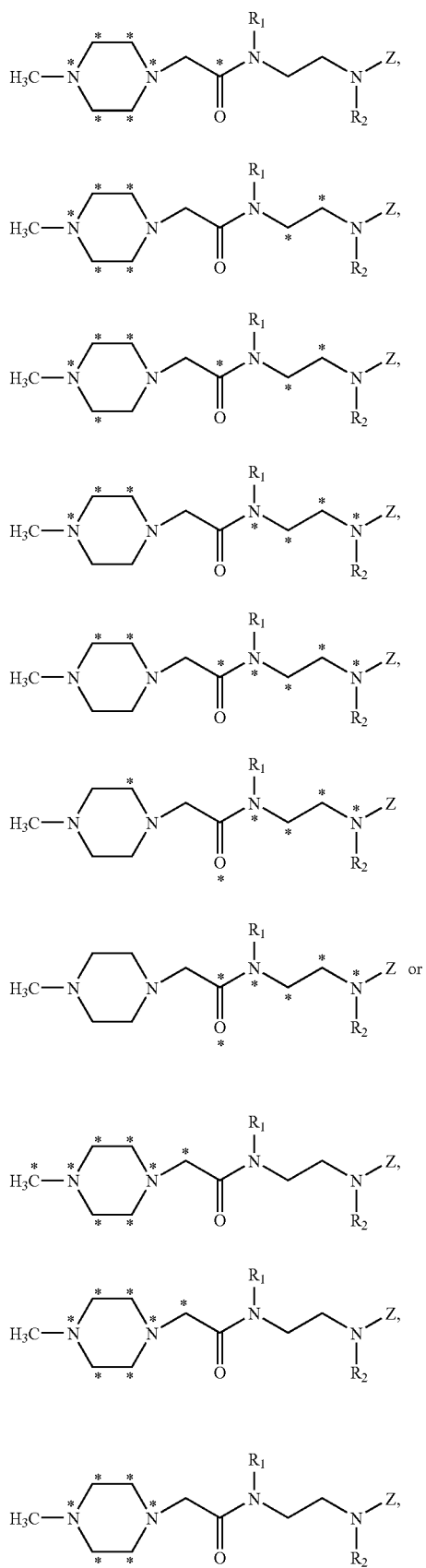
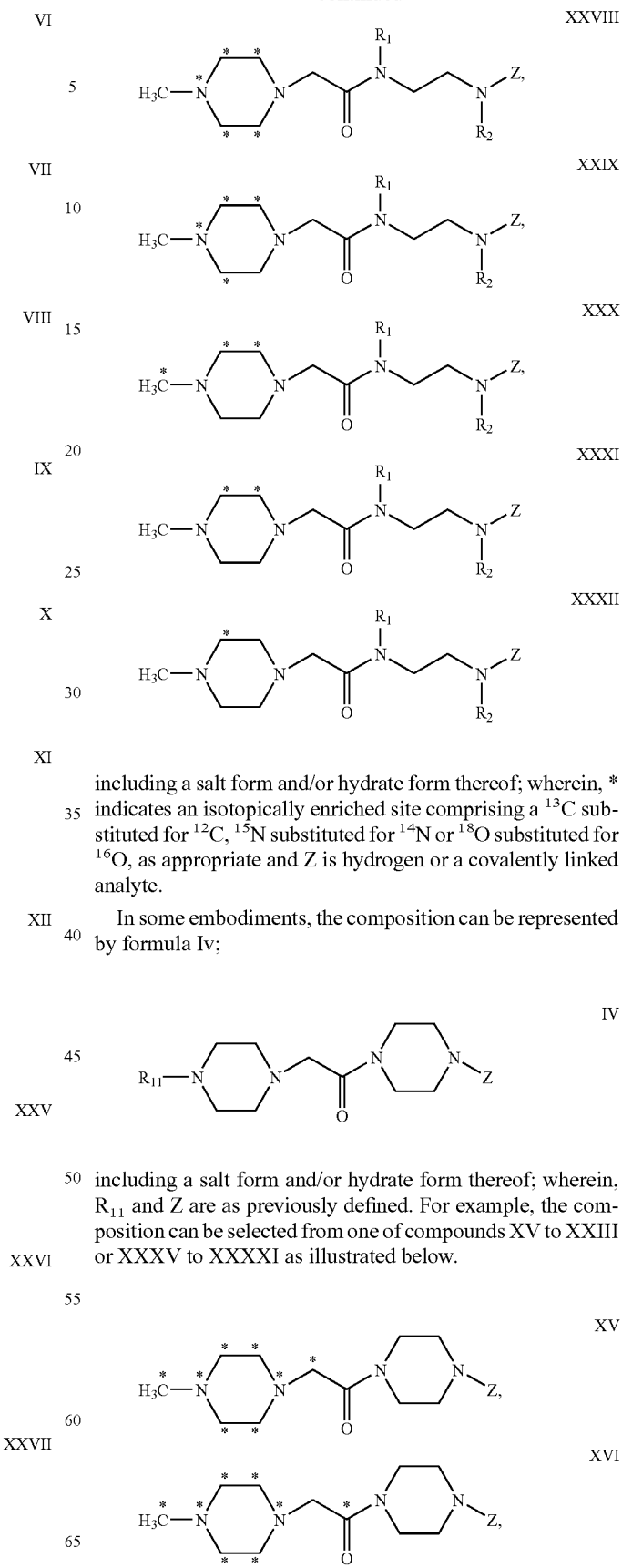

including a salt form and/or hydrate form thereof; wherein, * indicates an isotopically enriched site comprising a $^{13}C$ substituted for $^{12}C$, $^{15}N$ substituted for $^{14}N$ or $^{18}O$ substituted for $^{16}O$, as appropriate and Z is hydrogen or a covalently linked analyte.

In some embodiments, the composition can be represented by formula Iv;

including a salt form and/or hydrate form thereof; wherein, $R_{11}$ and Z are as previously defined. For example, the composition can be selected from one of compounds XV to XXIII or XXXV to XXXXI as illustrated below.

-continued

XVII
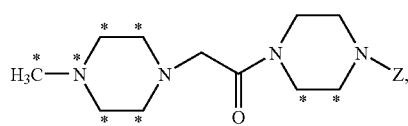

XVIII
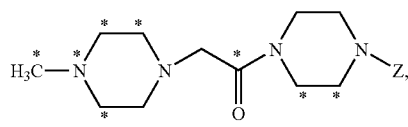

XIX
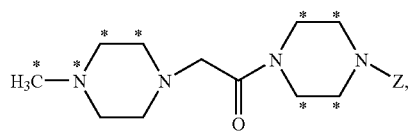

XX
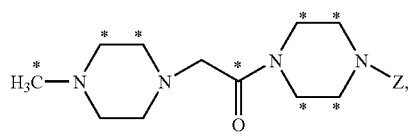

XXI
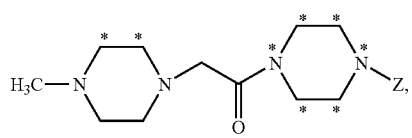

XXII
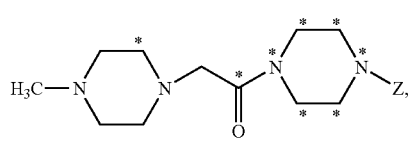

XXIII
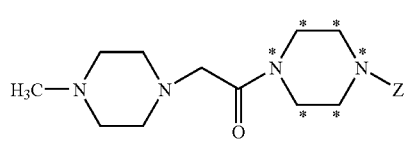

XXXV
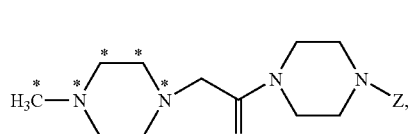

XXXVI
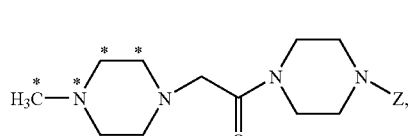

XXXVII
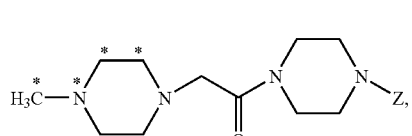

XXXVIII
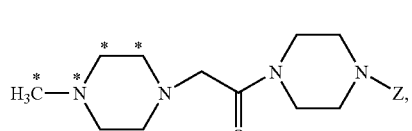

-continued

XXXIX
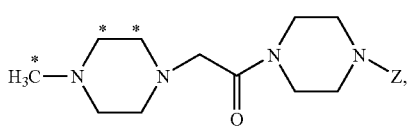

XXXX
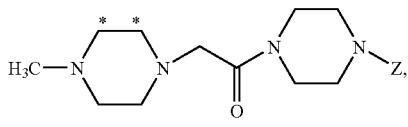

XXXXI
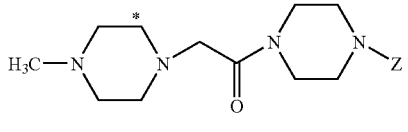

including a salt form and/or hydrate form thereof; wherein, * indicates an isotopically enriched site comprising a $^{13}C$ substituted for $^{12}C$, $^{15}N$ substituted for $^{14}N$ or $^{18}O$ substituted for $^{16}O$, as appropriate and Z is hydrogen or a covalently linked analyte.

In some embodiments, the composition can be represented by formula III*;

III*
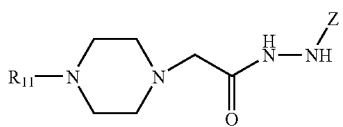

including a salt form and/or hydrate form thereof; wherein, $R_{11}$ and Z are as previously defined. For example, the composition can be selected from one of compounds M to MV or MVI to MXIII as illustrated below.

M
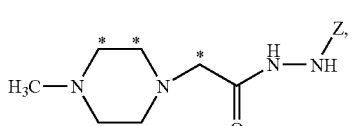

MI
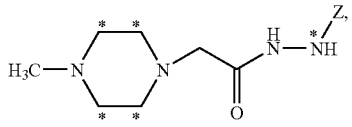

MII
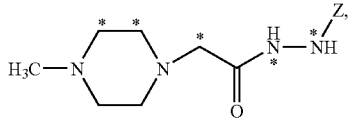

MIII
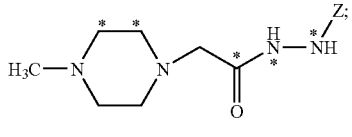

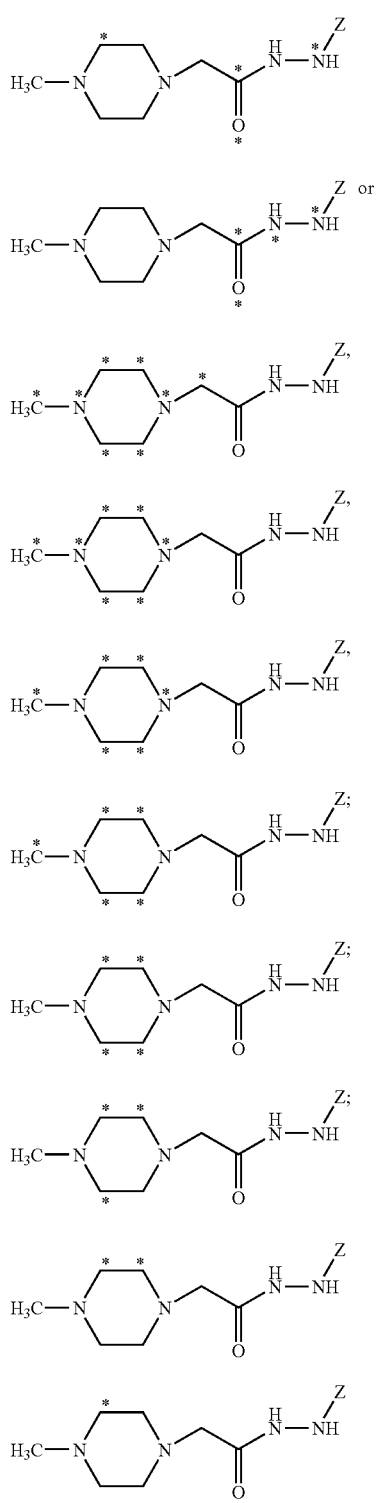

including a salt form and/or hydrate form thereof; wherein, * indicates an isotopically enriched site comprising a $^{13}C$ substituted for $^{12}C$, $^{15}N$ substituted for $^{14}N$ or $^{18}O$ substituted for $^{16}O$, as appropriate and Z is hydrogen or a covalently linked analyte.

As stated, the compositions can exist in a salt form and/or hydrate form. Whether or not the composition exists as a salt form will typically depend upon the nature and number of substituents as well as the conditions under which it exists and/or was isolated. It is well known that basic groups such as amines can be protonated by treatment with acid to thereby form salts of the amine. For example, piperazine containing labeling reagents can be obtained as a mono-TFA salt, a mono-HCl salt, a bis-TFA salt or a bis-HCl salt (See for Example, US Patent Application Publication No. US 2005-0148771A1). It is also well known that acidic groups, such as carboxylic acids, can be deprotonated by treatment with base to form carboxylate salts. Id. It is also well-known that compounds comprising both a basic group such as an amine and an acidic group such as a carboxylic acid can exist in zwitterionic form. All these are considered salt forms and the ionization state of these functional groups of the composition will depend either on the pH of any solution in which they exist, or if isolated, on the pH of the solution from which they were isolated. One of ordinary skill in the art will surely appreciate how to manipulate the charge state and nature of any counterion the salt form of the compositions disclosed herein using no more than routine experimentation and the disclosure provided herein.

Whether or not a composition exists as a hydrate can also depend the conditions under which it exists or was isolated. Hydrates merely comprise one or more complexed water molecules. This disclosure contemplates any possible hydrate form or combinations thereof.

As previously described, the group Z can be a covalently linked analyte. Said analytes can be prepared by reaction of the analyte with a labeling reagent. The analyte can be any analyte. For example, the group Z can be a peptide or protein.

The group Z can also be hydrogen and thus comprise a nucleophilic reactive group.

Labeling reagents can organized into sets that can be isobaric and/or mass differential labeling sets. Other properties of the labeling reagents have been disclosed. For example, the labeling reagents can be useful for the multiplex analysis of one or more analytes in the same sample, or in two or more different samples.

The labeling reagents can be isotopically enriched (i.e. encoded). The labeling reagents can be isotopically enriched to comprise one or more heavy atom isotopes. The labeling reagents can be isotopically enriched to comprise two or more heavy atom isotopes. The labeling reagents can be isotopically enriched to comprise three or more heavy atom isotopes. The labeling reagents can be isotopically enriched to comprise four or more heavy atom isotopes.

In some embodiments, a composition of this invention can be a labeled calibration standard. As described herein, calibration standards can be added to mixtures in known quantities to facilitate absolute quantitative analysis of an analyte of interest. Accordingly, in some embodiments, this invention pertains to an analyte, such as a peptide of interest, which has been labeled with an isobaric and/or mass differential labeling reagent. Thus, the labeled calibration standard can be any analyte labeled with a labeling reagent as described herein. The labeling reagent can be selected from a set of isobaric and/or mass differential labeling reagents.

III. Methods for Labeling and Analysis

According to some embodiments of this invention, analytes can be labeled and then determined. The labeled analyte, the analyte itself, one or more fragments of the analyte and/or fragments of the label, can be determined by mass analysis. In some embodiments, methods of this invention can be used for the analysis of different analytes in the same sample as well as for the multiplex analysis of the same and/or different analytes in two or more different samples. The two or more samples can be mixed to form a sample mixture. In multiplex analysis, labeling reagents can be used to determine from which sample of a sample mixture an analyte originated. The absolute and/or relative (e.g. with respect to the same analyte in different samples) amount (often expressed in concentration or quantity) of the analyte, in each of two or more of the samples combined to form the sample mixture, can be determined. Moreover, mass analysis of fragments of the analyte (e.g. daughter fragment ions) can be used to identify the analyte and/or the precursor to the analyte; such as where the precursor molecule to the analyte was degraded.

The samples used in the analysis may be any sample comprising analytes that can be labeled with the labeling reagents disclosed herein such as those described above under the heading 'Compositions'. For example, the sample can be a crude or processed cell lysate, a body fluid, a tissue extract or a cell extract. The sample can be a fraction from a separations process. Other possible sample types have been described herein.

The analyte in the sample can be any analyte that can be labeled with the labeling reagent. For example, the analyte can be a peptide and/or protein. Other possible analyte types have been disclosed herein.

One distinction of the described approach lies in the fact that analytes from different samples can be differentially labeled (i.e. encoded) with unique labels that are chemically isobaric (have identical gross mass) or are mass differential tags and that identify the sample from which the analyte originated. For isobaric labeling reagents, the differentially labeled analytes are not distinguished in MS mode of a mass spectrometer because they all have identical (gross) mass to charge ratios. Often, the labeling reagents of a set are selected so that the labeled analytes are also not distinguishable by separation techniques, such as chromatography or electrophoresis, which might be applied to the mixture before the first mass analysis. However, when subjected to dissociative energy, such as through collision induced dissociation (CID), the labels can fragment to yield unique reporter ions that can be resolved by mass (mass to charge ratio) in a mass spectrometer. The relative amount of each unique reporter ion observed in the MS/MS (or MS$^n$ wherein n is an integer greater than 1) mass spectrum can be correlated with the relative amount of a labeled analyte in the sample mixture and, by implication, the relative amount of that analyte in a sample from which it originated. Thus, the relative intensities of the reporter ions (i.e. signature ions) can be used to determine the relative amount of an analyte or analytes in two or more different samples that were combined to form a sample mixture. From the reporter ion information, absolute amounts (often expressed as concentration and/or quantity) of an analyte or analytes in two or more samples can be derived if calibration standards for each analyte, for which absolute quantification is desired, are incorporated into the sample mixture in a known quantity or where a calibration curve for the reporter ions or labeled analytes is available.

For example, the analyte might be a peptide that resulted from the degradation of a protein using an enzymatic digestion reaction to process the sample. Protein degradation can be accomplished by treatment of the sample with one or more proteolytic enzymes (e.g. trypsin, papain, pepsin, ArgC, LysC, V8 protease, AspN, pronase, chymotrypsin or carboxypeptidase). By determination of the identity and amount of a peptide in a sample mixture and identifying the sample from which it originated, optionally coupled with the determination of other peptides from that sample, the precursor protein to the degraded peptide can be identified and/or quantified with respect to the sample from which it originated. Because this method allows for the multiplex determination of a protein, or proteins, in more than one sample (i.e. from a sample mixture), it is a multiplex method.

Consequently, in some embodiments, this invention pertains to a method comprising reacting two or more samples, each sample comprising one or more reactive analytes, with a different labeling reagent of a set of labeling reagents to thereby produce two or more differentially labeled samples each comprising one or more labeled analytes. The labeling reagents can be selected from a set of isobaric and/or mass differential labeling reagents.

For example, the different labeling reagents of the set can be represented by formula I';

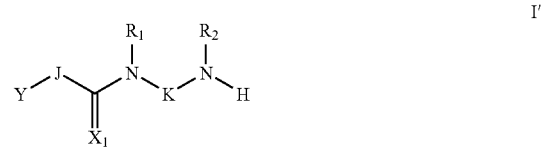

including a salt form and/or hydrate form thereof, wherein the atoms or groups Y, J, K, $R_1$, $R_2$, and $X^1$ are as previously defined. In some embodiments, Y can be a substituted or unsubstituted morpholine, piperidine or piperazine moiety.

In some embodiments, the labeling reagents of a set can be isobaric and/or isomeric wherein each different labeling reagent of the set has the same gross mass but wherein the group Y-J, which group forms a reporter moiety, of each different labeling reagent is uniquely encoded at one or more isotopically enriched sites such that when the bond between the group J, of the group Y-J, and the remainder of the labeling reagent fragments in a mass spectrometer, a reporter ion of unique mass is produced. In some embodiments, the reporter moiety can comprise a substituted or unsubstituted piperidine, piperazine or morpholine group.

In some embodiments, the labeling reagents can be a set of mass differential tags wherein all labels of the set comprise a different mass. These labeling reagents can be designed to fragment when subjected to dissociative energy, but need not be so designed since analysis is typically performed in the MS$^1$ mode. Thus, in some embodiments, the group Y-J of each different labeling reagent of the set can be uniquely encoded at one or more isotopically enriched sites such that when the bond between the group J, of the group Y-J, and the remainder of the labeling reagent fragments in a mass spectrometer, a reporter ion of unique mass is produced.

Regardless of whether the set is isobaric (and/or isomeric) or mass differential, if the labeling reagents are capable of generating reporter ions, the labeling reagents can, in some embodiments, be selected to each comprise a unique mass. Consequently, each reporter ion of unique mass can be used to identify the sample from which each labeled analyte originated.

Reagents of formula I' comprise a nucleophilic nitrogen which can react with a carboxylic acid moiety of the analyte to form an amide. The nucleophilic nitrogen can also react with an aldehyde or ketone of the analyte but typically the shifts base is reduced to thereby form a stable adduct. Regardless of how formed, the labeled analytes of the sample mixture can be represented by formula I'';

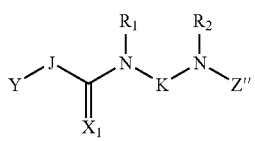

including a salt form and/or hydrate form thereof, wherein the atoms or groups Y, J, K, $R_1$, $R_2$, and $X_1$ are as previously defined and the group Z" can be a covalently linked analyte. In some embodiments, the variable Y can be a substituted or unsubstituted morpholine, piperidine or piperazine group.

The labeling process can produce two or more differentially labeled samples each comprising one or more labeled analytes. Once the analytes of each sample are labeled with the labeling reagent that is unique to that sample, the two or more differentially labeled samples, or a portion thereof, can be mixed to produce a sample mixture. The sample mixture can optionally comprise one or more calibration standards.

The volume and/or quantity of each sample combined to produce the sample mixture can be recorded. The volume and/or quantity of each sample, relative to the total sample volume and/or quantity of the sample mixture, can be used to determine a ratio that can be used for determining the amount (often expressed in concentration and/or quantity) of an identified analyte in each sample from the analysis of the sample mixture. The sample mixture can therefore comprise a complex mixture wherein relative amounts of the same and/or different analytes can be identified and/or quantified, either by relative quantification of the amounts of analyte in each of the two or more samples or absolutely where a calibration standard is also added to the sample mixture.

Figure 1B:
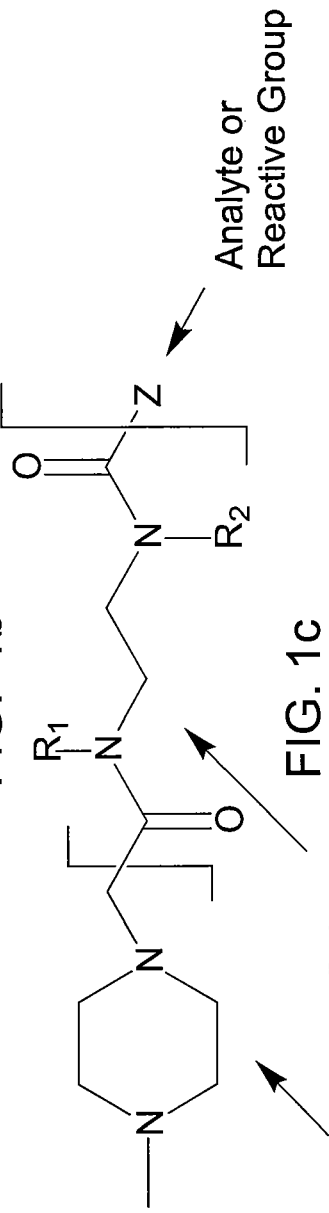
FIG. 1b is an illustration of the general elements of an exemplary N-methyl piperazine based labeling reagent or labeled analyte and some fragmentation characteristics.
Figure 1C:
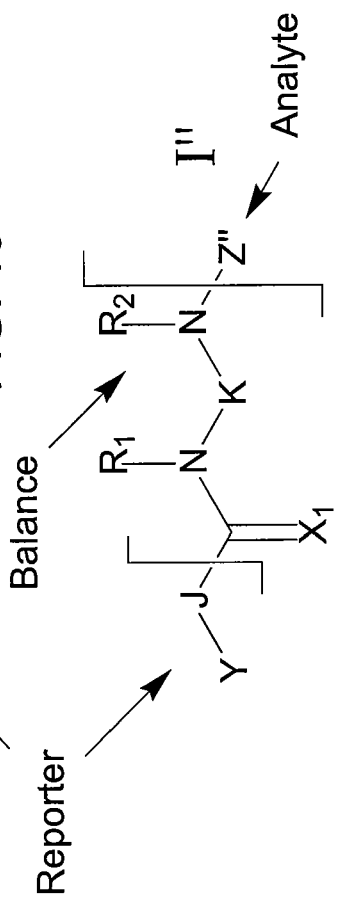
FIG. 1c is an illustration of the general elements of a labeled analyte of the identified general formula and some fragmentation characteristics.

For isobaric sets of labeling reagents, the mixture can, for example, be subjected to spectrometry techniques wherein a first mass analysis can be performed on the sample mixture, or fraction thereof, using a first mass analyzer. Ions of a particular mass to charge ratio from the first mass analysis can then be selected. The selected ions can be subjected to dissociative energy (e.g. collision-induced dissociation (CID)) to thereby induce fragmentation of the selected ions. By subjecting the selected ions of the labeled analytes to dissociative energy bonds can be fragmented in at least a portion of the selected ions. In some embodiments, fragmentation of both bonds can cause fragmentation of the reporter/linker moiety as well as cause release the ionized reporter moiety (i.e. the reporter ion or signature ion) from the analyte. Examples of such fragmentation for various labeling reagents is illustrated in FIGS. 1a to 1c. Fragmentation of the selected ions by the dissociative energy can also produce daughter fragment ions of the analyte. The ions (remaining selected ions, daughter fragment ions and ionized reporter moieties (i.e. signature ions)), or a fraction thereof, can then be directed to a second mass analyzer.

In the second mass analyzer, a second mass analysis can be performed on the selected ions, and the fragments thereof. The second mass analysis can determine the gross mass (or m/z) and relative amount of each unique reporter ion that is present at the selected mass to charge ratio as well as the mass (gross and/or absolute) of some or all of the daughter fragment ions of at least one labeled analyte of the sample mixture. For each analyte present at the selected mass to charge ratio, the daughter fragment ions can be used to identify the analyte and/or analytes present at the selected mass to charge ratio. For example, this analysis can be done as previously described in the section entitled: "Analyte Determination By Computer Assisted Database Analysis". Thus, in some embodiments, the method further comprises determining the gross mass and relative amount of each signature ion in the second mass analysis and the gross and/or absolute mass of some or all of the daughter fragment ions in the second mass analysis. Whether the reagents are from an isobaric set, a mass differential set or a combination of isobaric and mass differential reagents, it is possible to obtain identification and quantification of the analyte by analysis of a single mass spectrum or single data set used to produce a mass spectrum since the relevant information on reporter ions and daughter fragment ions are present in the same data set or spectrum. In some embodiments, the method further comprises determining the labeled analyte (and/or a precursor thereto) associated with the selected mass to charge ratio by analysis of the daughter fragment ions.

In some embodiments, certain steps of the process can be repeated one or more times. For example, in some embodiments, ions of a selected mass to charge ratio from the first mass spectrometric analysis, different from any previously selected mass to charge ratio, can be treated to dissociative energy to thereby form ionized reporter moieties (i.e. signature ions) and daughter fragment ions of at least some of the selected ions, as previously described. A second mass analysis of the selected ions, the reporter ions and/or the daughter fragment ions, or a fraction thereof, can be performed. The gross mass and relative amount of each unique signature ion in the second mass analysis and the mass (gross or absolute) of the daughter fragment ions can also be determined. Optionally, the labeled analyte (or precursor molecule) associated with the selected mass to charge ratio can be determined by analysis of the daughter fragment ions. In this way, the information can be made available for identifying and/or quantifying one or more additional analytes from the first mass analysis.

In some embodiments, it may be useful to repeat the process one or more times where the sample mixture has been fractionated (e.g. separated by chromatography or electrophoresis). For example, by repeating the process on one or more additional fractions of the sample, it is possible to analyze the entire sample mixture. It is contemplated that in some embodiments, the whole process can be repeated one or more times and within each of these repeats, certain steps can also be repeated one or more times such as described above. In this way, the contents of sample mixture can be interrogated and determined to the fullest possible extent. The entire process can also be repeated on a new set of two or more samples.

Those of ordinary skill in the art of mass spectrometry will appreciate that the first and second mass analysis can be performed in a tandem mass spectrometer. Instruments suitable for performing tandem mass analysis have been previously described herein. Although tandem mass spectrometers are preferred, single-stage mass spectrometers may be used. For example, analyte fragmentation may be induced by cone-voltage fragmentation, followed by mass analysis of the resulting fragments using a single-stage quadrupole or time-of-flight mass spectrometer. In other examples, analytes may be subjected to dissociative energy using a laser source and the resulting fragments recorded following post-source decay in time-of-flight or tandem time-of-flight (TOF-TOF) mass spectrometers.

As previously discussed, in some embodiments, the labeling reagents or the set of labeling reagents can be support bound. Accordingly, except for accommodating recapture of the labeled analytes from the support, the above described methods can be practiced with the support bound reagents.

This, in some embodiments, this invention pertains to practicing any of the above disclosed methods, wherein each different labeling reagent of the set is support bound and is linked to the support through a cleavable linker such that each different sample is reacted with a support carrying a different labeling reagent of the set and wherein the method further comprises, after performing the step of labeling the sample but before performing the step of mixing the labeled samples to prepare the sample mixture: i) optionally washing each support to remove components of each sample that do not react with the reactive group of the support bound labeling reagent; ii) cleaving the cleavable linker to thereby release the labeled analytes from each support, each differentially labeled sample comprising one or more labeled analytes wherein the labeled analytes associated with a particular sample are identifiable and/or quantifiable by the reporter moiety of unique mass linked thereto; and iii) optionally collecting the labeled analytes of each sample prior to mixing them.

In some embodiments, methods of the invention can further comprise digesting each sample with at least one enzyme to partially, or fully, degrade components of the sample prior to performing the labeling of the analytes of the sample (Also see the above section entitled: "*Sample Processing*"). For example, the enzyme can be a protease (to degrade proteins and/or peptides) or a nuclease (to degrade nucleic acids). Two or more enzymes may also be used together to thereby further degrade sample components. For example, the enzyme can be a proteolytic enzyme such as trypsin, papain, pepsin, ArgC, LysC, V8 protease, AspN, pronase, chymotrypsin or a carboxypeptidase (e.g. A, B, C, etc).

In some embodiments, methods can further comprise separating the sample mixture prior to performing the first mass analysis (Also see the above section entitled: "*Separation Including Separation Of The Sample Mixture*"). In this manner the first mass analysis can be performed on only a fraction of the sample mixture. The separation can be performed by any separations method, including by chromatography and/or by electrophoresis. For example, liquid chromatography/mass spectrometry (LC/MS) can be used to effect such a sample separation prior to the mass analysis. Moreover, any chromatographic separation process suitable to separate the analytes of interest can be used. Non-limiting examples of suitable chromatographic and electrophoretic separations processes have been described herein.

In some embodiments, the methods can be practiced with digestion and separation steps. While these steps are optional, they often are performed together, for example, when proteomic analysis is being done to thereby determine the up and down regulation of proteins in cells. In some embodiments, the steps of the methods, with or without the digestion and/or separation steps, can be repeated one or more times to thereby identify and/or quantify one or more other analytes in a sample or one or more analytes in each of the two or more samples (including samples labeled with support bound labeling reagents). Depending of whether or not a calibration standard is present in the sample mixture, the quantification of a particular analyte can be relative to the other labeled analytes, or it can be absolute.

As described previously, it is possible to determine the analyte associated with the selected ions by analysis of the mass (gross or absolute) of the daughter fragment ions. One such method of determination is described in the section entitled: "*Analyte Determination By Computer Assisted Database Analysis*". Once the analyte has been determined, information regarding the gross mass and relative amount of each unique reporter ion in the second mass analysis and the mass of daughter fragment ions provides the basis to determine other information about the sample mixture.

The relative amount of reporter ion can be determined by peak intensity in the mass spectrum. In some embodiments, the amount of each unique reporter ion can be determined by analysis of the peak height or peak width (or peak area) of the reporter ion (signature ion) obtained using a mass spectrometer. Because each sample can be labeled with a different labeling reagent and each labeling reagent can comprise a unique reporter moiety that produces a unique reporter ion that can be correlated with a particular differentially labeled sample used to formulate the sample mixture, determination of the different reporter ions in the second mass analysis can be used to identify the differentially labeled sample from which the reporter ions of the selected analyte originated. Where multiple reporter ions are found (e.g. according to the multiplex methods of the invention), the relative amount of each unique reporter ion can be determined with respect to the other reporter ions. Because the relative amount of each unique reporter ion determined in the second mass analysis can be correlated with the relative amount of an analyte in the sample mixture and because the ratios of samples used to prepare the sample mixture can be known, the relative amount (often expressed as concentration and/or quantity) of the analyte in each of the differentially labeled samples combined to form the sample mixture can be determined. Moreover, it is possible to relate the quantification information for an analyte to components of the original differentially labeled samples where an analyte that is determined is a by-product from another compound of interest (e.g. the analyte is a product of a degradation reaction such as where the analyte is a peptide formed by the digestion of a protein).

As discussed above, this analysis can be repeated one or more times on selected ions of a different mass to charge ratio to thereby obtain the relative amount of one or more additional analytes in each sample combined to form the sample mixture. Moreover, as appropriate, a correction of peak intensity associated with each unique reporter ion can be performed for naturally occurring, or artificially created, isotopic abundance, as previously discussed in the section entitled: "*Relative and Absolute Quantification of Analytes*".

In some embodiments, the analytes can be peptides in a sample or sample mixture. Analysis of the peptides in a sample, or sample mixture, can be used to determine the amount (often expressed as a concentration and/or quantity) of identifiable proteins in the sample or sample mixture wherein proteins in one or more samples can be degraded prior to the first mass analysis. Moreover, the information from different samples can be compared for the purpose of making determinations, such as for the comparison of the effect on the amount of the protein in cells that are incubated with differing concentrations of a substance that may affect cell growth, development, differentiation and/or death. Other, non-limiting examples may include comparison of the expressed protein components of diseased and healthy tissue or cell cultures. This may encompass comparison of expressed protein levels in cells, tissues or biological fluids following infection with an infective agent such as a bacteria or virus or other disease states such as cancer. In other examples, changes in protein concentration over time (timecourse) studies may be undertaken to examine the effect of drug treatment on the expressed protein component of cells or tissues. In still other examples, the information from different samples taken over time may be used to detect and monitor the concentration of specific proteins in tissues, organs or biological fluids as a result of disease (e.g. cancer) or infection. Such experiments may include one or more control samples. In some embodiments, the experiments can be used to determine two or more of the characteristics of interest described above.

Where a calibration standard comprising a unique reporter moiety is linked to an analyte, having the selected mass to charge ratio, has been added to the sample mixture in a known amount (often expressed as a concentration and/or quantity), the amount of the unique reporter associated with the calibration standard can be used to determine the absolute amount (often expressed as a concentration and/or quantity) of the analyte in each of the samples combined to form the sample mixture. This is possible because the amount of analyte associated with the unique reporter ion for the calibration standard in the sample mixture is known and the relative amounts of all unique reporter ions can be determined for the labeled analyte associated with the selected ions. Since the relative amount of each unique reporter ion, determined for each of the unique reporters moieties (including the reporter moiety for the calibration standard), is proportional to the amount of the analyte associated with each differentially labeled sample combined to form the sample mixture, the absolute amount (often expressed as a concentration and/or quantity) of the analyte in each of the samples can be determined based upon a ratio calculated with respect to the formulation used to produce the sample mixture. As appropriate, a correction of peak intensity associated with each of the unique reporter ions can be performed for naturally occurring, or artificially created, isotopic abundance. Such an analysis method can be particularly useful for proteomic analysis of multiplex samples of a complex nature, especially where a preliminary separation of the labeled analytes (e.g. liquid chromatography or electrophoretic separation) precedes the first mass analysis.

For example, if a sample mixture comprises 100 fmol/mL of a calibration standard and the relative intensity of the unique reporter ion associated with the calibration standard was 1 while the relative intensity of a first other unique reporter ion associated with a first sample was one-half and the relative intensity of a second other unique reporter ion associated with a second sample was 2, the amount of the analyte in the first differentially labeled sample mixed to form the sample mixture (assuming equal amounts of sample 1 and sample 2 are mixed to form the sample mixture) is 50 fmol/mL (0.5×100 fmol/mL) and the amount of the analyte in the second differentially labeled sample mixed to form the sample mixture is 200 fmol/mL (2×100 fmol/mL). Moreover, if, for example, the analyte is a peptide associated with a particular protein, it can be inferred that the amount of the protein in sample 1 is 50 fmol/mL and the amount of the protein in sample 2 is 200 fmol/mL. Thus, the presence of the calibration standard permits absolute quantification of the labeled analytes (and in some cases their precursors) in each differentially labeled sample mixed to form the sample mixture.

As previously discussed, in some embodiments, the absolute amount of each signature ion of unique mass, that corresponds to each unique reporter moiety, can be determined with reference to a calibration curve. Accordingly, the absolute amount of the determined analyte in each different sample of the sample mixture can be determined with reference to the absolute amount of each different signature ion of unique mass.

As previously discussed, this analysis can be repeated one or more times on selected ions of a different mass to charge ratio to thereby obtain the absolute amount of one or more additional analytes in each sample combined to form the sample mixture. Moreover, as appropriate, a correction of peak intensity associated with each unique reporter ion can be performed for naturally occurring, or artificially created, isotopic abundance, as previously discussed.

In some embodiments, methods described herein can be practiced using a labeling reagent that can be represented by formula II';

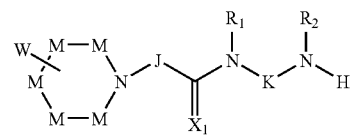

including a salt form and/or hydrate form thereof; wherein W, M, J, K, $R_1$, $R_2$ and $X^1$ are as previously described.

In some embodiments, methods described herein can be practiced using at least one labeling reagent that can be represented by formula III':

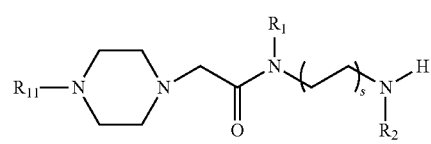

including a salt form and/or hydrate form thereof, wherein s, $R_1$, $R_2$, and $R_{11}$ are as previously described. For example, the method can be practiced using at least one labeling reagent represented by formula V' to XII' as illustrated below:

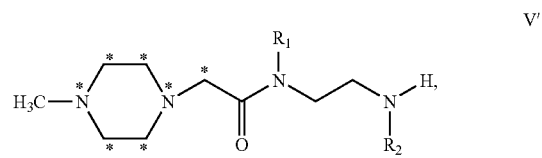

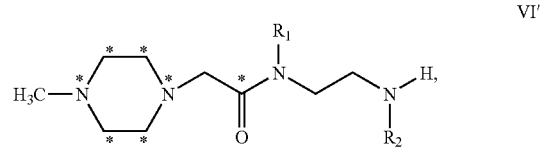

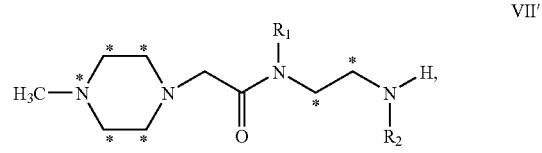

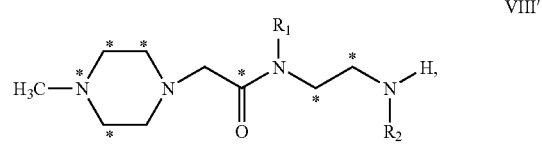

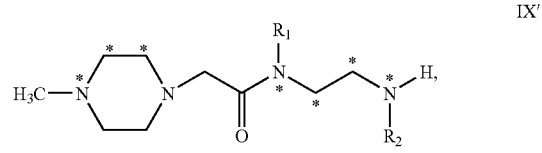

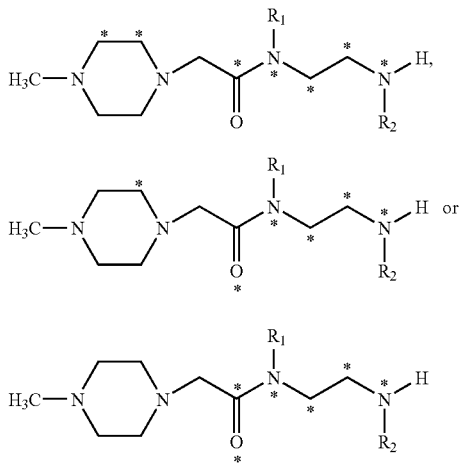

including a salt form and/or hydrate form thereof, wherein, $R_1$, and $R_2$ are as previously described and the symbol * indicates an isotopically enriched site comprising a $^{13}C$ substituted for $^{12}C$, $^{15}N$ substituted for $^{14}N$ or $^{18}O$ substituted for $^{16}O$, as appropriate.

In some embodiments, the method can be practiced using at least one labeling reagent that can be represented by formula IV';

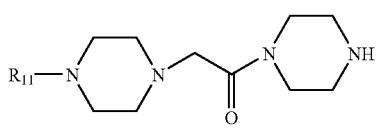

including a salt form and/or hydrate form thereof, wherein $R_{11}$ is as previously described. For example, the method can be practiced using at least one labeling reagent that can be represented by formula XV' to XXIII' as illustrated below;

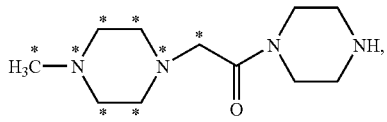

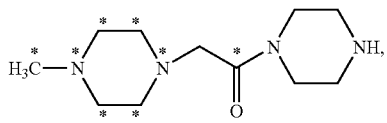

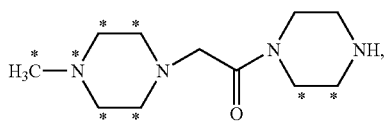

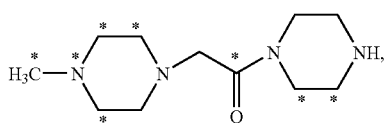

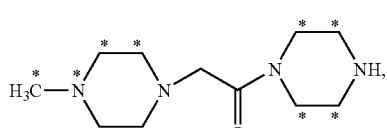

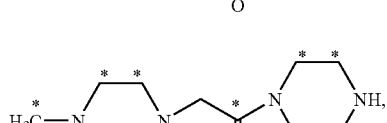

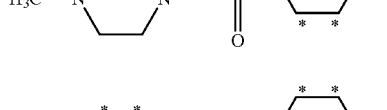

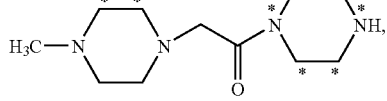

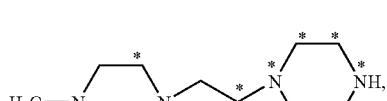

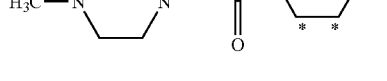

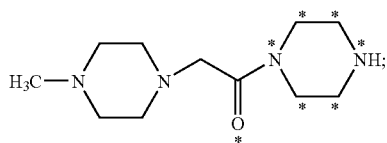

including a salt form and/or hydrate form thereof wherein, * indicates an isotopically enriched site comprising a $^{13}C$ substituted for $^{12}C$, $^{15}N$ substituted for $^{14}N$ or $^{18}O$ substituted for $^{16}O$, as appropriate.

In some embodiments, the method can be practiced using at least one labeling reagent that can be represented by formula III*';

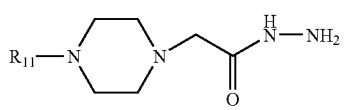

including a salt form and/or hydrate form thereof, wherein $R_{11}$ is as previously described. For example, the method can be practiced using at least one labeling reagent that can be represented by formula M' to MV' as illustrated below;

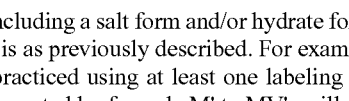

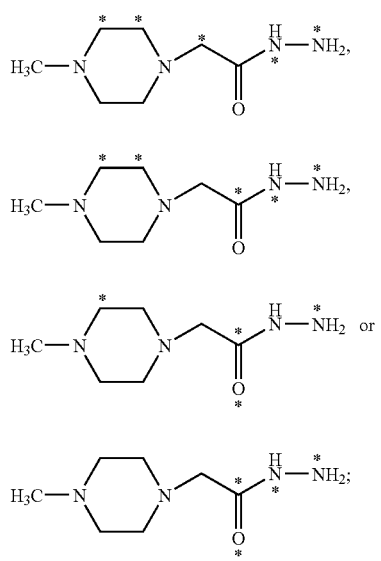

including a salt form and/or hydrate form thereof, wherein, * indicates an isotopically enriched site comprising a $^{13}C$ substituted for $^{12}C$, $^{15}N$ substituted for $^{14}N$ or $^{18}O$ substituted for $^{16}O$, as appropriate.

As discussed previously, in some embodiments the method can be performed using sets of mass differential tags. Therefore, in some embodiments, the method can further comprise performing a first mass spectrometric analysis on the sample mixture, or a fraction thereof, and determining the relative intensity of peaks associated with labeled analytes. Since the identity of the analytes can be determined by analysis of daughter ion fragments, the method can further comprising fragmenting ions of the labeled analytes to dissociative energy to thereby form daughter ion fragments and identifying the analyte from the daughter ion fragments.

In some embodiments, this method can be practiced using at least one labeling reagent that can be represented by formula XXV' to XXXII' as illustrated below;

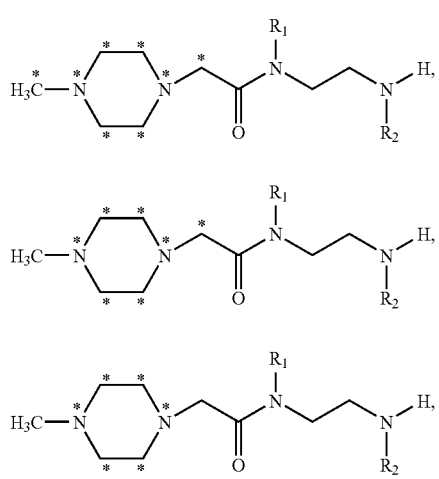

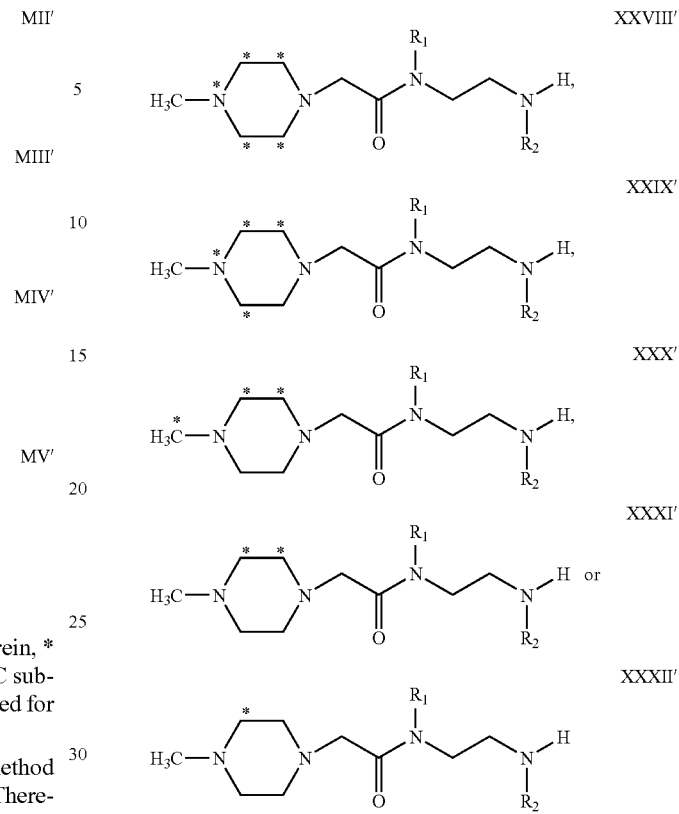

including a salt form and/or hydrate form thereof, wherein, * indicates an isotopically enriched site comprising a $^{13}C$ substituted for $^{12}C$, $^{15}N$ substituted for $^{14}N$ or $^{18}O$ substituted for $^{16}O$, as appropriate.

In some embodiments, this method can be practiced using at least one labeling reagent that can be represented by formula XXXV' to XXXXI' as illustrated below;

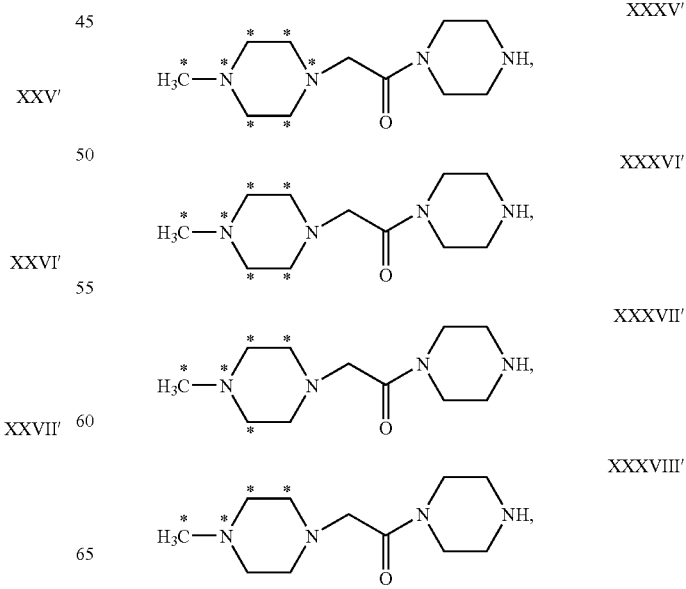

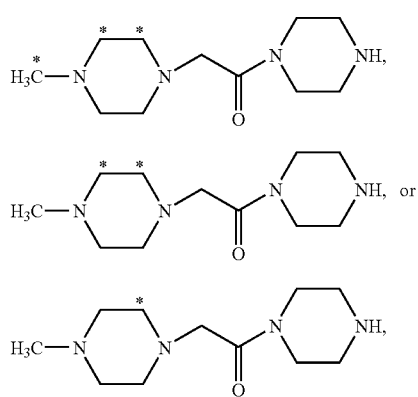

XXXIX'

XXXX'

XXXXI' including a salt form and/or hydrate form thereof, wherein, * indicates an isotopically enriched site comprising a $^{13}$C substituted for $^{12}$C, $^{14}$N substituted for $^{14}$N or $^{18}$O substituted for $^{16}$O, as appropriate.

In some embodiments, this method can be practiced using at least one labeling reagent that can be represented by formula MVI' to MXIII' as illustrated below;

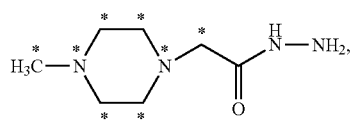

MVI'

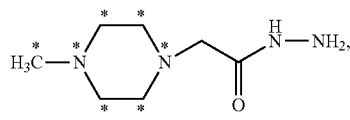

MVII'

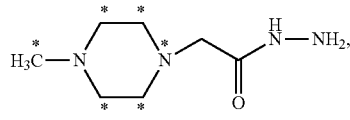

MVIII'

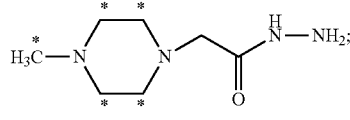

MIX'

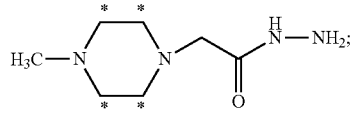

MX'

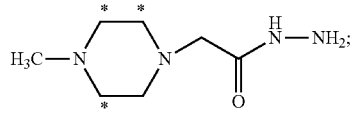

MXI'

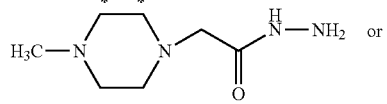

MXII'

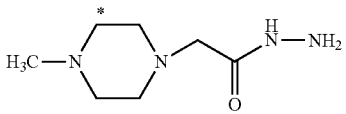

MXIII' including a salt form and/or hydrate form thereof, wherein, * indicates an isotopically enriched site comprising a $^{13}$C substituted for $^{12}$C, $^{15}$N substituted for $^{14}$N or $^{18}$O substituted for $^{16}$O, as appropriate.

Proteomic Workflows

In some embodiments, the labeling of the analytes of a sample can be performed prior to performing sample processing steps. In some embodiments, the labeling of analytes can be performed amongst other sample processing steps. In some embodiments, the labeling of analytes is the last step of sample processing and/or immediately precedes the preparation of a sample mixture.

Using proteomic analysis as a non-limiting example, there are at least several possible workflows that might be used. To aid in understanding of the following discussion a distinction is sometimes made between the precursor protein and the analyte peptide. However, it should be understood that in various embodiments either, or both, proteins and/or peptides could be considered analytes as described herein.

In one type of workflow, the precursor proteins can be digested to peptide analytes that can thereafter be labeled. In another type of workflow, the precursor proteins can be labeled with the labeling reagent and then digested to labeled peptide analytes. In another type of workflow, the precursor proteins can be captured on a solid support, digested and then the support bound peptides can be labeled. Optionally the flow through peptides can also be labeled. In another type of workflow, the precursor proteins can be captured on a solid support, labeled and then the support bound protein can be digested to produce labeled peptides. Optionally the flow through peptides can also be analyzed. Regardless of the workflow, additional sample processing (e.g. separation steps) can be performed on the labeled peptides as desired before MS and MS/MS analysis.

Exemplary Workflows Involving Digestion Followed by Labeling

As an example, there may be a "control" sample and a "test" sample to be analyzed. If, for the example, the goal is to analyze peptides (as the analytes) of "control" and "test" sample proteins, the proteins of the samples can, in some embodiments, be optionally reduced, optionally cysteine blocked and digested with an enzyme to thereby produce the analyte peptides that can be labeled for subsequent analysis. The analyte peptides can, in some embodiments, be labeled (tagged) without further sample processing. Regardless of how labeled, the analytes of each different sample can be labeled with using different labeling reagents each comprising a reporter moiety of unique mass (e.g. the labeling reagents of a set of isomeric and/or isobaric labels).

In some embodiments, further sample processing might be desired before labeling and/or after labeling. For example, a separation step might be performed to eliminate certain types of peptides that are not of interest, thereby decreasing the complexity of the sample. The labeled samples can be mixed to obtain a sample mixture. In some embodiments, the labeled analyte peptide can be subject to separation (e.g. high performance liquid chromatography (HPLC)) before mass spectral analysis.

Another exemplary embodiment includes optional steps of blocking and regeneration of the thiol groups of cysteine that can be involved with peptide capture. For the avoidance of doubt, it is self-evident that additional samples can be processed provided that additional differential labels are available to encode each different sample or sample fraction.

In some embodiments, the "control" sample and the "test" samples can be digested with an enzyme and then components of the sample can be captured on a solid phase through a cleavable linker. For example, the support can comprise a cleavable linker and a reactive group that reacts with moieties of a peptide.

In some embodiments, the peptides that flow through the support (because they do not react with the functional group of the support) can (instead of being discarded) be collected, labeled with a labeling reagent of a set of isobaric and/or mass differential labeling reagents and be analyzed separately or together with the labeled peptides collected from the support. The peptides that flow through the solid support can be labeled with the same or with a different labeling reagent of a set of labeling reagents. Regardless of the labeling reagent, they can optionally be mixed with the sample mixture that is analyzed by MS/MS analysis. They also can be independently analyzed. It is possible to label the peptides retained on the support either while still on the support or after they have been cleaved from the support.

It is also possible to use a solid support to capture the precursor proteins. For example, there can be two samples processed using a parallel path. The proteins that do not comprise a cysteine moiety can be removed from the support with a wash and optionally be collected (i.e. flow through). They can also be optionally digested, labeled and/or analyzed with the sample mixture or be analyzed separately.

The support bound proteins can be digested. The support bound cysteine comprising peptides can then be labeled with labeling reagent and cleaved from the support. The support bound cysteine comprising peptides can otherwise first be cleaved from the support and then labeled with labeling reagent. Labeled peptides from the different samples (optionally including the labeled peptides that do not comprise cysteine moieties) can be mixed, processed and/or analyzed with the sample mixture or be analyzed separately.

It is also possible to collect any peptides that are released from the support as a consequence of performing the digestion. Typically these are peptides that do not comprise a thiol group. These peptides can optionally be labeled with a labeling reagent and optionally mixed, processed and/or analyzed with the sample mixture or be analyzed separately.

Exemplary Workflows Involving Labeling Followed by Digestion

Whether or not a support is used to capture an analyte for analysis, the step of labeling the analyte with a labeling reagent can be performed either before or after digestion or other chemical treatment provided that the treatment does not modify the label in a way that would render it non-operative for quantifying labeled analytes as described herein. For protein samples, it is also possible to reduce and cysteine block the sample protein, label the N-ε-lysine side chain amine groups of the sample protein with the labeling reagent and then digest the protein into labeled peptides.

Regardless of their origin, labeled analytes can be analyzed or they can be further processed (including preparing a sample mixture), for example by separation and/or by immobilization to a support. The labeled protein can be cleaved from the support and then digested or the labeled protein can be digested while still support bound. In the latter case, support bound digestion will free peptides from the support that do not comprise a cysteine moiety. These can be collected and optionally analyzed either separately or as part of the sample mixture comprising the later released labeled peptides comprising cysteine moieties.

When the precursor proteins are labeled before digestion to peptides, the digestion pattern can be altered. For example, digestion with trypsin can be expected to produce predominately C-terminal arginine peptides because the N-ε-lysine side chain amine groups are modified with the label. Consequently, the activity of trypsin can be much like that of Arg-C. Because only those C-terminal arginine peptides that also comprise a lysine side chain can be labeled and therefore detectable in the mass spectrometer, this offers a way to further reduce the complexity of the sample to be further processed and/or analyzed.

In some embodiments, it is possible to reduce the protein and label the cysteine groups with labeling reagent (i.e. a thiol specific labeling reagent) and then digest the protein into labeled peptides for analysis. The labeled peptide analytes can be analyzed or can be further processed, for example by separation and/or immobilization to a support. For example, it is possible to immobilize labeled peptides to a support by reaction of the N-α-amine groups and/or the N-ε-amine groups of the lysine side chains with functional groups of the support. Supports with cleavable linkers for the immobilization of compounds comprising amine functional groups include supports comprising trityl linkers (See: Trityl chloride support (Trityl-Cl) or 2-Chlorotrityl chloride support available from Novabiochem (San Diego, Calif.)). This workflow is distinct from those described previously. The labeled analytes can be cleaved from the support, further processed and/or analyzed. This process might not provide substantial complexity reduction since all of the digested peptides are expected to comprise at least an N-α-amine group.

The foregoing examples are not intended to be exhaustive of various possible workflows. They are intended to be exemplary only. With regard to embodiments where labeling precedes digestion, it is also possible to engage in further sample processing prior to performing the digestion.

SUMMARY

Whilst the preceding discussion focused, by way of specific example, on proteomic analysis and the determination of peptides and/or proteins as analytes, the concepts described are intended to encompass many types of analytes for which the preceding workflows are applicable without the exercise of undue experimentation. Accordingly, the scope of this disclosure is not intended to be limited to any of these specific examples discussed.

IV. Mixtures

In some embodiments, this invention pertains to mixtures (i.e. sample mixtures). For example, the mixtures can comprise isobarically and/or mass differential labeled analytes. Exemplary mixtures of labeled analytes and methods for their preparation and/or analysis have been described in the section entitled "*Methods for Labeling and Analysis*", set forth above.

The mixture can be formed by mixing all, or a part, of the product of two or more labeling reactions wherein each sample is labeled with a different labeling reagent of a set of labeling reagent wherein each labeling reagent comprises a reporter moiety of unique (gross) mass. The unique reporter moiety of each different labeling reagent can identify from which labeling reaction each of the two or more labeled analytes is derived (i.e. originated). The labeling reagents can be isotopically encoded isobaric (and/or isomeric) and/or mass differential labeling reagents. Hence, two or more of the labeled analytes of a mixture can be isobaric (and/or isomeric) and/or mass differential. Characteristics of the labeling reagents and labeled analytes associated with those methods have been previously discussed.

The analytes of the mixture can be any analyte. For example, the analytes of the mixture can be peptides. The analytes of the mixture can be proteins. The analytes of the mixture can be peptides and proteins. The analytes of the mixture can be nucleic acid molecules. The analytes of the mixture can be carbohydrates. The analytes of the mixture can be lipids. The analytes of the mixture can be prostaglandins, the analytes of the mixture can be fatty acids. The analytes of the mixture can be carnitines. The analytes of the mixture can be amino acids. The analytes of the mixture can be vitamins. The analytes of the mixture can be steroids. The analytes of the mixture can be small molecules having a mass of less than 1500 daltons. The analytes of the mixture comprise two or more different analyte types (e.g. 1) lipids and steroids; or 2) peptides, lipids, steroids and carbohydrates).

Mixtures can comprise any type of differentially labeled analytes comprising novel reporter/linker moiety disclosed herein. For example, the mixtures can comprise at least two differentially labeled analytes that can be represented by formula I″;

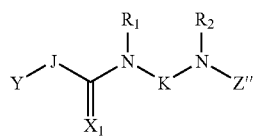

including a salt form and/or hydrate form thereof, wherein the atoms or groups Y, J, K, $R_1$, $R_2$, and X, have been previously described and their characteristics disclosed and wherein the group represented by formula I^;

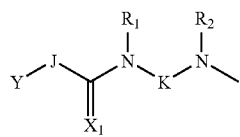

is the same for all labeled analytes associated with a particular sample but wherein the group of formula I^ comprises at least one isotopically enriched site that differs from that of any other labeled analyte that originates from a different sample combined to form the mixture. Z″ is the covalently linked analyte.

In some embodiments, each of the two-labeled analytes can originate from a different sample. In some embodiments the group Y-J formula I″, which group can form a reporter moiety, of each different labeled analyte can be uniquely encoded at one or more isotopically enriched sites such that when the bond between the group J, of the group Y-J, and the remainder of the labeled analyte fragments in a mass spectrometer, a reporter ion of unique mass is produced that is different from any reporter ion associated with any other labeled analyte that originates from a different sample combined to form the mixture and wherein said unique reporter ion is capable of identifying the sample from which the labeled analyte originated. The group Z″ can be a covalently linked analyte. For each different label, some of the labeled analytes of the mixture can be the same and some of the labeled analytes can be different.

In some embodiments, the group represented by formula I^;

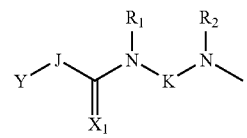

comprises a gross mass that is the same for all labeled analytes associated with a particular sample but that is different in gross mass from group of formula I^ associated with any other labeled analyte that originates from a different sample combined to form the mixture and wherein the gross mass of the group of formula I^ is capable of identifying the sample from which the labeled analyte originated.

In some embodiments, the mixture can comprise at least two differentially labeled analytes that can be represented by formula II″;

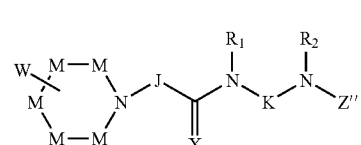

including a salt form and/or hydrate form thereof; wherein W, M, J, K, $R_1$, $R_2$, $X^1$, and Z″ are as previously described.

In some embodiments, the mixture can comprise at least two differentially labeled analytes wherein at least one labeled analyte is represented by formula III″;

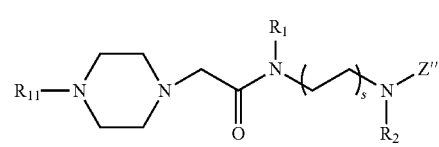

including a salt form and/or hydrate form thereof, wherein s, $R_1$, $R_2$, $R_{11}$ and Z″ are as previously described.

In some embodiments, the mixture can comprise at least two differentially labeled analytes wherein at least one labeled analyte is represented by formula V″, VI″, VII″, VIII″, IX″, X″, XI″ or XII″;

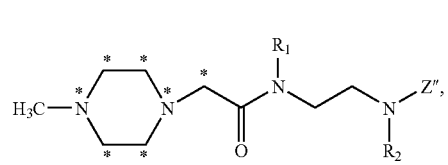

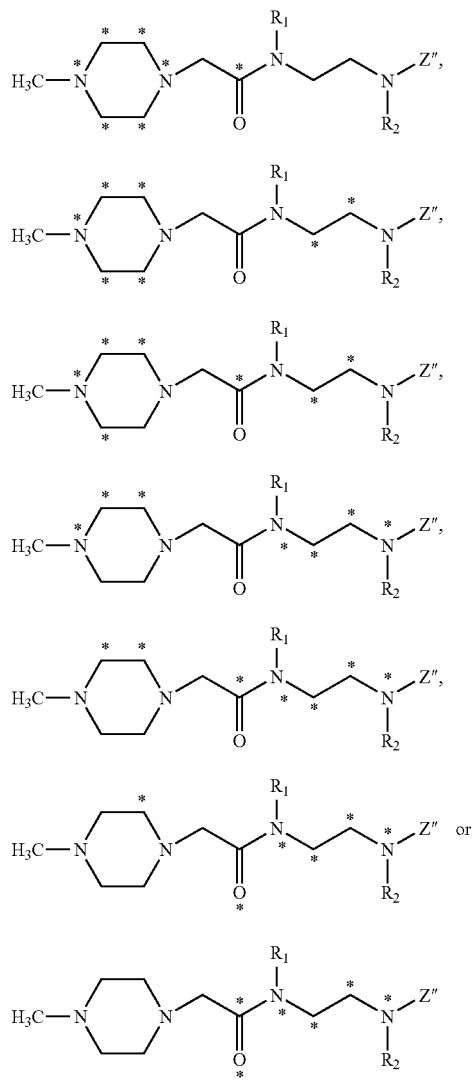

including a salt form and/or hydrate form thereof, wherein, * indicates an isotopically enriched site comprising a $^{13}$C substituted for $^{12}$C, $^{15}$N substituted for $^{14}$N or $^{18}$O substituted for $^{16}$O, as appropriate.

In some embodiments, the mixture can comprise at least two differentially labeled analytes wherein at least one labeled analyte is represented by formula XXV″, XXVI″, XXVII″, XXVIII″, XXIX″, XXX″, XXXI″ or XXXII″;

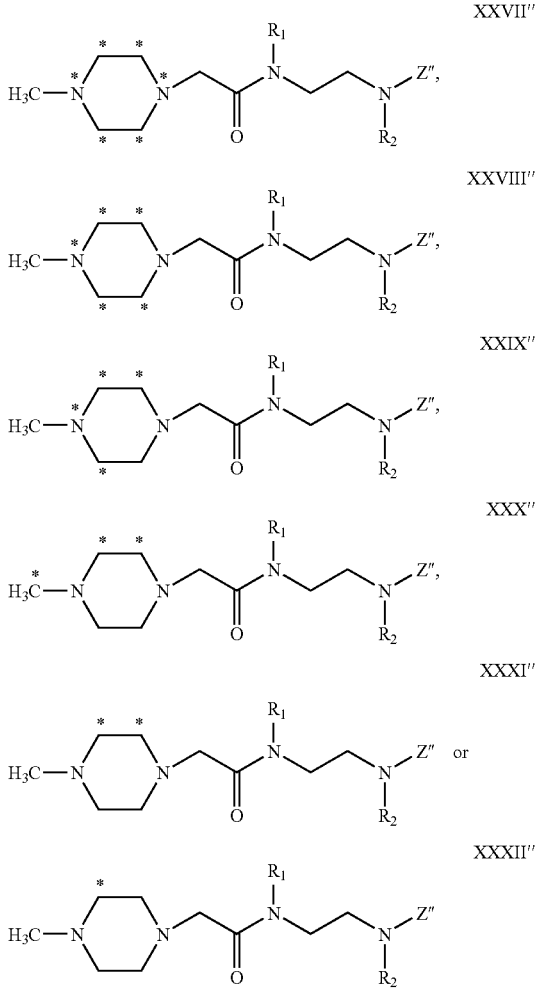

including a salt form and/or hydrate form thereof, wherein, * indicates an isotopically enriched site comprising a $^{13}$C substituted for $^{12}$C, $^{15}$N substituted for $^{14}$N or $^{18}$O substituted for $^{16}$O, as appropriate.

In some embodiments, the mixture can comprise at least two differentially labeled analytes wherein at least one labeled analyte is represented by formula IV″;

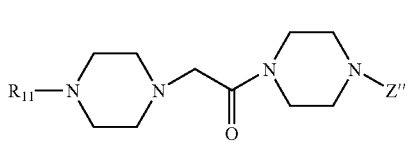

including a salt form and/or hydrate form thereof, wherein $R_{11}$ and Z″ are as previously described.

In some embodiments, the mixture can comprise at least two differentially labeled analytes wherein at least one labeled analyte is represented by formula XV″, XVI″, XVII″, XVIII″, XIX″, XX″, XXI″, XXII″ or XXIII″:

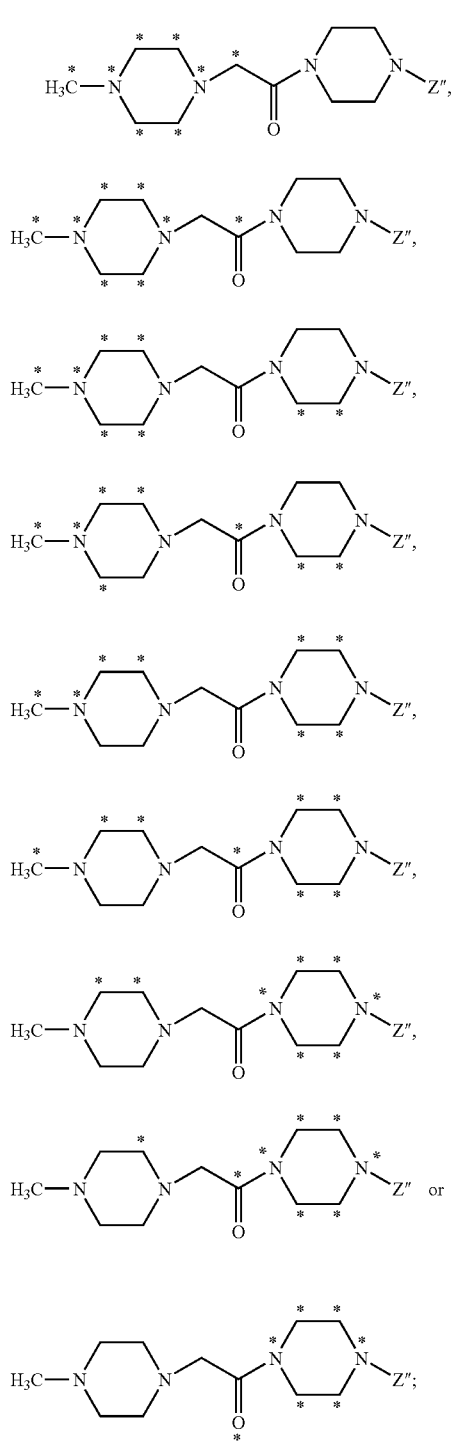

including a salt form and/or hydrate form thereof, wherein, * indicates an isotopically enriched site comprising a $^{13}C$ substituted for $^{12}C$, $^{15}N$ substituted for $^{14}N$ or $^{18}O$ substituted for $^{16}O$, as appropriate.

In some embodiments, the mixture can comprise at least two differentially labeled analytes wherein at least one labeled analyte is represented by formula XXXV", XXXVI", XXXVII", XXXVIII", XXXIX", XXXX" or XXXXI":

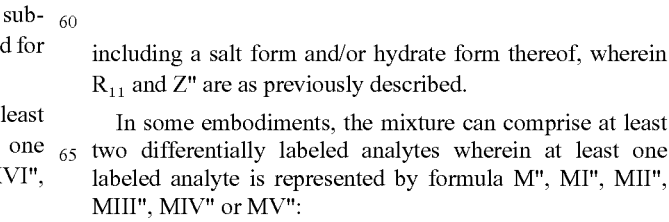

including a salt form and/or hydrate form thereof, wherein, * indicates an isotopically enriched site comprising a $^{13}C$ substituted for $^{12}C$, $^{15}N$ substituted for $^{14}N$ or $^{18}O$ substituted for $^{16}O$, as appropriate.

In some embodiments, the mixture can comprise at least two differentially labeled analytes wherein at least one labeled analyte is represented by formula III*";

III*"

including a salt form and/or hydrate form thereof, wherein $R_{11}$ and Z" are as previously described.

In some embodiments, the mixture can comprise at least two differentially labeled analytes wherein at least one labeled analyte is represented by formula M", MI", MII", MIII", MIV" or MV":

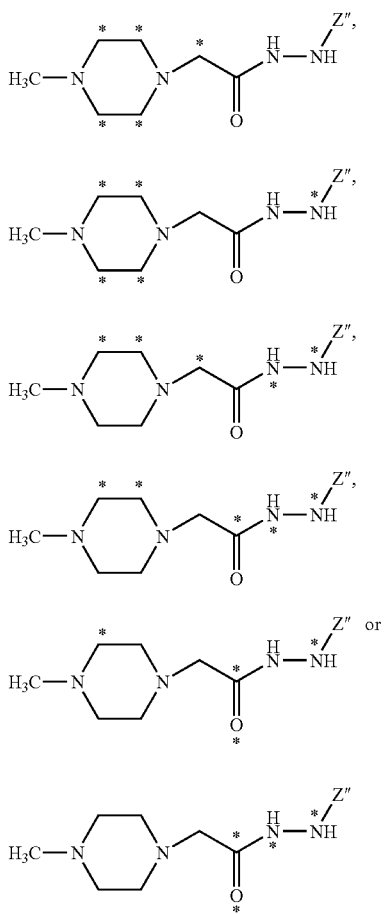

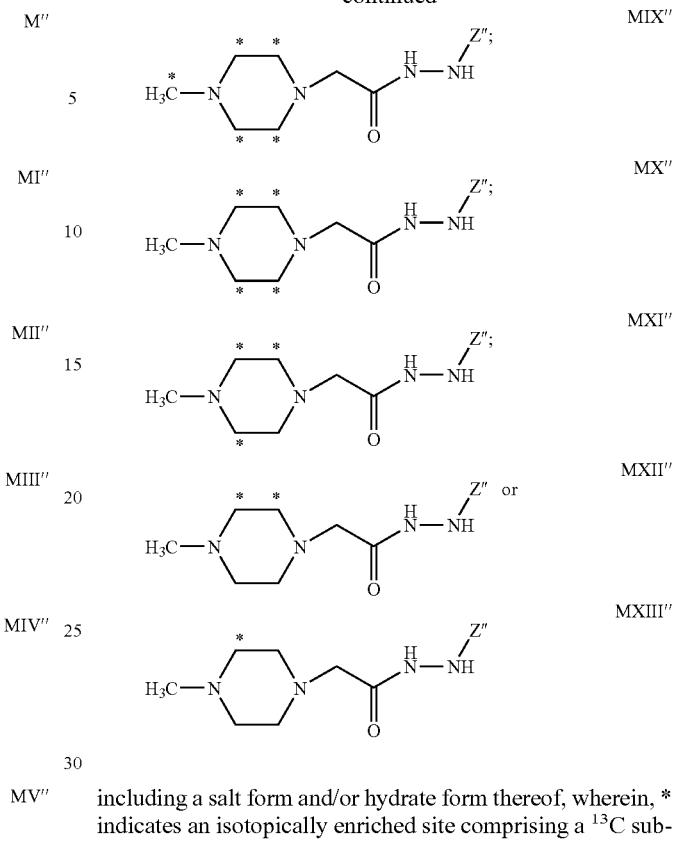

including a salt form and/or hydrate form thereof, wherein, * indicates an isotopically enriched site comprising a $^{13}$C substituted for $^{12}$C, $^{15}$N substituted for $^{14}$N or $^{18}$O substituted for $^{16}$O, as appropriate.

In some embodiments, the mixture can comprise at least two differentially labeled analytes wherein at least one labeled analyte is represented by formula MVI", MVII", MVIII", MIX", MX", MXI", MXII" or MXIII":

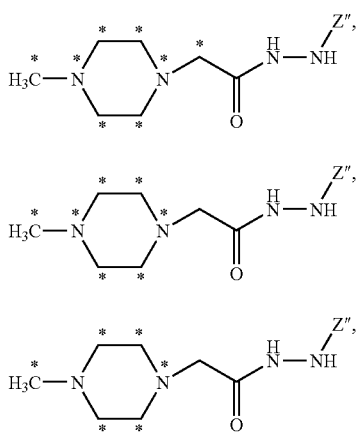

including a salt form and/or hydrate form thereof, wherein, * indicates an isotopically enriched site comprising a $^{13}$C substituted for $^{12}$C, $^{15}$N substituted for $^{14}$N or $^{18}$O substituted for $^{16}$O, as appropriate.

V. Kits

In some embodiments, this invention pertains to kits. The kits can comprise a labeling reagent as described herein and one or more other reagents, containers, enzymes, buffers and/or instructions. The kits can comprise a set of two or more labeling reagents and one or more other reagents, containers, enzymes, buffers and/or instructions. For example, the kit can comprise at least one additional reagent selected to perform an assay for quantifying one or more analytes in two or more different samples. For example, the kit can comprise a labeled calibration standard comprising a reporter moiety of unique gross mass. For example, the kit can comprise a labeled calibration standard comprising a label moiety of unique gross mass.

Two or more of the labeling reagents of a kit can be isomeric and/or isobaric. For example, one or more labeling reagents of the kits can be compounds (including sets of compounds) of the formula: I', II', III', IV', V', VI', VII', VIII', IX', XI', XI', XII', XIII', XV', XVI', XVII', XVIII', XIX', XX', XXI', XXII' and/or XXIII', as previously disclosed herein. In some embodiments, the kit can comprise a labeled analyte (for example as a calibration standard) of formula: I", II", III", IV", V", VI", VII", VIII", IX", X", XI", XII", XIII", XV", XVI", XVII", XVIII", XIX", XX", XXI", XXII" and/or XXIII", as previously disclosed herein. Other properties of the labeling reagents of the kits have been disclosed. The kits can, for example, be useful for the multiplex analysis of one or more analytes in the same sample, or in two or more different samples.

VI. Illustrative Labeling Reagents

It is to be understood that the below illustrated labeling reagents A and B each represent one of many possible labeling reagents that can be prepared and utilized. It is also to be understood that the ordinary practitioner, using no more that routine experimentation and the disclosure provided herein, could easily produce other labeling reagents of similar chemical structure. Accordingly, the disclosure is intended to be illustrative and is not intended to either be exhaustive or to be limiting in any way.

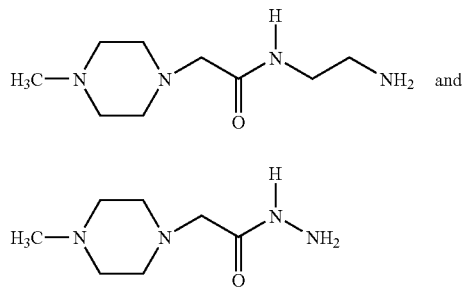

A

B

Exemplary isotopically encoded isobaric sets A and B of compounds that can be produced are shown. It is to be understood that the below illustrated labeling reagent sets each represent one of many possible sets of labeling reagents that can be prepared and utilized. It is also to be understood that the ordinary practitioner, using no more that routine experimentation and the disclosure provided herein, could easily produce other sets of labeling reagents of similar chemical structures. Accordingly, the disclosure is intended to be illustrative and is not intended to either be exhaustive or to be limiting in any way.

Exemplary Set A:

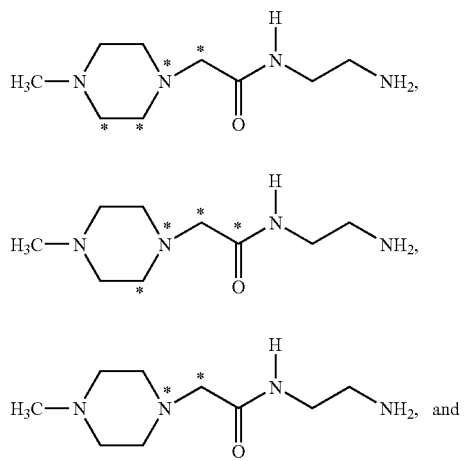

AI

AII

AIII

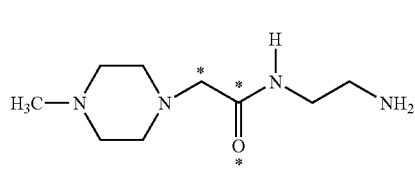

AIV

Exemplary Set B:

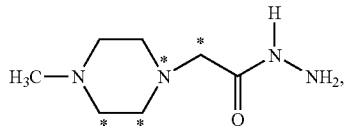

BI

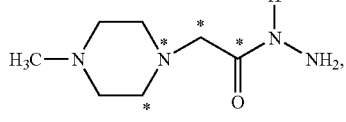

BII

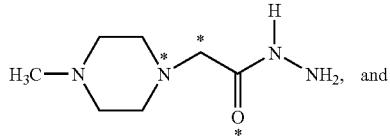

BIII

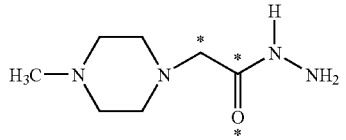

BIV

Exemplary isotopically encoded mass differential sets C and D of compounds that can be produced are shown. It is to be understood that the below illustrated labeling reagent sets each represent one of many possible sets of labeling reagents that can be prepared and utilized. It is also to be understood that the ordinary practitioner, using no more that routine experimentation and the disclosure provided herein, could easily produce other sets of labeling reagents of similar chemical structures. Accordingly, the disclosure is intended to be illustrative and is not intended to either be exhaustive or to be limiting in any way.

Exemplary Set C:

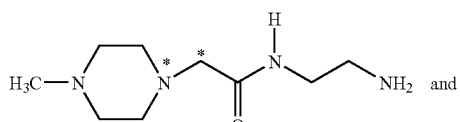

AI

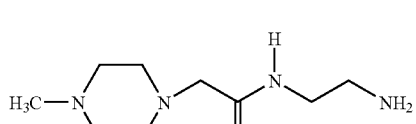

AV

Exemplary Set D:

BI

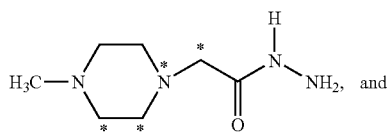

-continued

BV

[Structure: H3C—N(piperazine)N—CH2—C(=O)—N(H)—NH2]

Other exemplary isotopically encoded compounds that can be produced using the illustrated methods are described in this specification and the associated figures and claims.

While the present teachings are described in conjunction with various embodiments, it is not intended that the present teachings be limited to such embodiments. On the contrary, the present teachings encompass various alternatives, modifications and equivalents, as will be appreciated by those of skill in the art.

We claim:
1. A compound, represented by formula II;

II

[Structure with W, M, N, J, C(=X1), N(R1), K, N(R2), Z]

including a salt form and/or hydrate form thereof; wherein,
W is an atom or group that is substituted for at least one M group of the six membered heterocyclic ring and is located ortho, meta or para to the nitrogen of the six membered ring and is —N(H)—, —N(R")—, —N(R'")—, —P(R")—, —P(R'")—, —O— or —S—;
each remaining group M is, independently of the other, —CM'$_2$—, wherein each M' is, independently of the other, hydrogen, deuterium, fluorine, chlorine, bromine, iodine, —R$_8$, —OR$_8$, —SR$_8$, —R$_8$'OR$_8$ or —R$_8$'SR$_8$;
J is a group represented by formula —CJ'$_2$—, wherein each J' is, independently of the other, hydrogen, deuterium, fluorine, chlorine, bromine, iodine, —R$_3$, —OR$_3$, —SR$_3$, —R$_3$'OR$_3$ or —R$_3$'SR$_3$;
K is a group represented by formula —(CK'$_2$)$_n$— or —((CK'$_2$)$_m$—X$_2$—(CK'$_2$)$_m$)$_p$—, wherein n is an integer from 2 to 10, each m is, independently of the other, an integer from 1 to 5, p is an integer from 1 to 4 and each K' is, independently of the other, hydrogen, deuterium, fluorine, chlorine, bromine, iodine, —R$_4$, —OR$_4$, —SR$_4$, —R$_4$'OR$_4$ or —R$_4$'SR$_4$;
either
1) R$_1$ is hydrogen, deuterium or R$_6$ and R$_2$ is hydrogen, deuterium or R$_7$;
or
2) R$_1$ and R$_2$ taken together is a group represented by formula —(CR'$_2$)$_q$— or —((CR'$_2$)$_m$—X$_2$—(CR'$_2$)$_m$)$_p$— that forms a ring that bridges the two nitrogen atoms, wherein q is an integer from 1 to 10, each m is, independently of the other, an integer from 1 to 5, p is an integer from 1 to 4 and each R' is, independently of the other, hydrogen, deuterium, fluorine, chlorine, bromine, iodine, —R$_5$, —OR$_5$, —SR$_5$, —R$_5$'OR$_5$ or —R$_5$'SR$_5$;
X$_1$ is =O, =S, =NH or =NR$_7$;
each X$_2$ is, independently of the other, —O— or —S—;
each R" is, independently of the other, alkyl, alkenyl, alkynyl, aryl, heteroaryl or arylalkyl;

each R'" is H$_2$N—R$_9$'—, H(R$_{10}$)N—R$_9$'—, (R$_{10}$)$_2$N—R$_9$'—, HO—R$_9$'—, HS—R$_9$'— or a cleavable linker that cleavably links the compound to a support;
Z is hydrogen or a covalently linked analyte;
wherein,
each R$_3$, R$_4$, R$_5$, R$_6$, R$_7$, R$_8$ and/or R$_{10}$ is, independently of the other, alkyl, alkenyl, alkynyl, aryl, heteroaryl or arylalkyl;
each R$_3$', R$_4$', R$_5$', R$_6$', R$_8$' and/or R$_9$' is, independently of the other, alkylene, alkenylene, alkynylene, arylene or alkylarylene; and
the compound comprises at least one isotopically enriched site.

2. The compound of claim 1, represented by formula III;

III

[Structure: R11—N(piperazine)N—CH2—C(=O)—N(R1)—(CH2)s—N(R2)—Z]

including a salt form and/or hydrate form thereof;
wherein,
s is an integer from 1 to 5;
R$_1$ is hydrogen, deuterium or R$_6$;
R$_2$ is hydrogen, deuterium or R$_7$;
R$_{11}$ is hydrogen, deuterium, methyl, —C(H)$_2$D, —C(H)D$_2$, —CD$_3$, other alkyl or —R'"; and Z is hydrogen or a covalently linked analyte; wherein,
R'" is H$_2$N—R$_9$'—, H(R$_{10}$)N—R$_9$'—, (R$_{10}$)$_2$N—R$_9$', HO—R$_9$'—, HS—R$_9$'— or a cleavable linker that cleavably links the compound to a support; and
wherein,
each R$_6$, R$_7$ and/or R$_{10}$ is, independently of the other, alkyl, alkenyl, alkynyl, aryl, heteroaryl or arylalkyl; and
each R$_9$' is, independently of the other, alkylene, alkenylene, alkynylene, arylene or alkylarylene.

3. The compound of claim 2, wherein the compound is represented by formula V, VI, VII, VIII, IX, X, XI or XII:

V

[Structure with asterisks marking isotopic positions on piperazine and chain, H3C—N...N—CH2—C(=O)—N(R1)—CH2—CH2—N(R2)—Z]

VI

[Similar structure with different asterisk positions]

VII

[Similar structure with different asterisk positions]

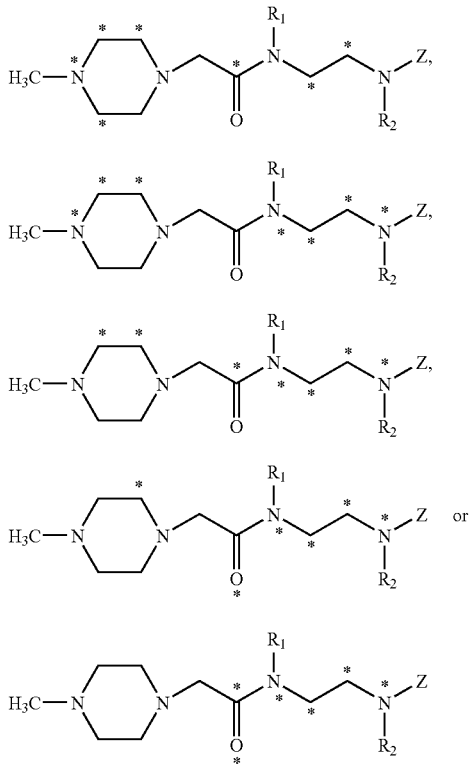

including a salt form and/or hydrate form thereof;
wherein,
* indicates an isotopically enriched site comprising a $^{13}C$ substituted for $^{12}C$, $^{15}N$ substituted for $^{14}N$ or $^{18}O$ substituted for $^{16}O$, as appropriate;
$R_1$ is hydrogen or $R_6$;
$R_2$ is hydrogen or $R_7$; and
Z is hydrogen or a covalently linked analyte; wherein,
$R_6$ and/or $R_7$ is, independently of the other, alkyl, alkenyl, alkynyl, aryl, heteroaryl or arylalkyl.

4. The compound of claim 2, wherein the compound is represented by formula XXV, XXVI, XXVII, XXVIII, XXIX, XXX, XXXI or XXXII:

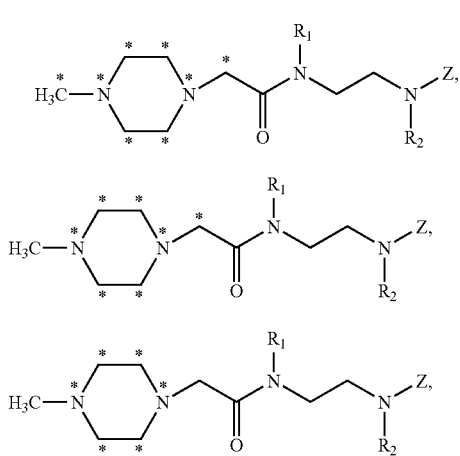

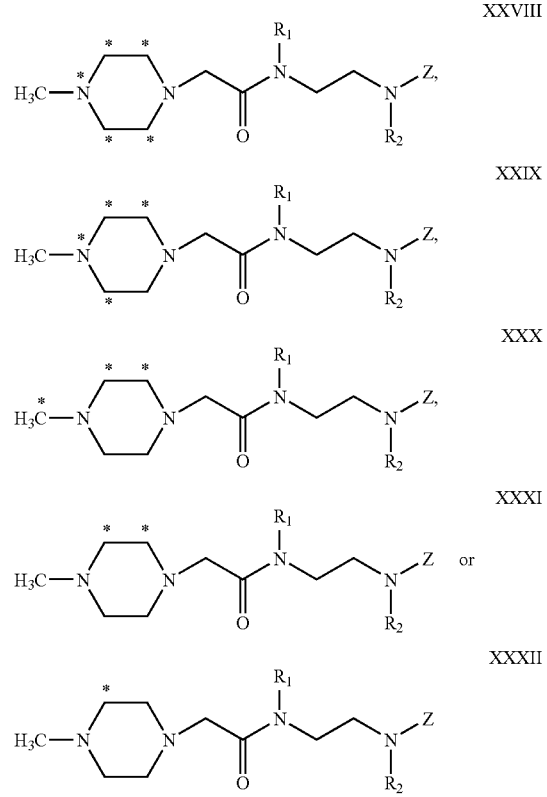

including a salt form and/or hydrate form thereof;
wherein,
* indicates an isotopically enriched site comprising a $^{13}C$ substituted for $^{12}C$ or $^{15}N$ substituted for $^{14}N$, as appropriate;
$R_1$ is hydrogen or $R_6$;
$R_2$ is hydrogen or $R_7$; and
Z is hydrogen or a covalently linked analyte; wherein,
$R_6$ and/or $R_7$ is, independently of the other, alkyl, alkenyl, alkynyl, aryl, heteroaryl or arylalkyl.

5. The compound of any of claim 1 or 2, wherein the compound comprises two or more isotopically enriched sites.

6. The compound of any one of claims 1-4, wherein Z is hydrogen.

7. The compound of any one of claims 1-4, wherein Z is a peptide and/or a protein.

8. The compound of any one of claims 1-4, wherein Z is a prostaglandin, a fatty acid, a carnitines, a carbohydrate, a lipid, an amino acid, a vitamin or a steroid.

9. The compound of any one of claims 1-4, wherein the compound is a calibration standard.

10. A method comprising:
   a) reacting two or more samples, each sample comprising one or more reactive analytes, with a different labeling reagent of a set of labeling reagents to thereby form two or more differentially labeled samples each comprising one or more labeled analytes wherein the different labeling reagents of the set are represented by formula I';

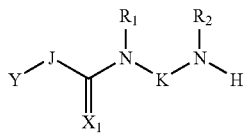

including a salt form and/or hydrate form thereof, wherein;

Y is a 5, 6 or 7 membered heterocyclic ring that may be substituted or unsubstituted and that may optionally be cleavably linked to a support, wherein the heterocyclic ring comprises at least one ring nitrogen atom that is linked through a covalent bond to the group J;

J is a group represented by formula —CJ'$_2$—, wherein each J' is, independently of the other, hydrogen, deuterium, fluorine, chlorine, bromine, iodine, —R$_3$, —OR$_3$, —SR$_3$, —R$_3$'OR$_3$ or —R$_3$'SR$_3$;

K is a group represented by formula —(CK'$_2$)$_n$— or —((CK'$_2$)$_m$—X$_2$—(CK'$_2$)$_m$)$_p$—, wherein n is an integer from 2 to 10, each m is, independently of the other, an integer from 1 to 5, p is an integer from 1 to 4 and each K' is, independently of the other, hydrogen, deuterium, fluorine, chlorine, bromine, iodine, —R$_4$, —OR$_4$, —SR$_4$, —R$_4$'OR$_4$ or —R$_4$'SR$_4$;

either

1) R$_1$ is hydrogen, deuterium or R$_6$ and R$_2$ is hydrogen, deuterium or R$_7$;

or

2) R$_1$ and R$_2$ taken together is a group represented by formula —(CR'$_2$)$_q$— or —((CR'$_2$)$_m$—X$_2$—(CR'$_2$)$_m$)$_p$— that forms a ring that bridges the two nitrogen atoms, wherein q is an integer from 1 to 10, each m is, independently of the other, an integer from 1 to 5, p is an integer from 1 to 4 and each R' is, independently of the other, hydrogen, deuterium, fluorine, chlorine, bromine, iodine, —R$_5$, —OR$_5$, —SR$_5$, —R$_5$'OR$_5$ or —R$_5$'SR$_5$;

X$_1$ is =O, =S, =NH or =NR$_7$;

each X$_2$ is, independently of the other, —O— or —S—;

each labeling reagent comprises at least one isotopically enriched site; and each R$_3$, R$_4$, R$_5$, R$_6$ and/or R$_7$ is, independently of the other, alkyl, alkenyl, alkynyl, aryl, heteroaryl or arylalkyl;

each R$_3$', R$_4$', and/or R$_5$' is, independently of the other, alkylene, alkenylene, alkynylene, arylene or alkylarylene; and b) mixing two or more of the differentially labeled samples, or a portion thereof, and optionally one or more calibration standards to thereby produce a sample mixture.

11. The method of claim 10, wherein the labeling reagents of the set are all isobaric.

12. The method of claim 10, wherein the labeling reagents of the set all have a different mass.

13. The method of claim 12, wherein the group Y-J of each different labeling reagent of the set is uniquely encoded at one or more isotopically enriched sites.

14. The method of claim 11, further comprising:
c) performing a first mass spectrometric analysis on the sample mixture, or a fraction thereof,
d) subjecting ions of the labeled analytes of a selected mass to charge ratio from the first mass spectrometric analysis to dissociative energy to thereby form reporter ions and daughter fragment ions of at least some of the selected ions; and
e) performing a second mass analysis of the selected ions, the reporter ions and/or the daughter fragment ions, or a fraction thereof.

15. The method of claim 14, further comprising:
f) determining the gross mass and relative amount of each reporter ion in the second mass analysis and the gross and/or absolute mass of some or all of the daughter fragment ions.

16. The method of claim 15, further comprising:
g) determining the labeled analyte associated with the selected mass to charge ratio by analysis of the daughter fragment ions.

17. The method of claim 16, further comprising:
h) repeating steps (d) through (f) or (d) through (g) one or more times on selected ions of the differentially labeled analytes at a different selected mass to charge ratio.

18. The method of claim 17, further comprising;
i) repeating steps (c) through (f), (c) through (g) or (c) through (h) one or more times, each time with a different fraction of the sample mixture.

19. The method of any one of claims 16 to 18, further comprising:
repeating steps (c) through (i) one or more times.

20. The method of any one of claims 10 to 18, wherein the group Y is a substituted or unsubstituted morpholine, piperidine or piperazine moiety.

21. The method of any one of claim 11 or 13, wherein each reporter ion of unique mass identifies the sample from which each labeled analyte originated.

22. The method of any one of claims 10 to 18, wherein each different labeling reagent of the set is support bound and is linked to the support through a cleavable linker such that each different sample is reacted with a support carrying a different labeling reagent of the set; and wherein the method further comprises cleaving the cleavable linker to release for collection the two or more differentially labeled samples.

23. The method of any one of claims 10 to 18, further comprising:
c) digesting each sample with at least one enzyme to partially, or fully, degrade components of the sample or sample mixture.

24. The method of any one of claims 10 to 18, further comprising:
c) separating the sample mixture.

25. The method of claim 15, wherein the relative amount of each reporter ion of unique mass in the second mass analysis is determined with respect to the other reporter ions.

26. The method of claim 25, wherein the relative amount of each reporter ion of unique mass associated with the identified analyte is correlated with the amount of each differentially labeled sample combined to form the sample mixture to thereby determine the relative amount of the analyte in each of the two or more differentially labeled samples combined to form the sample mixture.

27. The method of claim 25, wherein:
i) the sample mixture comprises a known amount of calibration standard for the determined analyte, wherein the calibration standard comprises a reporter moiety of unique mass for the determined analyte, and the absolute amount of each reporter ion of unique mass, that corresponds to each unique reporter moiety, is determined with reference to the amount of unique reporter ion associated with the calibration standard; and ii) the absolute amount of the determined analyte in each different sample of the sample mixture is determined with reference to the absolute amount of each different reporter ion of unique mass.

28. The method of claim 25, wherein:
   i) the absolute amount of each reporter ion of unique mass, that corresponds to each unique reporter moiety, is determined with reference to a calibration curve; and
   ii) the absolute amount of the determined analyte in each different sample of the sample mixture is determined with reference to the absolute amount of each different reporter ion of unique mass.

29. The method of claim 11, wherein at least one labeling reagent is represented by formula III';

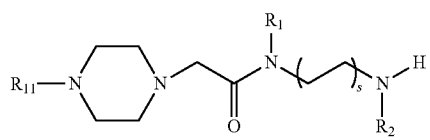

including a salt form and/or hydrate form thereof; wherein,
s is an integer from 1 to 5;
$R_1$ is hydrogen, deuterium or $R_6$;
$R_2$ is hydrogen, deuterium or $R_7$; and
$R_{11}$ is hydrogen, deuterium, methyl, —C(H)$_2$D, —C(H)D$_2$, —CD$_3$, other alkyl or —R'";
wherein,
R''' is H$_2$N—R$_9$'—, H(R$_{10}$)N—R$_9$'—, (R$_{10}$)$_2$N—R$_9$'—, HO—R$_9$'—, HS—R$_9$'— or a cleavable linker that cleavably links the compound to a support;
each $R_6$, $R_7$ and/or $R_{10}$ is, independently of the other, alkyl, alkenyl, alkynyl, aryl, heteroaryl or arylalkyl; and
each $R_9$' is, independently of the other, alkylene, alkenylene, alkynylene, arylene or alkylarylene.

30. The method of claim 29, wherein at least one labeling reagent is represented by formula V', VI', VII', VIII', IX', X', XI' or XII':

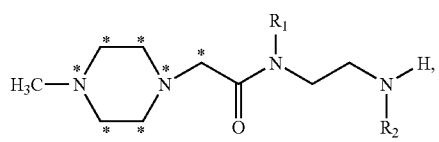

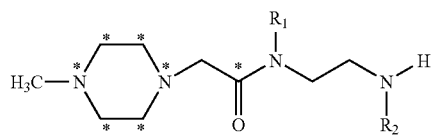

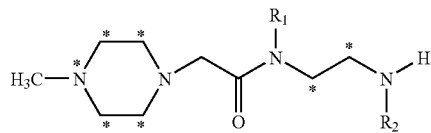

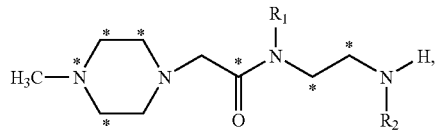

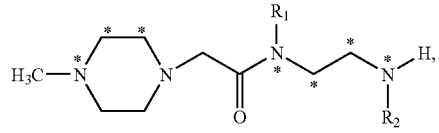

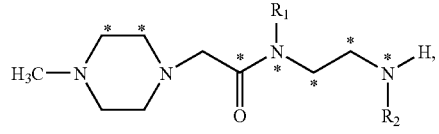

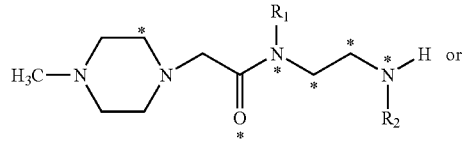

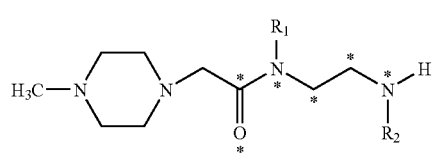

including a salt form and/or hydrate form thereof; wherein,
*indicates an isotopically enriched site comprising a $^{13}$C substituted for $^{12}$C, $^{15}$N substituted for $^{14}$N or $^{18}$O substituted for $^{16}$O, as appropriate;
$R_1$ is hydrogen or $R_6$;
$R_2$ is hydrogen or $R_7$; and
$R_6$ and/or $R_7$ is, independently of the other, alkyl, alkenyl, alkynyl, aryl, heteroaryl or arylalkyl.

31. The method of claim 12 or 13, further comprising:
   c) performing a first mass spectrometric analysis on the sample mixture, or a fraction thereof; and
   d) determining the relative intensity of peaks associated with labeled analytes.

32. The method of claim 31, further comprising:
   e) fragmenting ions of the labeled analytes to dissociative energy to thereby form daughter ion fragments; and
   f) identifying the analyte from the daughter ion fragments.

33. The method of claim 32, wherein at least one labeling reagent is represented by the formula XXV', XXVI', XXVII', XXVIII', XXIX', XXX', XXXI' or XXXII':

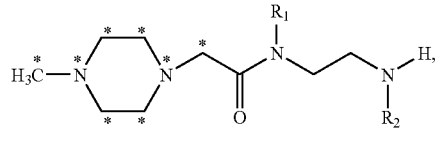

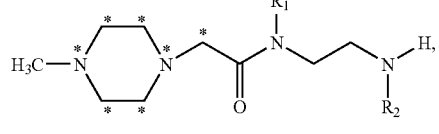

-continued

XXVII'

H₃C—*N*—*N*—CH₂—C(=O)—N(R₁)—CH₂—CH₂—N(R₂)H,

XXVIII'

H₃C—*N*—*N*—CH₂—C(=O)—N(R₁)—CH₂—CH₂—N(R₂)H,

XXIX'

H₃C—*N*—N—CH₂—C(=O)—N(R₁)—CH₂—CH₂—N(R₂)H,

XXX'

H₃C*—N—N—CH₂—C(=O)—N(R₁)—CH₂—CH₂—N(R₂)H,

XXXI'

H₃C—*N*—N—CH₂—C(=O)—N(R₁)—CH₂—CH₂—N(R₂)H or

XXXII'

H₃C—*N—N—CH₂—C(=O)—N(R₁)—CH₂—CH₂—N(R₂)H including a salt form and/or hydrate form thereof; wherein,
* indicates an isotopically enriched site comprising a $^{13}C$ substituted for $^{12}C$ or $^{15}N$ substituted for $^{14}N$, as appropriate;
$R_1$ is hydrogen or $R_6$;
$R_2$ is hydrogen or $R_7$; and
$R_6$ and/or $R_7$ is, independently of the other, alkyl, alkenyl, alkynyl, aryl, heteroaryl or arylalkyl.

34. A mixture comprising at least two labeled analytes, wherein at least two of the labeled analytes originate from different respective samples, wherein each labeled analyte of the mixture is represented by formula I":

I"

Y—J(=X₁)—N(R₁)—K—N(R₂)—Z"

including a salt form and/or hydrate form thereof, wherein;
Y is a 5, 6 or 7 membered heterocyclic ring that may be substituted or unsubstituted, wherein the heterocyclic ring comprises at least one ring nitrogen atom that is linked through a covalent bond to the group J;
J is a group represented by formula —CJ'₂—, wherein each J' is, independently of the other, hydrogen, deuterium, fluorine, chlorine, bromine, iodine, —$R_3$, —$OR_3$, —$SR_3$, —$R_3'OR_3$ or —$R_3'SR_3$;

K is a group represented by formula —(CK'₂)ₙ— or —((CK'₂)ₘ—X₂—(CK'₂)ₘ)ₚ—, wherein n is an integer from 1 to 10, each m is, independently of the other, an integer from 1 to 5, p is an integer from 1 to 4 and each K' is, independently of the other, hydrogen, deuterium, fluorine, chlorine, bromine, iodine, —$R_4$, —$OR_4$, —$SR_4$, —$R_4'OR_4$ or —$R_4'SR_4$;
either
1) $R_1$ is hydrogen, deuterium or $R_6$ and $R_2$ is hydrogen, deuterium or $R_7$;
or
2) $R_1$ and $R_2$ taken together is a group represented by formula —(CR'₂)q— or —((CR'₂)ₘ—X₂—(CR'₂)ₘ)ₚ— that forms a ring that bridges the two nitrogen atoms, wherein q is an integer from 1 to 10, each m is, independently of the other, an integer from 1 to 5, p is an integer from 1 to 4 and each R' is, independently of the other, hydrogen, deuterium, fluorine, chlorine, bromine, iodine, —$R_5$, —$OR_5$, —$SR_5$, —$R_5'OR_5$ or —$R_5'SR_5$;
$X_1$ is =O, =S, =NH or =NR₇;
each $X_2$ is, independently of the other, —O— or —S—; and
Z" is a covalently linked analyte;
wherein,
each $R_3$, $R_4$, $R_5$, $R_6$ and/or $R_7$ is, independently of the other, alkyl, alkenyl, alkynyl, aryl, heteroaryl or arylalkyl;
each $R_3'$, $R_4'$, and/or $R_5'$ is, independently of the other, alkylene, alkenylene, alkynylene, arylene or alkylarylene; and
wherein, the group represented by formula I^;

I^

Y—J(=X₁)—N(R₁)—K—N(R₂)— is the same for all labeled analytes associated with a particular sample but wherein the group of formula I^ comprises at least one isotopically enriched site that differs from that of any other labeled analyte that originates from a different sample combined to form the mixture.

35. The mixture of claim 34, wherein the group Y-J, which group forms a reporter moiety, is uniquely encoded at one or more isotopically enriched sites such that when the bond between the group J, of the group Y-J, and the remainder of the labeled analyte fragments in a mass spectrometer, a reporter ion of unique gross mass is produced that is different from any reporter ion associated with any other labeled analyte that originates from a different sample combined to form the mixture and wherein said unique reporter ion is capable of identifying the sample from which the labeled analyte originated.

36. The mixture of claim 34, wherein the group represented by formula I^;

I^

Y—J(=X₁)—N(R₁)—K—N(R₂)— comprises a gross mass that is the same for all labeled analytes associated with a particular sample but that is different in gross mass from group of formula I^ associated with any other labeled analyte that originates from a different sample combined to form the mixture and wherein the gross mass of the group of formula I^ is capable of identifying the sample from which the labeled analyte originated.

37. The mixture of any of claims 34 to 36, wherein one or more of the labeled analytes are peptides and/or proteins.

38. The mixture of any of claims 34 to 36, wherein one or more of the labeled analytes are prostaglandins, fatty acids, carnitines, carbohydrates, lipids, amino acids, vitamins and/or steroids.

39. The mixture of any of claims 34 to 36, wherein at least one labeled analyte is represented by formula III″;

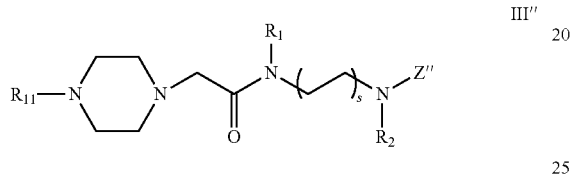

including a salt form and/or hydrate form thereof; wherein,
s is an integer from 1 to 5;
$R_1$ is hydrogen, deuterium or $R_6$;
$R_2$ is hydrogen, deuterium or $R_7$;
$R_{11}$ is hydrogen, deuterium, methyl, —C(H)$_2$D, —C(H)D$_2$, —CD$_3$, other alkyl or —R′″; and
Z″ is a covalently linked analyte; wherein,
R′″ is H$_2$N—R$_9$′—, H(R$_{10}$)N—R$_9$′—, (R$_{10}$)$_2$N—R$_9$′—, HO—R$_9$′—, HS—R$_9$′— or a cleavable linker that cleavably links the compound to a support;
each $R_6$, $R_7$ and/or $R_{10}$ is, independently of the other, alkyl, alkenyl, alkynyl, aryl, heteroaryl or arylalkyl; and
each $R_9$′ is, independently of the other, alkylene, alkenylene, alkynylene, arylene or alkylarylene.

40. The mixture of claim 35, wherein at least one labeled analyte is represented by Formula V″, VI″, VII″, VIII″, IX″, X″, XI″ or XII″:

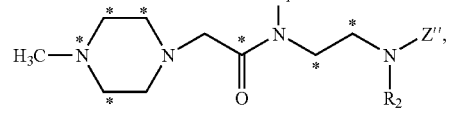

V′

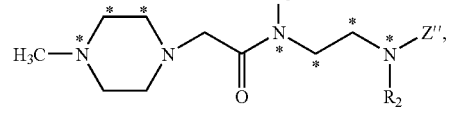

VI′

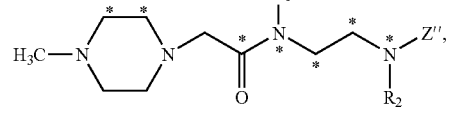

VII′

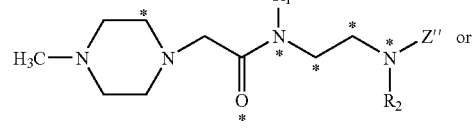

VIII′

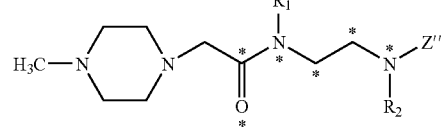

IX′

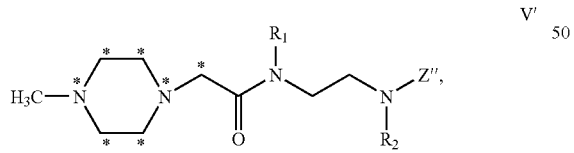

X′

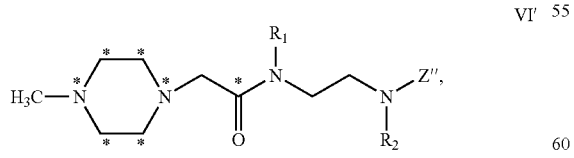

XI′ or

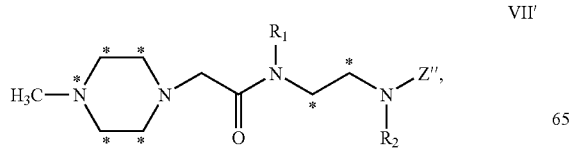

XII′ including a salt form and/or hydrate form thereof; wherein,
* indicates an isotopically enriched site comprising a $^{13}$C substituted for $^{12}$C, $^{15}$N substituted for $^{14}$N or $^{18}$O substituted for $^{16}$O, as appropriate;
$R_1$ is hydrogen or $R_6$;
$R_2$ is hydrogen or $R_7$; and
Z″ is a covalently linked analyte; wherein,
$R_6$ and/or $R_7$ is, independently of the other, alkyl, alkenyl, alkynyl, aryl, heteroaryl or arylalkyl.

41. The mixture of claim 36, wherein at least one labeled analyte is represented by formula XXV″, XXVI″, XXVII″, XXVIII″, XXIX″, XXX″, XXXI″ or XXXII″:

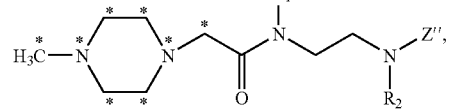

XXV″

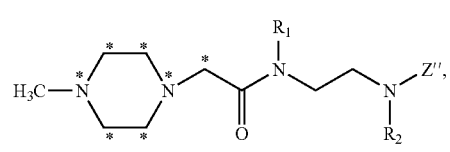

XXVI″

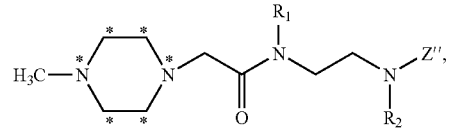

XXVII″

-continued

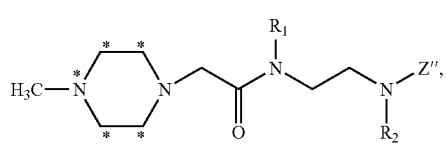
XXVIII″

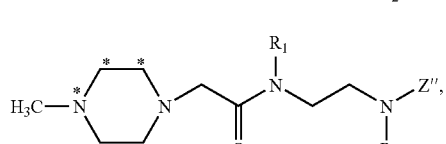
XXIX″

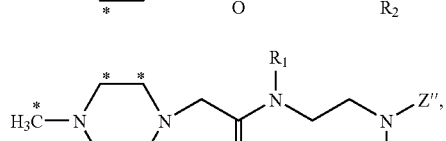
XXX″

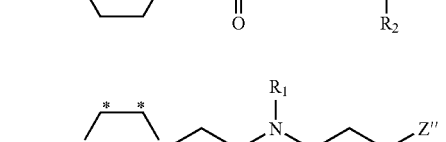
XXXI″ or

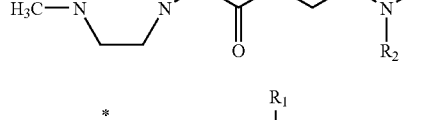
XXXII″ including a salt form and/or hydrate form thereof; wherein,
* indicates an isotopically enriched site comprising a $^{13}C$ substituted for $^{12}C$ or $^{15}N$ substituted for $^{14}N$, as appropriate;
$R_1$ is hydrogen or $R_6$;
$R_2$ is hydrogen or $R_7$; and
Z″ is a covalently linked analyte; wherein,
$R_6$ and/or $R_7$ is, independently of the other, alkyl, alkenyl, alkynyl, aryl, heteroaryl or arylalkyl.

42. A kit comprising at least one compound according to any one of claims 1 to 4.

43. The kit of claim 42, further comprising at least one additional reagent selected to perform an assay for quantifying one or more analytes in two or more different samples.

44. The kit of claim 42, wherein the compound is a labeled calibration standard comprising a reporter moiety of unique gross mass.

45. The kit of claim 42, wherein the compound is a labeled calibration standard comprising a label moiety of unique gross mass.

46. A compound represented by formula A:

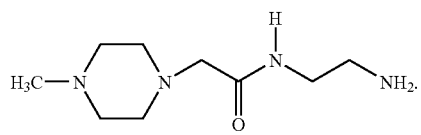
A wherein the compound comprises at least one isotopically enriched site.

47. A set of isobaric compounds, comprising the compounds represented by formula AI, AII, AIII, and AIV:

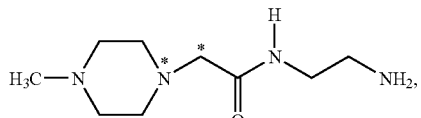
AI

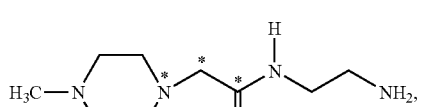
AII

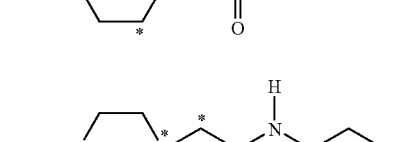
AIII

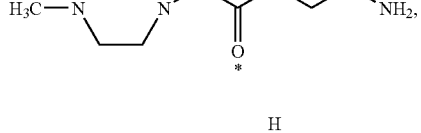
AIV wherein * indicates an isotopically enriched site comprising a $^{13}C$ substituted for $^{12}C$, $^{15}N$ substituted for $^{14}N$ or $^{18}O$ substituted for $^{16}O$, as appropriate.

48. A set of structurally similar compounds of different gross mass, comprising the compounds represented by formula AI and AV:

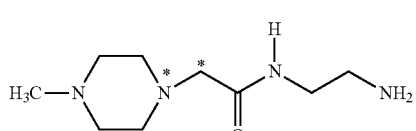
AI and

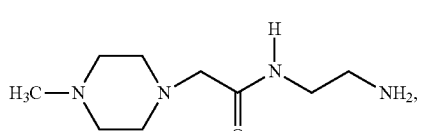
AV wherein * indicates an isotopically enriched site comprising a $^{13}C$ substituted for $^{12}C$ or $^{15}N$ substituted for $^{14}N$, as appropriate.

* * * * *